(12) United States Patent
Caponigro et al.

(10) Patent No.: US 11,376,239 B2
(45) Date of Patent: *Jul. 5, 2022

(54) PHARMACEUTICAL COMBINATIONS

(71) Applicant: Array BioPharma Inc., Boulder, CO (US)

(72) Inventors: Giordano Caponigro, Cambridge, MA (US); Zhu Alexander Cao, Cambridge, MA (US)

(73) Assignee: ARRAY BIOPHARMA INC, Boulder, CO (US)

(*) Notice: Subject to any disclaimer, the term of this patent is extended or adjusted under 35 U.S.C. 154(b) by 191 days.

This patent is subject to a terminal disclaimer.

(21) Appl. No.: 16/580,505

(22) Filed: Sep. 24, 2019

(65) Prior Publication Data

US 2020/0230108 A1    Jul. 23, 2020

Related U.S. Application Data

(63) Continuation of application No. 16/208,172, filed on Dec. 3, 2018, now Pat. No. 10,485,788, which is a
(Continued)

(51) Int. Cl.
*A61K 31/4184* (2006.01)
*A61K 31/506* (2006.01)
(Continued)

(52) U.S. Cl.
CPC ........ *A61K 31/4184* (2013.01); *A61K 9/0019* (2013.01); *A61K 9/0053* (2013.01);
(Continued)

(58) Field of Classification Search
None
See application file for complete search history.

(56) References Cited

U.S. PATENT DOCUMENTS 7,235,537 B2 *  6/2007  Wallace ............... C07D 235/06
                                                    514/80
8,501,758 B2    8/2013  Huang et al.
(Continued)

FOREIGN PATENT DOCUMENTS

WO    1996040210 A1    12/1996
WO    2003077914 A1    9/2003
(Continued)

OTHER PUBLICATIONS

Kirk-Othmer Encyclopedia of Chemical Technology Copyright © 2002 by John Wiley & Sons, Inc., pp. 95-147, Article Online Posting Date: Aug. 16, 2002 (Year: 2002).*
(Continued)

*Primary Examiner* — Karl J Puttlitz
(74) *Attorney, Agent, or Firm* — Banner & Witcoff, Ltd.

(57) ABSTRACT

Provided herein are pharmaceutical combinations comprising (a) a B-Raf inhibitor, or a pharmaceutically acceptable salt thereof, (b) at least one mitogen activated protein kinase (MEK) inhibitor, or a pharmaceutically acceptable salt thereof, and (c) an epidermal growth factor receptor (EGFR) inhibitor or a pharmaceutically acceptable salt thereof; and optionally at least one pharmaceutically acceptable carrier; methods for preparing the pharmaceutical combinations, and the uses of the pharmaceutical combinations in the treatment of proliferative diseases, such as cancer.

16 Claims, 6 Drawing Sheets

Related U.S. Application Data continuation of application No. PCT/US2017/035653, filed on Jun. 2, 2017.

(60) Provisional application No. 62/345,389, filed on Jun. 3, 2016.

(51) Int. Cl.
*A61K 39/395* (2006.01)
*A61P 35/04* (2006.01)
*A61K 45/06* (2006.01)
*A61K 31/573* (2006.01)
*A61P 35/00* (2006.01)
*C07K 16/28* (2006.01)
*A61K 9/00* (2006.01)
*A61K 39/00* (2006.01)

(52) U.S. Cl.
CPC .......... *A61K 31/506* (2013.01); *A61K 31/573* (2013.01); *A61K 39/39558* (2013.01); *A61K 45/06* (2013.01); *A61P 35/00* (2018.01); *A61P 35/04* (2018.01); *C07K 16/2863* (2013.01); *A61K 2039/545* (2013.01); *C07K 2317/24* (2013.01); *C07K 2317/76* (2013.01)

(56) References Cited

U.S. PATENT DOCUMENTS

| | | |
|---|---|---|
| 8,541,575 B2 | 9/2013 | Pulici et al. |
| 8,946,250 B2 * | 2/2015 | Pulici et al. |
| 9,238,627 B2 * | 1/2016 | Kreil .................. A61K 9/0009 |
| 9,314,464 B2 | 4/2016 | Huang et al. |
| 9,387,208 B2 | 7/2016 | Verma et al. |
| 9,474,754 B2 | 10/2016 | Caponigro et al. |
| 9,593,099 B2 | 3/2017 | Huang et al. |
| 9,593,100 B2 | 3/2017 | Huang et al. |
| 9,763,941 B2 | 9/2017 | Verma et al. |
| 9,850,229 B2 | 12/2017 | Huang et al. |
| 9,850,230 B2 | 12/2017 | Huang et al. |
| 9,913,844 B2 | 3/2018 | Caponigro et al. |
| 10,005,761 B2 | 6/2018 | Huang et al. |
| 10,258,622 B2 | 4/2019 | Verma et al. |
| 10,485,788 B2 | 11/2019 | Caponigro et al. |
| 2014/0275136 A1 | 9/2014 | Stuart et al. |
| 2015/0164897 A1 | 6/2015 | Caponigro et al. |
| 2015/0273057 A1 * | 10/2015 | Hoos .................... A61K 31/517 424/133.1 |
| 2018/0297985 A1 | 10/2018 | Huang et al. |
| 2018/0297986 A1 | 10/2018 | Huang et al. |
| 2019/0054086 A1 | 2/2019 | Verma et al. |

FOREIGN PATENT DOCUMENTS

| | | | |
|---|---|---|---|
| WO | 2008120004 A1 | | 10/2008 |
| WO | 2011025927 | * | 3/2011 |
| WO | 2011025927 A1 | | 3/2011 |
| WO | 2012170715 | * | 12/2012 |
| WO | 2012170715 A1 | | 12/2012 |
| WO | 2013070996 A1 | | 5/2013 |
| WO | 2013078264 A1 | | 5/2013 |
| WO | 2014025688 A1 | | 2/2014 |
| WO | 2014063024 A1 | | 4/2014 |
| WO | 2014066606 A2 | | 5/2014 |
| WO | 2014147573 A2 | | 9/2014 |
| WO | 2015087279 | * | 6/2015 |
| WO | 2015087279 A1 | | 6/2015 |
| WO | 2016131406 | * | 8/2016 |
| WO | 2016131406 A1 | | 8/2016 |
| WO | 2016155670 | * | 10/2016 |
| WO | 2016155670 A1 | | 10/2016 |
| WO | 2017019279 A1 | | 2/2017 |

OTHER PUBLICATIONS

Rouhi, "The Right Stuff, from research and development to the clinic, getting drug crystals right is full of pitfalls", Chemical & Engineering News, Feb. 24, 2003, pp. 32-35 (Year: 2003).*
Cutsem et al., Annals of Oncology, vol. 26, Jan. 1, 2015 (Jan. 1, 2015 (Year: 2015).*
"Study Comparing Combination of LGX818 Plus MEK162 Versus Vemurafenib and LGX818 Monotherapy in BRAF Mutant Melanoma", Jul. 26, 2013 (Jul. 26, 2013), downloaded from https://clinicaltrials.gov/ct2/show/NCT01909453?term=01909453&draw=2&rank=1 (Year: 2013).*
"Erbitux (cetuximab)" FDA approved drugs 2004 at https://www.centerwatch.com/drug-information/fda-approved-drugs/drug/850/erbitux-cetuximab downloaded Feb. 13, 2019 (Year: 2019).*
Wolpin et al., Gastroenterology May 2008; 134(5): 1296-1310 (Year: 2008).*
Fuerst, "Combination of BRAF Inhibitor Plus MEK Inhibitor Promising for PTC and Other Solid Tumors," Oncology Times 35, 10-11, 2013.
"Erbitux (cetuximab)" FDA approved drugs 2004 at https://www.centerwatch.com/drug-information/fda-approved-drugs/drug/850/-erbitux-cetuximab downloaded Feb. 13, 2019 (Year: 2004).
Boni et al., "Selective BRAFV600E Inhibition Enhances T-Cell Recognition of Melanoma without Affecting Lymphocyte Function," Cancer Res, 70, 5213-5219, 2010.
Connolly et al., "Anticancer activity of combination targeted therapy using cetuximab plus vemurafenib for refractory BRAFV600E-mutant metastatic colorectal carcinoma," Curr Oncol., vol. 21, e151-154, 2014.
Corcoran et al., "BRAF Gene Amplification Can Promote Acquired Resistance to MEK Inhibitors in Cancer Cells Harboring the Braf V600E Mutation," Sci Signal, 3(149): ra84, 20 pages, 2010.
Corcoran et al., "Combined BRAF and MEK Inhibition With Dabrafenib and Trametinib in BRAF V600—Mutant Colorectal Cancer," J Clin Oncol., vol. 33, No. 34, 4023-4031, 2015.
Corcoran et al., "Combined BRAF, EGFR, and MEK Inhibition in Patients with BRAFV600E—Mutant Colorectal Cancer," Cancer Discov., 8, 428-443, 2018.
Corcoran et al., "EGFR-Mediated Reactivation of MAPK Signaling Contributes to Insensitivity of BRAF—Mutant Colorectal Cancers to RAF Inhibition with Vemurafenib" Cancer Discov., 2(3): 227-35, 2012.
Cremolini et al., "FOLFOXIRI or FOLFOXIRI plus bevacizumab as first-line treatment of metastatic colorectal cancer: a propensity score-adjusted analysis from two randomized clinical trials","Annals of Oncology 27: 843-849, 2016".
Custem et al., Annals of Oncology, vol. 26, Issue suppl_4, Jun. 1, 2015, pp. iv119, Annals of Oncology, vol. 26, Issue suppl_4, Jun. 1, 2015, pp. iv119, https://doi.org/10.1093/annonc/mdv262.07 downloaded Feb. 13, 2019 (Year: 2015).
De Roock et al., "Effects of KRAS, BRAF, NRAS, and PIK3CA mutations on the efficacy of cetuximab plus chemotherapy in chemotherapy-refractory metastatic colorectal cancer: a retrospective consortium analysis","Lancet Oncol., p. 753-762, 2010".
Dummer et al., "Overall Survival in Columbus: A Phase 3 Trial of Encorafenib (ENCO) Plus Binimetinib (BINI) vs Vemurafenib (VEM) or ENCO in BRAF-Mutant Melanoma," ASCO, 27 pages, 2018.
Dummer et al., "Overall survival in patients with BRAF-mutant melanoma receiving encorafenib plus binimetinib versus vemurafenib or encorafenib (COLUMBUS): a multicentre, open-label, randomised, phase 3 trial," Lancet Oncol., 19, 1315-1327, 2018.
ESMO 2016: Triple Combination of Dabrafenib, Trametinib, and Panitumumab in Efficacy in BRAF Mutation Positive mCRC, 3 pages, 2016.
Falcone et al., "Phase III Trial of Infusional Fluorouracil, Leucovorin, Oxaliplatin, and Irinotecan (FOLFOXIRI) Compared With Infusional Fluorouracil, Leucovorin, and Irinotecan (FOLFIRI) as First-Line Treatment for Metastatic Colorectal Cancer: The Gruppo Oncologico Nord Ovest," J Clin Oncol., pp. 1670-1676, 2007.

(56) References Cited

OTHER PUBLICATIONS

Flaherty et al., "Inhibition of mutated, activated BRAF in metastatic melanoma.," N Engl J Med, 363(9), 809-819, 2010.

Giftin et al., "BRAF inhibitors: resistance and the promise of combination treatments for melanoma," Oncotarget, vol. 8 (No. 44), pp. 78174-78192, 2017.

Grob et al., "COMBI-v: Health-Related Quality-of-Life Impact of the Combination of Dabrafenib and Trametinib vs Vemurafenib in Patients With BRAF V600 Metastatic Melanoma," Poster Presentation at the 18.sup.th ECCO—40.sup. th ESMO European Cancer Congress, p. 222, 2015.

Hong et al., "Phase 1B study of vemurafenib in combination with irinotecan and cetuximab in patients with metastatic colorectal cancer with BRAFV600E mutation," Cancer Discov., 6(12): 1352-1365, 2016.

Huijberts et al., "BEACON CRC: Safety Lead-in (SLI) for the Combination of Binimetinib (BINI), Encorafenib (ENCO), and Cetuximab in Patients with BRAFV600E Metastatic Colorectal Cancer (mCRC)," ESMO, 1 page, 2017.

Kang et al., Ann Coloproctol 2013;29(4):150-154 (Year: 2013).

Kefford et al., "Phase I/II study of GSK2118436, a selective inhibitor of oncogenic mutant BRAF kinase, in patients with metastatic melanoma and other solid tumors.," J Clin Oncol., 28(15s), 8503-8503, 2010.

Kirk-Othmer Encyclopedia of Chemical Technology Copyright .COPYRGT. 2002 by John Wiley & Sons, Inc., pp. 95-147, Article Online Posting Date: Aug. 16, 2002 (Year: 2002).

Kopetz et al., "Updated Results of the BEACON Colorectal Cancer (CRC) Safety Lead-in: Encorafenib (ENCO) + Binimetinib (BINI) + Cetuximab (CETUX) for BRAF V600E—Mutant CRC," ASCO GI, 1 page, 2019.

Lee et al., "Options for Second-Line Treatment in Metastatic Colorectal Cancer," Clinical Advances in Hematology & Oneology vol. 14, Issue 1, 46-54, 2016.

Loupakis et al., "FOLFOXIRI plus bevacizumab as first-line treatment in BRAF mutant metastatic colorectal cancer," Eur J Cancer, 50, 57-63, 2014.

Loupakis et al., "Initial Therapy with FOLFOXIRI and Bevacizumab for Metastatic Colorectal Cancer," NEJM, 371; 17, 1609-1618, 2014.

Planchard et al., "Dabrafenib plus trametinib in patients with previously untreated BRAFV600E—mutant metastatic non-small-cell lung cancer: an open-label, phase 2 trial," Lancet Oncol., vol. 18, 1307-1316, 2017.

Prahallad et al., "Unresponsiveness of colon cancer to BRAF(V600E) inhibition through feedback activation of EGFR.," Nature, 483 (7387): 100-103, 2012.

Seligmann et al., "Investigating the poor outcomes of BRAF-mutant advanced colorectal cancer: analysis from 2530 patients in randomised clinical trials," Ann. Oncol., 28: 562-568, 2017.

Siena et al., Cancer. Apr. 1, 2010;116(7):1827-37 (Year: 2010).

Souglakos et al., "FOLFOXIRI (folinic acid, 5-fluorouracil, oxaliplatin and irinotecan) vs FOLFIRI (folinic acid, 5-fluorouracil and irinotecan) as first-line treatment in metastatic colorectal cancer (MCC): a multicentre randomised phase III trial from the Hellenic Oncology Research Group (HORG)," British Journal of Cancer, 94, 798-805, 2006.

Van Cutsem et al., Annals of Oncology, vol. 29, Issue suppl_5, Jun. 2018, mdy149.026,https://doi.org/10.1093/annonc/mdy149.026.

Van Cutsem et al., "BEACON CRC Study Safety Lead-in: Assessment of the BRAF Inhibitor Encorafenib + MEK Inhibitor Binimetinib + Anti-Epidermal Growth Factor Receptor Antibody Cetuximab for BRAFV600E Metastatic Colorectal Cancer," ESMO, 19 pages, 2018.

Van Cutsem et al., "ESMO consensus guidelines for the management of patients with metastatic colorectal cancer," Annals of Oncology 27: 1386-1422, 2016.

Wilmott et al., "Selective BRAF Inhibitors Induce Marked T-cell Infiltration into Human Metastatic Melanoma," Clin Cancer Res., 18(5), 1386-1394, 2012.

Yoshino et al., "Pan-Asian adapted ESMO consensus guidelines for the management of patients with metastatic colorectal cancer: a JSMO-ESMO initiative endorsed by CSCO, KACO, MOS, SSO and TOS," Annals of Oncology 29:44-70, 2018.

Anonymous, "Study Comparing Combination of LGX818 Plus MEK162 Versus Vemurafenib and LGX818 Monotherapy in BRAF Mutant Melanoma (COLUMBUS)," clinicaltrials.gov record No. NCT01909453, submitted Jul. 25, 2013, last updated posted Apr. 26, 2019, 14 pages.

Drummer et al., "Encorafenib plus binimetinib versus vemurafenib or encorafenib in patients with BRAF-mutant melanoma (COLUMBUS): a multicentre, open-label, randomised phase 3 trial," Lancet of Oncology 19, 603-15, May 1, 2018.

Extended European Search Report for EP 17807555.2, dated Jan. 23, 2020, 8 pages.

Van Cutsem et al., "Updated Results of the MEK inhibitor trametinib (T), BRAF inhibitor dabrafenib (D), and anti-EGFR antibody panitumumab (P) in patients (pts) with BRAF V600E mutated (BRAFm) metastatic colorectal cancer (mCRC)," Annals of Oncology 26 (Suppl. 4) iv117-iv121, 2015.

* cited by examiner

PHARMACEUTICAL COMBINATIONS

CROSS REFERENCE TO RELATED APPLICATIONS

This application is a continuation of U.S. application Ser. No. 16/208,172, filed Dec. 3, 2018, which is a continuation of International Application No. PCT/US2017/035653, filed Jun. 2, 2017, which claims the benefit of U.S. Provisional Application No. 62/345,389, filed on Jun. 3, 2016, which are incorporated herein by reference in their entirety.

FIELD OF THE INVENTION

The present invention relates to a pharmaceutical combination comprising therapeutically effective amounts, independently, of (a) a BRAF inhibitor, or a pharmaceutically acceptable salt thereof, (b) at least one mitogen activated protein kinase (MEK) inhibitor, or a pharmaceutically acceptable salt thereof, and (c) an epidermal growth factor receptor (EGFR) inhibitor or a pharmaceutically acceptable salt thereof; and optionally at least one pharmaceutically acceptable carrier; methods for preparing the pharmaceutical combinations, and the uses of the pharmaceutical combinations in the treatment of proliferative diseases, such as cancer.

The present invention also relates to a pharmaceutical combination comprising therapeutically effective amounts, independently, of (a) a BRAF inhibitor or a pharmaceutically acceptable salt thereof, (b) at least one mitogen activated protein kinase (MEK) inhibitor or a pharmaceutically acceptable salt thereof, and (c) an anti-EGFR antibody, and optionally at least one pharmaceutically acceptable carrier; the uses of such a combination in the treatment of proliferative diseases, such as cancer; and methods of treating a subject suffering from a proliferative disease, such as cancer, comprising administering a therapeutically effective amount of such a combination.

BACKGROUND OF THE INVENTION

The mitogen-activated protein kinase (MAPK) pathway mediates the activity of a number of effector molecules which coordinate to control cellular proliferation, survival, differentiation and migration. Stimulation of cells by, for example, growth factors, cytokines or hormones results in the plasma membrane-associated Ras becoming GTP-bound and thereby activated to recruit RAF. This interaction induces the kinase activity of RAF leading to direct phosphorylation of MAPK/ERK (MEK), which in turn phosphorylates the extracellular signal-related kinase (ERK). Activated ERK then phosphorylates a wide array of effector molecules, for example, kinases, phosphatases, transcription factors and cytoskeletal proteins. Therefore, the RAS-RAF-MEK-ERK signaling pathway transmits signals from cell surface receptors to the nucleus and is essential, for example, in cell proliferation and survival. The regulation of this signaling cascade is further enriched by the multiple isoforms of RAS (including KRAF, NRAS and HRAS), RAF (ARAF, BRAF, CRAF/RAF-1), MEK (MEK-1 and MEK-2) and ERK (ERK-1 and ERK-2). Research has shown this pathway regulates several key cellular activities including proliferation, differentiation, survival and angiogenesis. Inappropriate activation of proteins in this pathway has been shown to occur in many cancers, such as melanoma, non-small cell lung, colorectal and thyroid cancers. Since 10-20% of human cancers harbor oncogenic Ras mutations and many human cancers have activated growth factor receptors, this pathway is an ideal target for intervention.

The essential role and the position of RAF in many signaling pathways has been demonstrated from studies using deregulated and dominant inhibitory RAF mutants in mammalian cells as well as from studies employing biochemical and genetic techniques to model organisms. In the past, the focus on RAF being an anti-tumor drug target centered on its function as a downstream effector of RAS. However, recent findings suggest that RAF may have a prominent role in the formation of certain tumors with no requirement of an oncogenic Ras allele. In particular, activating alleles of BRAF and NRAS have been identified in about 70% of melanomas, 40% of papillary thyroid carcinoma, 30% of ovarian low-grade carcinoma, and 10% of colorectal cancers. Mutations in K-Ras occur in approximately 90% of pancreatic cancers. Most BRAF mutations are found within the kinase domain, with a single substitution (V600E) accounting for at least 80%. The mutated BRAF proteins activate the RAF-MEK-ERK pathway either via elevated kinase activity towards MEK or via activating CRAF. Data demonstrate that Raf kinase inhibitors can significantly inhibit signaling through the MAPK pathway, leading to dramatic shrinkage in BRAF (V600E) tumors. Colorectal cancer is the third most common cancer among men and women in the United States, with more than 134,000 new cases and nearly 50,000 deaths from the disease projected in 2016. In the United States, BRAF mutations occur in 8 to 15 percent of patients with colorectal cancer and represent a poor prognosis for these patients. Historical published progression-free survival (PFS) and overall survival (OS) results after first-line treatment range from 1.8 to 2.5 months and 4 to 6 months, respectively, and published response rates from various studies for EGFR-based therapy in this population range from 6 percent to 8 percent. Despite significant progress in the treatment of metastatic colorectal cancer, during the past 2 decades, the prognosis of patients with metastatic colorectal cancer (mCRC) remains disappointing. Systemic chemotherapy continues to be the main treatment modality for patients with mCRC (James J. Lee, MD, PhD, and Weijing Sun, MD, Clinical Advances in Hematology & Oncology, January 2016, Vol 14, Issue 1). The US Food and Drug Administration (FDA) has approved several cytotoxic agents and targeted agents for mCRC, including irinotecan, oxaliplatin, and capecitabine (S-1 has been approved in Japan and several other countries, but not in the United States). The combination of a fluoropyrimidine (5-fluorouracil [5-FU] or oral capecitabine) with either oxaliplatin or irinotecan has been widely accepted as standard cytotoxic chemotherapy for mCRC, as either first- or second-line therapy. These regimens consist of folinic acid/5-FU/oxaliplatin (FOLFOX), capecitabine/oxaliplatin (XELOX), folinic acid/5-FU/irinotecan (FOLFIRI), and capecitabine/irinotecan (XELIRI). More recently, in September of 2015, the FDA approved a combination of trifluridine and tipiracil (Lonsurf, Taiho Oncology) for use in refractory mCRC (James J. Lee, MD, PhD, and Weijing Sun, MD, Clinical Advances in Hematology & Oncology, January 2016, Vol 14, Issue 1).

EGFRs are transmembrane receptors present on cell membranes. They have an extracellular binding component, a transmembrane component and an intracellular tyrosine kinase component. EGFRs play an important role in controlling normal cell growth, apoptosis and other cellular functions. Deregulation of EGFR activity can lead to continual or abnormal activation of the receptors causing unregulated cell division. Epidermal growth factor receptor inhibitors are known in the art. Two categories of drugs affect EGFR: monoclonal antibodies and tyrosine kinase inhibitors (TKIs). Examples of monoclonal antibodies include panitumumab and cetuximab, and their method of action is through extracellular binding with subsequent inhibition of EGFR signaling pathways. Examples of tyrosine kinase inhibitors include erlotinib, gefitinib, and lapatinib, and their method of action is through intracellular binding and subsequent inhibition of EGFR signaling pathways.

In spite of numerous treatment options for patients with cancer, there remains a need for effective and safe therapeutic agents and a need for new combination therapies that can be administered for the effective long-term treatment of cancer.

SUMMARY OF THE INVENTION

Provided herein is a pharmaceutical combination comprising therapeutically effective amounts, independently, of (a) a BRAF inhibitor, or a pharmaceutically acceptable salt thereof, (b) at least one mitogen activated protein kinase (MEK) inhibitor, or a pharmaceutically acceptable salt thereof, and (c) an epidermal growth factor receptor (EGFR) inhibitor or a pharmaceutically acceptable salt thereof; and optionally at least one pharmaceutically acceptable carrier.

Also provided herein is a pharmaceutical combination comprising therapeutically effective amounts, independently, of (a) a BRAF inhibitor or a pharmaceutically acceptable salt thereof, (b) at least one MEK inhibitor or a pharmaceutically acceptable salt thereof, and (c) an anti-EGFR antibody; and optionally at least one pharmaceutically acceptable carrier.

Also provided herein is a pharmaceutical combination comprising therapeutically effective amounts, independently, of: (a) a BRAF inhibitor which is methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate or a pharmaceutically acceptable salt thereof, (b) at least one MEK inhibitor or a pharmaceutically acceptable salt thereof, and (c) an anti-EGFR antibody, and optionally at least one pharmaceutically acceptable carrier. In one embodiment, the BRAF inhibitor, the MEK inhibitor, and the anti-EGFR antibody are formulated as separate unit dosages for simultaneous, separate or sequential administration.

Also provided herein is a pharmaceutical combination comprising therapeutically effective amounts, independently, of: (a) a BRAF inhibitor which is methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate or a pharmaceutically acceptable salt thereof, (b) at least one MEK inhibitor, wherein at least one of said MEK inhibitors is 6-(4-bromo-2-fluorophenylamino)-7-fluoro-3-methyl-3H-benzoimidazole-5-carboxylic acid (2-hydroxyethoxy)-amide or a pharmaceutically acceptable salt thereof, and (c) an anti-EGFR antibody, and optionally at least one pharmaceutically acceptable carrier. In one embodiment, the BRAF inhibitor, the MEK inhibitor, and the anti-EGFR antibody are formulated as separate unit dosages for simultaneous, separate or sequential administration.

Also provided herein is a pharmaceutical combination comprising therapeutically effective amounts, independently, of: (a) a BRAF inhibitor which is methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate or a pharmaceutically acceptable salt thereof, (b) a MEK inhibitor which is 6-(4-bromo-2-fluorophenylamino)-7-fluoro-3-methyl-3H-benzoimidazole-5-carboxylic acid (2-hydroxyethoxy)-amide or a pharmaceutically acceptable salt thereof, and (c) an anti-EGFR antibody which is cetuximab, and optionally at least one pharmaceutically acceptable carrier. In one embodiment, the BRAF inhibitor, the MEK inhibitor, and the anti-EGFR antibody are formulated as separate unit dosages for simultaneous, separate or sequential administration.

Also provided are methods of treating a proliferative disease, comprising administering to a patient in need thereof a therapeutically effective amount of a pharmaceutical combination described herein.

Also provided is a pharmaceutical combination comprising therapeutically effective amounts, independently, of: (a) a BRAF inhibitor which is methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate or a pharmaceutically acceptable salt thereof, (b) at least one MEK inhibitor, and (c) an anti-EGFR-inhibitor antibody, and optionally at least one pharmaceutically acceptable carrier, for use in the treatment of a proliferative disease. In one embodiment, the MEK inhibitor is 6-(4-bromo-2-fluorophenylamino)-7-fluoro-3-methyl-3H-benzoimidazole-5-carboxylic acid (2-hydroxyethoxy)-amide or a pharmaceutically acceptable salt thereof. In one embodiment, the anti-EGFR-inhibitor antibody is cetuximab.

Also provided is a method of reducing the size of a tumor, comprising contacting the tumor with a pharmaceutical combination of the invention.

Also provided are methods for treating cancer in a patient in need thereof, the method comprising: (a) determining if the cancer in the patient is a BRAF-associated cancer; and (b) if the cancer is determined to be a BRAF-associated cancer, administering to the patient a therapeutically effective amount of a pharmaceutical combination of the invention.

Also provided is a method of treating cancer in a subject in need thereof, the method comprising (a) determining if the cancer has a mutant BRAF kinase, and (b) if the cancer is determined to have a mutant BRAF-kinase, administering to said subject a therapeutically effective amount of a pharmaceutical combination of the invention.

Also provided is a method of treating cancer in a subject in need thereof, the method comprising (a) detecting a mutant BRAF kinase in the cancer, and (b) administering to said subject a therapeutically effective amount of a pharmaceutical combination of the invention.

In one embodiment, provided herein are methods of treating a patient having colorectal cancer who has been prescribed treatment with cetuximab, comprising administering to said patient: (a) a therapeutically effective amount of a BRAF inhibitor which is methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate (COMPOUND A) or a pharmaceutically acceptable salt thereof, and (b) a therapeutically effective amount of a MEK inhibitor (COMPOUND B) or a pharmaceutically acceptable salt thereof.

In one embodiment, provided herein are methods of treating a patient having colorectal cancer, said method comprising: a) administering on a daily basis a first dose of (a) a therapeutically effective amount of a BRAF inhibitor which is methyl N-[(2S)-1-({4-[3-(5-chloro-2-fluoro-3- methanesulfonamidophenyl)-1-(propan-2-yl)-1H-pyrazol-4-yl]pyrimidin-2-yl}amino)propan-2-yl]carbamate (COMPOUND A) or a pharmaceutically acceptable salt thereof, and (b) a therapeutically effective amount of a MEK inhibitor (COMPOUND B) or a pharmaceutically acceptable salt thereof; b) at least 30 minutes after step a), administering a first therapeutically effective amount of a dosage amount of cetuximab; c) administering on a daily basis a second dose of said COMPOUND B, wherein said second dose is administered 10 to 14 hours after administration of said first dose of COMPOUND B; and d) administering on a weekly basis a second therapeutically effective amount of a dosage amount of cetuximab, wherein said administration of said second dosage amount of cetuximab is administered one week after administration of said first dosage amount of cetuximab.

Also provided are methods (e.g., in vitro methods) of selecting a treatment for a patient identified or diagnosed as having a BRAF-associated cancer.

Also provided herein are methods of selecting a treatment for a patient, wherein the methods include a step of performing an assay on a sample obtained from the patient to determine whether the patient has a dysregulation of a BRAF gene, a BRAF kinase, or expression or activity or level of any of the same, and identifying or diagnosing a patient determined to have a dysregulation of a BRAF gene, a BRAF kinase, or expression or activity or level of any of the same, as having a BRAF-associated cancer.

Also provided are methods of selecting a patient for treatment, wherein the methods include selecting, identifying, or diagnosing a patient having a BRAF-associated cancer, and selecting the patient for treatment including administration of a therapeutically-effective amount of a pharmaceutical combination of the invention.

Also provided are methods of determining the likelihood that a subject having a cancer will have a positive response to treatment with a pharmaceutical combination of the invention that include: determining whether a cancer cell in a sample obtained from the subject has one or more BRAF mutations; and determining that the subject having the cancer cell that has one or more BRAF mutations has a increased likelihood of having a positive response to treatment with a pharmaceutical combination of the invention.

Also provided are methods of predicting the efficacy of treatment with a pharmaceutical combination of the invention in a subject having cancer that include: determining whether a cancer cell in a sample obtained from the subject has one or more BRaf mutations; and determining that treatment with a pharmaceutical combination of the invention is more likely to be effective in a subject having a cancer cell in a sample obtained from the subject that has one or more BRAF mutations.

Also provided is a commercial package comprising as therapeutic agents a combination comprising (a) a BRAF inhibitor which is methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate or a pharmaceutically acceptable salt thereof, (b) at least one MEK inhibitor, and (c) an anti-EGFR antibody, and optionally at least one pharmaceutically acceptable carrier, together with instructions for simultaneous, separate or sequential administration thereof for use in the treatment of a proliferative disease. In one embodiment, the MEK inhibitor is 6-(4-bromo-2-fluorophenylamino)-7-fluoro-3-methyl-3H-benzoimidazole-5-carboxylic acid (2-hydroxyethoxy)-amide or a pharmaceutically acceptable salt thereof. In one embodiment, the anti-EGFR-inhibitor antibody is cetuximab.

Also provided is commercial package comprising (a) a BRAF inhibitor which is methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate or a pharmaceutically acceptable salt thereof, (b) at least one MEK inhibitor, together with instructions for simultaneous, separate or sequential administration thereof together with (COMPOUND C) in the treatment of a proliferative disease. In one embodiment, the MEK inhibitor is 6-(4-bromo-2-fluorophenylamino)-7-fluoro-3-methyl-3H-benzoimidazole-5-carboxylic acid (2-hydroxyethoxy)-amide or a pharmaceutically acceptable salt thereof. In one embodiment, the anti-EGFR-inhibitor antibody is cetuximab. In some embodiments, provided herein are methods of reducing toxicity (e.g., skin toxicity, gastrointestinal toxicity, myelosuppression, cardiac toxicity, neurocerebellar toxicity, or phototoxicity) of a combination of binimetinib and cetuximab in a subject, comprising administering encorafenib in combination with the binimetinib and cetuximab. In certain of these embodiments, the subject is selected as having a BRAF V600 (e.g., V600E) mutation.

In some embodiments, provided herein are methods of reducing toxicity (e.g., skin toxicity, gastrointestinal toxicity, myelosuppression, cardiac toxicity, neurocerebellar toxicity, or phototoxicity) of a combination of encorafenib and cetuximab in a subject, comprising administering binimetinib in combination with the encorafenib and cetuximab. In certain of these embodiments, the subject is selected as having a BRAF V600 (e.g., V600E) mutation.

In some embodiments, provided herein are methods of reducing adverse effects (e.g., reduction in visual acuity, diarrhea, hand-foot skin reactions, skin irritation (e.g., rash, pruritic lesions, fissuring, desquamation), cardiac arrest, edema, fatigue, asthenia, hypertension, pneumonitis, thrombosis (e.g., pulmonary thrombosis), acute renal failure, facial paresis, headache, or secondary neoplasms) of a first therapeutic agent selected from the group consisting of encorafenib, cetuximab, or binimetinib in a subject, comprising administering the other two therapeutic agents not selected from the group as the first therapeutic agent in combination with the first therapeutic agent. In certain of these embodiments, the first therapeutic agent is encorafenib and the other two therapeutic agents are cetuximab and binimetinib. In certain of these embodiments, the first therapeutic agent is cetuximab and the other two therapeutic agents are encorafenib and binimetinib. In certain of these embodiments, the first therapeutic agent is binimetinib and the other two therapeutic agents are cetuximab and encorafenib. In certain of these embodiments, the subject is selected as having a BRAF V600 (e.g., V600E) mutation.

In some embodiments, provided herein are methods of reducing one or more adverse events (e.g., skin toxicity, hand-foot-skin rash (HFSR), rash, rash acneiform, dermatitits, rentinopathy, or rental detachment) associated with a cancer therapeutic regimen in a subject identified as having a BRAF V600E colorectal cancer comprising: including binimetinib in a cancer treatment regimen which comprises encorafenib and an anti-EGFR antibody. In certain of these embodiments, the anti-EGFR antibody is selected from the group consisting of cetuximab, gefitinib, erlotinib, lapatinib, dacomitinib, neratinib, vanetanib, and panitumumab. In certain of these embodiments, the anti-EGFR antibody is cetuximab. In certain of these embodiments, the subject is selected as having a BRAF V600 (e.g., V600E) mutation.

In some embodiments, provided herein are methods of reducing one or more adverse events (e.g., skin toxicity, hand-foot-skin rash (HFSR), rash, rash acneiform, dermatitis, rentinopathy, or rental detachment) associated with a cancer therapeutic regimen in a subject identified as having a BRAF V600E colorectal cancer comprising: including encorafenib in a cancer treatment regimen which comprises binimetinib and an anti-EGFR antibody. In certain of these embodiments, the anti-EGFR antibody is selected from the group consisting of cetuximab, gefitinib, erlotinib, lapatinib, dacomitinib, neratinib, vanetanib, and panitumumab. In certain of these embodiments, the anti-EGFR antibody is cetuximab. In certain of these embodiments, the subject is selected as having a BRAF V600 (e.g., V600E) mutation.

In some embodiments, provided herein are methods of increasing the safe dosage of encorafenib in a subject, comprising administering the encorafenib in combination with binimetinib and cetuximab. In certain of these embodiments, the subject is selected as having a BRAF V600 (e.g., V600E) mutation.

In some embodiments, provided herein are methods of increasing the safe dosage of binimetinib in a subject, comprising administering the binimetinib in combination with encorafenib and cetuximab. In certain of these embodiments, the subject is selected as having a BRAF V600 (e.g., V600E) mutation.

In some embodiments, provided herein are methods of increasing the safe dosage of cetuximab in a subject, comprising administering the cetuximab in combination with binimetinib and encorafenib. In certain of these embodiments, the subject is selected as having a BRAF V600 (e.g., V600E) mutation.

In some embodiments, provided herein are methods of improving pharmacological efficacy of a combination of binimetinib and cetuximab in a subject, comprising administering encorafenib in conjunction with the binimetinib and cetuximab. In certain of these embodiments, the improvement in pharmacological efficacy is determined by magnetic resonance imaging (MRI) (e.g., whole-body bone MRI), computed tomography scan, X-ray analysis, Tc99m bone scan, fluorodeoxyglucose-positron emission tomography (FDG-PET), or sodium fluoride-positron emission tomography (NaF PET) scan. In certain of these embodiments, the subject is selected as having a BRAF V600 (e.g., V600E) mutation.

In some embodiments, provided herein are methods of improving pharmacological efficacy of a combination of encorafenib and cetuximab in a subject, comprising administering binimetinib in conjunction with the encorafenib and cetuximab. In certain of these embodiments, the improvement in pharmacological efficacy is determined by magnetic resonance imaging (MRI) (e.g., whole-body bone MRI), computed tomography scan, X-ray analysis, Tc99m bone scan, fluorodeoxyglucose-positron emission tomography (FDG-PET), or sodium fluoride-positron emission tomography (NaF PET) scan. In certain of these embodiments, the subject is selected as having a BRAF V600 (e.g., V600E) mutation.

In some embodiments, provided herein are methods of improving pharmacological efficacy of a combination of encorafenib and binimetinib in a subject, comprising administering cetuximab in conjunction with the encorafenib and binimetinib. In certain of these embodiments, the improvement in pharmacological efficacy is determined by magnetic resonance imaging (MRI) (e.g., whole-body bone MRI), computed tomography scan, X-ray analysis, Tc99m bone scan, fluorodeoxyglucose-positron emission tomography (FDG-PET), or sodium fluoride-positron emission tomography (NaF PET) scan. In certain of these embodiments, the subject is selected as having a BRAF V600 (e.g., V600E) mutation.

In some embodiments, provided herein are methods of increasing the maximum tolerated dose (MTD) of encorafenib in a subject undergoing treatment for cancer with encorafenib, comprising administering encorafenib in combination with a MEK inhibitor to the subject. In certain of these embodiments, the maximum tolerated dose is greater than about 50 mg (e.g., greater than about 100 mg, greater than about 200 mg, greater than about 300 mg, greater than about 400 mg, greater than about 500 mg, greater than about 600 mg, or greater than about 700 mg, or greater than about 800 mg). In certain of these embodiments, the maximum tolerated dose is about 50 mg (e.g., about 100 mg, 200 mg, 300 mg, 400 mg, 500 mg, 600 mg, 700 mg, or 800 mg). In certain of these embodiments, the cancer is associated with a BRAF mutant V600E. In certain of these embodiments, the cancer is colorectal cancer (e.g., metastatic colorectal cancer). In certain of these embodiments, the MEK inhibitor is selected from the group consisting of binimetinib, trametinib, cobimetinib, selumetinib, and PD-325901 (e.g., binimetinib). In certain of these embodiments, the subject is selected as having a BRAF V600 (e.g., V600E) mutation.

In some embodiments, provided herein are methods of increasing the maximum tolerated dose (MTD) of encorafenib in a subject undergoing treatment for cancer with encorafenib, comprising administering encorafenib in combination with an EGFR inhibitor to the subject. In certain of these embodiments, the maximum tolerated dose is greater than about 50 mg (e.g., greater than about 100 mg, greater than about 200 mg, greater than about 300 mg, greater than about 400 mg, greater than about 500 mg, greater than about 600 mg, greater than about 700 mg, or greater than about 800 mg). In certain of these embodiments, the maximum tolerated dose is about 50 mg (e.g., about 100 mg, 200 mg, 300 mg, 400 mg, 500 mg, 600 mg, 700 mg, or 800 mg). In certain of these embodiments, the cancer is associated with a BRAF mutant V600E. In certain of these embodiments, the cancer is colorectal cancer (e.g., metastatic colorectal cancer). In certain of these embodiments, the EGFR inhibitor is selected from the group consisting of cetuximab, gefitinib, erlotinib, lapatinib, dacomitinib, neratinib, vanetanib, and panitumumab (e.g., cetuximab). In certain of these embodiments, the subject is selected as having a BRAF V600 (e.g., V600E) mutation.

In some embodiments, provided herein are methods of increasing the maximum tolerated dose (MTD) of encorafenib in a subject undergoing treatment for cancer with encorafenib, comprising administering encorafenib in combination with a MEK inhibitor and an EGFR inhibitor to the subject. In certain of these embodiments, the maximum tolerated dose is greater than about 50 mg (e.g., greater than about 100 mg, greater than about 200 mg, greater than about 300 mg, greater than about 400 mg, greater than about 500 mg, greater than about 600 mg, greater than about 700 mg, or greater than about 800 mg). In certain of these embodiments, the maximum tolerated dose is about 50 mg (e.g., about 100 mg, 200 mg, 300 mg, 400 mg, 500 mg, 600 mg, 700 mg, or 800 mg). In certain of these embodiments, the cancer is associated with a BRAF mutant V600E. In certain of these embodiments, the cancer is colorectal cancer (e.g., metastatic colorectal cancer). In certain of these embodiments, the MEK inhibitor is selected from the group consisting of binimetinib, trametinib, cobimetinib, selumetinib, and PD-325901 (e.g., binimetinib). In certain of these embodiments, the EGFR inhibitor is selected from the group consisting of cetuximab, gefitinib, erlotinib, lapatinib, dacomitinib, neratinib, vanetanib, and panitumumab (e.g., cetuximab). In certain of these embodiments, the subject is selected as having a BRAF V600 (e.g., V600E) mutation.

In some embodiments, provided herein are methods of increasing the safe dosage of a combination of binimetinib and cetuximab in a subject, comprising administering encorafenib in conjunction with the binimetinib and cetuximab. In certain of these embodiments, the increase in safe dosage of binimetinib and/or cetuximab is each independently at least about 2% (e.g., at least about 4%, at least about 5%, at least about 6%, at least about 8%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100%. In certain of these embodiments, the subject is selected as having a BRAF V600 (e.g., V600E) mutation.

In some embodiments, provided herein are methods of increasing the safe dosage of a combination of encorafenib and cetuximab in a subject, comprising administering binimetinib in conjunction with the encorafenib and cetuximab. In certain of these embodiments, the increase in safe dosage of encorafenib and/or cetuximab is each independently at least about 2% (e.g., at least about 4%, at least about 5%, at least about 6%, at least about 8%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100%. In certain of these embodiments, the subject is selected as having a BRAF V600 (e.g., V600E) mutation.

In some embodiments, provided herein are methods of increasing the safe dosage of a combination of encorafenib and binimetinib in a subject, comprising administering cetuximab in conjunction with the encorafenib and binimetinib. In certain of these embodiments, the increase in safe dosage of encorafenib and/or binimetinib is each independently at least about 2% (e.g., at least about 4%, at least about 5%, at least about 6%, at least about 8%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100%. In certain of these embodiments, the subject is selected as having a BRAF V600 (e.g., V600E) mutation.

In some embodiments, provided herein are methods of inhibiting the MAPK signaling in a subject to whom a combination of encorafenib and cetuximab was administered, comprising administering binimetinib to the subject. In certain of these embodiments, the subject is selected as having a BRAF V600 (e.g., V600E) mutation.

In some embodiments, provided herein are methods of suppressing activation of EGFR in a subject to whom a combination of encorafenib and binimetinib was administered, comprising administering an anti-EGFR antibody (e.g., cetuximab, gefitinib, erlotinib, lapatinib, dacomitinib, neratinib, vanetanib, or panitumumab). In certain of these embodiments, the subject is selected as having a BRAF V600 (e.g., V600E) mutation.

In some embodiments, provided herein are methods of inhibiting a B-Raf kinase (e.g., mutant V600E) in a subject, comprising administering a therapeutically effective amount of binimetinib or a pharmaceutically acceptable salt thereof, cetuximab or a pharmaceutically acceptable salt thereof, and encorafenib or a pharmaceutically acceptable salt thereof. In certain of these embodiments, the B-Raf protein is encoded by a mutated BRAF. In certain of these embodiments, the BRAF includes a mutation in the kinase domain. In certain of these embodiments, the BRAF includes a V600 (e.g., V600E, V600K, or V600G) mutation.

In some embodiments, provided herein are methods of reducing activation of a Raf-MEK-ERK pathway in a subject, comprising administering a therapeutically effective amount of binimetinib or a pharmaceutically acceptable salt thereof, cetuximab or a pharmaceutically acceptable salt thereof, and encorafenib or a pharmaceutically acceptable salt thereof to the subject. In certain of these embodiments, the subject is selected as having a BRAF V600 (e.g., V600E) mutation.

In some embodiments, provided herein are methods of reducing activation of a Raf-MEK-ERK pathway in a subject undergoing a regimen of cetuximab and encorafenib, comprising administering binimetinib to the subject. In certain of these embodiments, the activation is associated with elevated kinase activity towards MEK. In certain of these embodiments, the activation is associated with activation of C-Raf. In certain of these embodiments, the subject has a B-Raf-associated cancer. In certain of these embodiments, the subject has colorectal cancer (e.g., metastatic colorectal cancer). In certain of these embodiments, the administering alleviates one or more symptoms of the colorectal cancer (e.g., metastatic colorectal cancer), elicits a positive response (e.g., partial or complete), and/or reduces tumor size and/or the number of cancer cells in the subject.

In some embodiments, provided herein are methods of increasing the B-Raf inhibition efficacy of encorafenib in a subject, comprising administering binimetinib and cetuximab in combination with encorafenib. In certain of these embodiments, the subject is selected as having a BRAF V600 (e.g., V600E) mutation.

In some embodiments, provided herein are methods of inhibiting the MAPK inhibition efficacy of encorafenib and cetuximab in a subject, comprising administering binimetinib in combination with encorafenib. In certain of these embodiments, the subject is selected as having a BRAF V600 (e.g., V600E) mutation.

In some embodiments, provided herein are methods of treating colorectal cancer (e.g., metastatic colorectal cancer) that has progressed after an initial cancer treatment in a subject, comprising administering a combination of encorafenib, cetuximab, and binimetinib to the subject. In certain of these embodiments, the initial cancer treatment produced a partial positive response. In certain of these embodiments, the initial cancer treatment produced no response. In certain of these embodiments, the initial cancer treatment comprised chemotherapy. In certain of these embodiments, the initial cancer treatment comprised administration of one or more therapeutic agents. In certain of these embodiments, the one or more therapeutic agents were administered as a combination. In certain of these embodiments, the one or more therapeutic agents are selected from the group consisting of cetuximab, bevacizumab, aflibercept, panitumumab, irinotecan, lecuovorin, and fluorouracil. In certain of these embodiments, the initial cancer treatment comprises administering irinotecan concurrently with folinic acid, followed by administration of fluorouracil as an intravenous bolus, followed by administration of fluorouracil by intravenous infusion. In certain of these embodiments, the irinotecan is administered at about 180 mg/m$^2$ over about 90 minutes. In certain of these embodiments, the folinic acid is administered at about 400 mg/m² (or 2×250 mg/m²) over about 120 minutes. In certain of these embodiments, the fluorouracil intravenous bolus is administered at between about 400 mg/m² to 500 mg/m². In certain of these embodiments, the fluorouracil intravenous infusion is administered at between about 2400 mg/m² to 3000 mg/m². In certain of these embodiments, the colorectal cancer (e.g., metastatic colorectal cancer) is associated with a BRAF V600E mutation.

In some embodiments, provided herein are methods of treating colorectal cancer (e.g., metastatic colorectal cancer) that has progressed after an initial cancer treatment in a subject, comprising independently administering therapeutically effective doses of encorafenib, cetuximab, and binimetinib to the subject. In certain of these embodiments, the initial cancer treatment produced a partial positive response. In certain of these embodiments, the initial cancer treatment produced no response. In certain of these embodiments, the initial cancer treatment comprised chemotherapy. In certain of these embodiments, the initial cancer treatment comprised administration of one or more therapeutic agents. In certain of these embodiments, the one or more therapeutic agents were administered as a combination. In certain of these embodiments, the one or more therapeutic agents are selected from the group consisting of cetuximab, bevacizumab, aflibercept, panitumumab, irinotecan, lecuovorin, and fluorouracil. In certain of these embodiments, the initial cancer treatment comprises administering irinotecan concurrently with folinic acid, followed by administration of fluorouracil as an intravenous bolus, followed by administration of fluorouracil by intravenous infusion. In certain of these embodiments, the irinotecan is administered at about 180 mg/m² over about 90 minutes. In certain of these embodiments, the folinic acid is administered at about 400 mg/m² (or 2×250 mg/m²) over about 120 minutes. In certain of these embodiments, the fluorouracil intravenous bolus is administered at between about 400 mg/m² to 500 mg/m². In certain of these embodiments, the fluorouracil intravenous infusion is administered at between about 2400 mg/m² to 3000 mg/m². In certain of these embodiments, the colorectal cancer (e.g., metastatic colorectal cancer) is associated with a BRAF V600E mutation.

In some embodiments, provided herein are methods of treating cancer in a subject, comprising administering a combination of encorafenib, binimetinib, and cetuximab; wherein the encorafenib and binimetinib are each administered at least 30 minutes prior to administration of the cetuximab. In certain of these embodiments, the encorafenib and binimetinib are administered in the morning. In certain of these embodiments, the binimetinib is administered in the evening. In certain of these embodiments, the subject has not consumed food (e.g., solid or liquid) one or more (e.g., two or more, three or more, four or more, five or more, or 6 or more) hours prior to the administration of the binimetinib. In certain of these embodiments, the encorafenib is administered once daily. In certain of these embodiments, the encorafenib is administered at the same time on each day it is administered. In certain of these embodiments, the dose of encorafenib administered is about 100 mg to about 400 mg (e.g., about 120 mg, about 150 mg, about 175 mg, about 200 mg, about 225 mg, about 250 mg, about 275 mg, about 300 mg, about 325 mg, about 350 mg, about 375 mg, or about 400 mg). In certain of these embodiments, encorafenib is administered orally. In certain of these embodiments, the binimetinib is administered twice daily. In certain of these embodiments, the binimetinib is administered at the same two times of the day on each day it is administered. In certain of these embodiments, the dose of binimetinib administered is about 10 mg to about 85 mg (e.g., about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, or about 85 mg). In certain of these embodiments, binimetinib is administered orally. In certain of these embodiments, the cetuximab is administered once weekly. In certain of these embodiments, the dose of cetuximab administered is about 150 mg to about 500 mg (e.g., about 175 mg, about 200 mg, about 225 mg, about 250 mg, about 275 mg, about 300 mg, about 325 mg, about 350 mg, about 375 mg, about 400 mg, about 425 mg, about 450 mg, or about 475 mg) if it is the first dose, or about 100 mg to about 350 mg (e.g., about 125 mg, about 150 mg, about 175 mg, about 200 mg, about 225 mg, about 250 mg, about 275 mg, about 300 mg, or about 325 mg) if it is not the first dose. In certain of these embodiments, the cetuximab is administered by intravenous infusion for a duration of between about 30 minutes to about 180 minutes (e.g., 40 minutes, 50 minutes, 60 minutes, 70 minutes, 80 minutes, 90 minutes, 100 minutes, 110 minutes, 120 minutes, 130 minutes, 140 minutes, 150 minutes, 160 minutes, or 170 minutes). In certain of these embodiments, the subject is instructed to avoid consumption of grapefruit, pomegranates, star fruits, or Seville oranges. In certain of these embodiments, the subject is selected as having a BRAF V600 (e.g., V600E) mutation.

DETAILED DESCRIPTION OF THE INVENTION

Figure 1A:
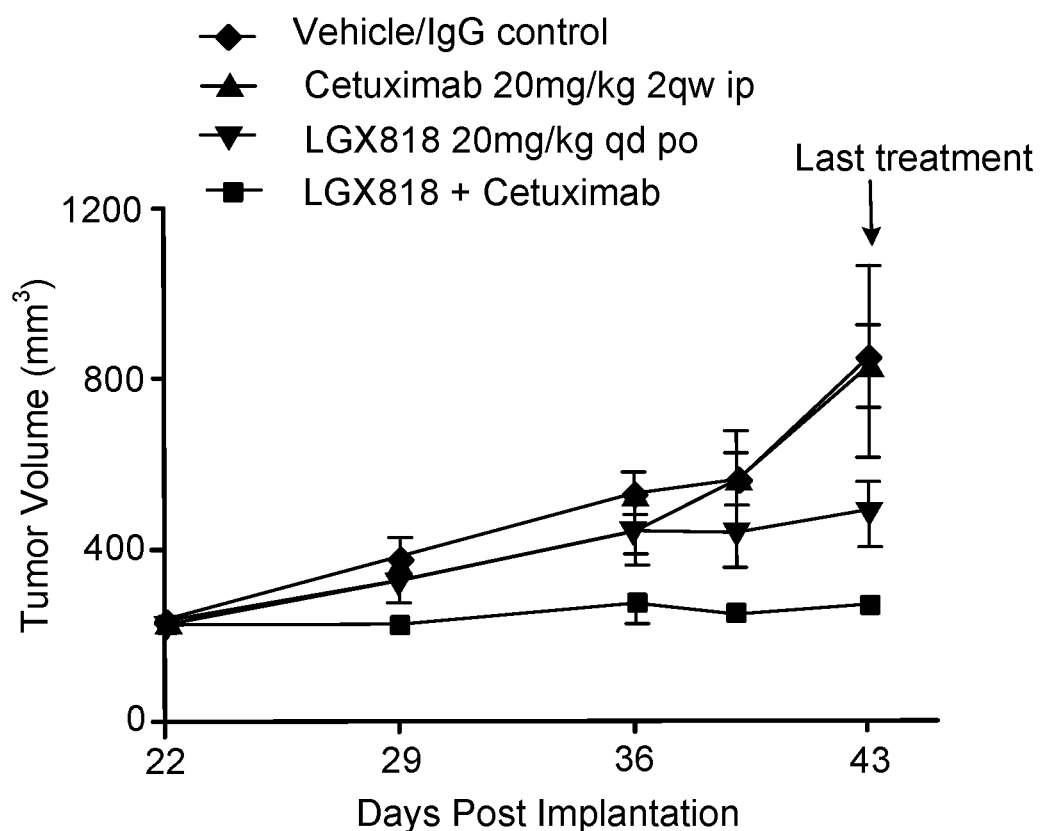
FIG. 1A is a tumor growth curve in a HT29 xenograft model following 21 days of vehicle (IgG control), cetuximab, LGX818, and LGX818+cetuximab treatment, presented as tumor volume (mm³) vs. days post implantation, where the closed diamond represent vehicle (IgG control), the closed triangle represents cetuximab, the closed inverted triangle represents LGX818, and the closed square represents LGX818+cetuximab.
Figure 1B:
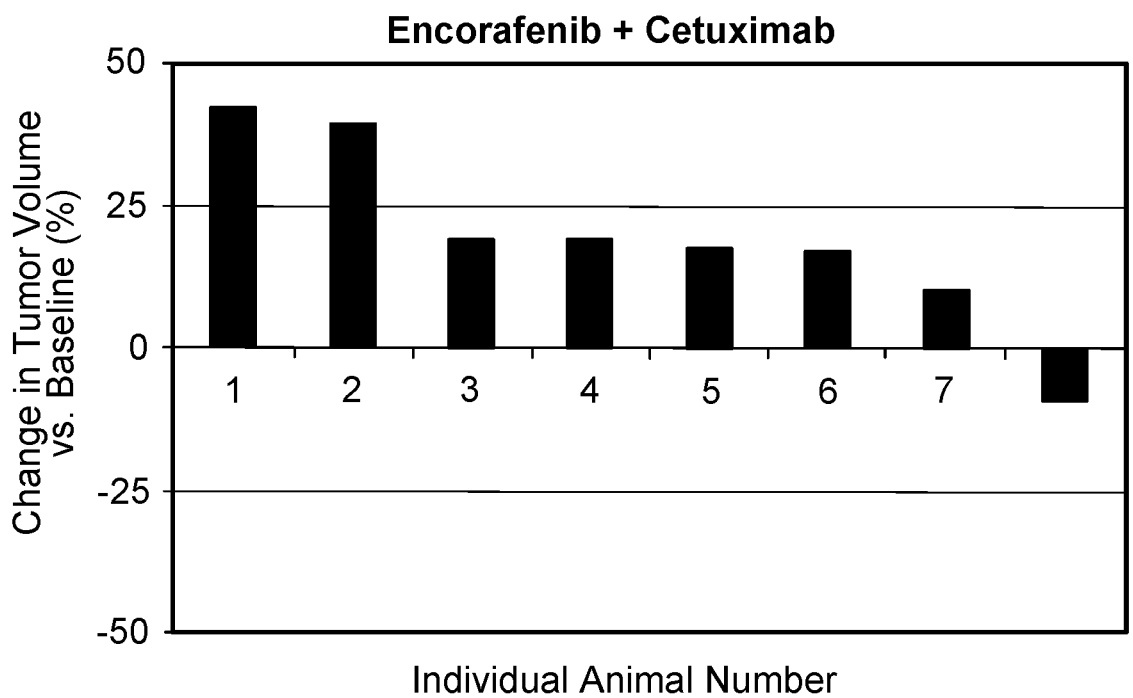
FIG. 1B is a waterfall plot showing individual animal response (tumor regression) to LGX818+cetuximab. The waterfall plot reflects the best response at any time point in the animals.
Figure 1C:
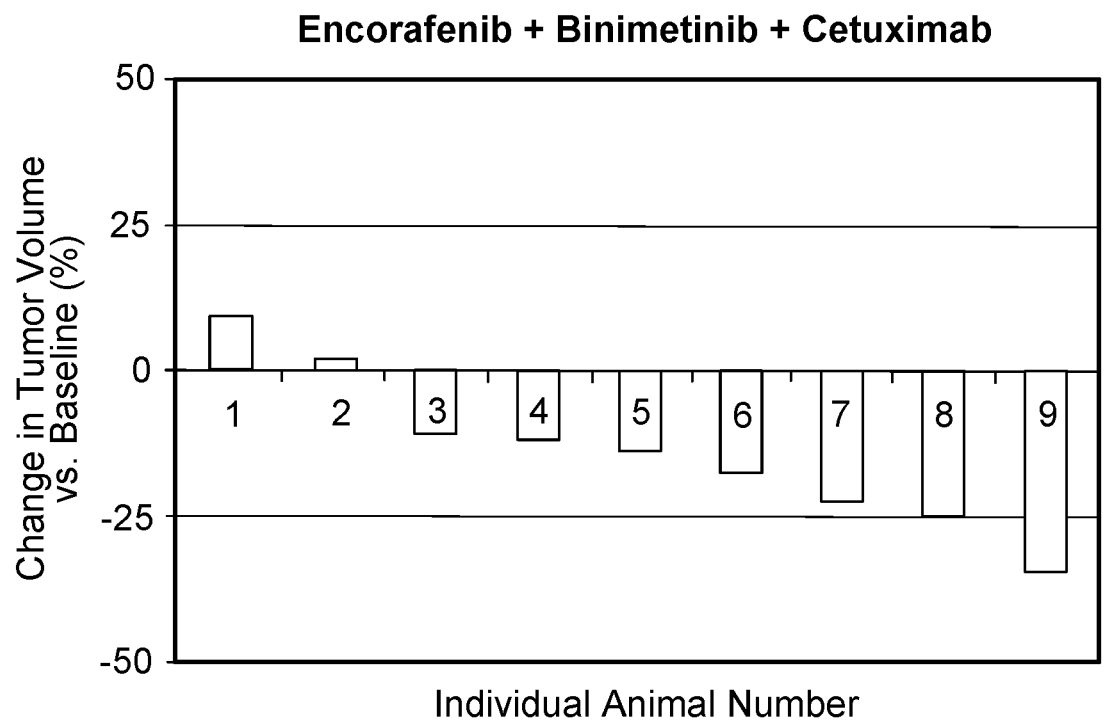
FIG. 1C is a waterfall plot showing individual animal response (tumor regression) to LGX818+cetuximab+binimetinib. The waterfall plot reflects the best response at any time point in the animals.

The present invention provides pharmaceutical combinations comprising therapeutically effective amounts, independently, of: (a) a BRAF inhibitor, or a pharmaceutically acceptable salt thereof, (b) at least one mitogen activated protein kinase (MEK) inhibitor, or a pharmaceutically acceptable salt thereof, and (c) an epidermal growth factor receptor (EGFR) inhibitor or a pharmaceutically acceptable salt thereof; and optionally at least one pharmaceutically acceptable carrier, for use in the treatment of a proliferative disease.

In one embodiment, provided herein is a pharmaceutical combination comprising therapeutically effective amounts, independently, of: (a) a BRAF inhibitor which is methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate (COMPOUND A) or a pharmaceutically acceptable salt thereof, (b) at least one MEK inhibitor (COMPOUND B), and (c) an anti-EGFR antibody (COMPOUND C), and optionally at least one pharmaceutically acceptable carrier, for use in the treatment of a proliferative disease.

In one embodiment, provided herein is a pharmaceutical combination comprising therapeutically effective amounts, independently, of: (a) a BRAF inhibitor which is methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate (COMPOUND A) or a pharmaceutically acceptable salt thereof, (b) a MEK inhibitor (COMPOUND B) which is 6-(4-bromo-2-fluorophenylamino)-7-fluoro-3-methyl-3H-benzoimidazole-5-carboxylic acid (2-hydroxyethoxy)-amide or a pharmaceutically acceptable salt thereof, and (c) an anti-EGFR antibody (COMPOUND C), and optionally at least one pharmaceutically acceptable carrier.

In one embodiment, provided herein is a pharmaceutical combination comprising therapeutically effective amounts, independently, of: (a) a BRAF inhibitor which is methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate (COMPOUND A) or a pharmaceutically acceptable salt thereof, (b) a MEK inhibitor (COMPOUND B) which is 6-(4-bromo-2-fluorophenylamino)-7-fluoro-3-methyl-3H-benzoimidazole-5-carboxylic acid (2-hydroxyethoxy)-amide or a pharmaceutically acceptable salt thereof, and (c) an anti-EGFR antibody (COMPOUND C) which is cetuximab, and optionally at least one pharmaceutically acceptable carrier.

Pharmaceutical combinations of the present invention include a BRAF inhibitor which is methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate (referred to herein as "COMPOUND A"). COMPOUND A is a compound of Formula I

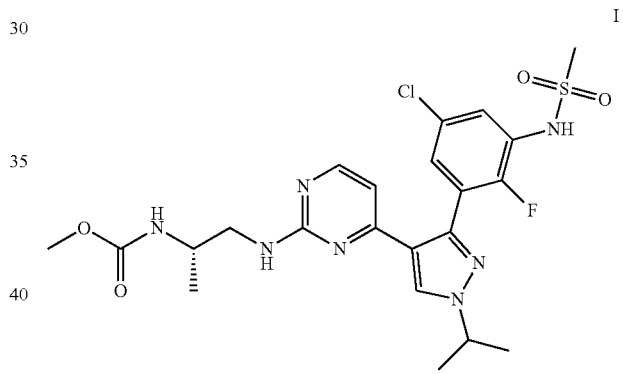

COMPOUND A is also known as Methyl [(2S)-1-{[4-(3-{5-chloro-2-fluoro-3-[(methylsulfonyl)amino]phenyl}-1-isopropyl-1H-pyrazol-4-yl)-2-pyrimidinyl]amino}-2-propanyl]carbamate, Methyl N-{(2S)-1-[(4-{3-[5-chloro-2-fluoro-3-(methanesulfonamido)phenyl]-1-(propan-2-yl)-1H-pyrazol-4-yl}pyrimidin-2-yl)amino]propan-2-yl}carbamate, LGX818, NVP-LGX818, and encorafenib. COMPOUND A is described in WO 2011/025927 and U.S. Pat. No. 8,501,758. The synthesis of COMPOUND A is described at Examples 5 and 6 of WO 2011/025927, which is hereby incorporated by reference in its entirety. In one embodiment, COMPOUND A is in the amorphous form.

When referring to COMPOUND A, the term "salt" or "salts" is understood to be a salt of COMPOUND A that can be present alone or in mixture with the free compound of Formula (I) and are preferably pharmaceutically acceptable salts. Such salts are formed, for example, as acid addition salts by reacting the free base form of COMPOUND A with a pharmaceutically acceptable inorganic or organic acid. The salts of COMPOUND A are preferably pharmaceutically acceptable salts.

COMPOUND A possesses an asymmetric center and can be produced as individual (R)- or (S)-stereoisomers or as mixtures thereof as described in WO 2011/025927. Except as otherwise indicated, the description or naming of COMPOUND A in the specification and claims is intended to include both individual enantiomers, and racemic mixtures thereof. Accordingly, this invention also includes all such isomers, including diastereomeric mixtures and resolved enantiomers of COMPOUND A. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. The methods for the determination of stereochemistry and the separation of stereoisomers are well known in the art (see discussion in Chapter 4 of "Advanced Organic Chemistry", $4^{th}$ edition, J. March. John Wiley and Sons, New York, 1992). In one embodiment, COMPOUND A is the (S)-stereoisomer, that is, Methyl [(2S)-1-{[4-(3-{5-chloro-2-fluoro-3-[(methylsulfonyl)amino]phenyl}-1-isopropyl-1H-pyrazol-4-yl)-2-pyrimidinyl]amino}-2-propanyl]carbamate.

Pharmaceutical combinations of the present invention include at least one MEK inhibitor (referred to herein as "COMPOUND B"). In one embodiment, the MEK inhibitor is selected from 6-(4-bromo-2-fluorophenylamino)-7-fluoro-3-methyl-3H-benzoimidazole-5-carboxylic acid (2-hydroxyethoxy)-amide, trametinib, cometinib (GDC-0973), and selumetinib (AZD6244). In one embodiment, COMPOUND B is 6-(4-bromo-2-fluorophenylamino)-7-fluoro-3-methyl-3H-benzoimidazole-5-carboxylic acid (2-hydroxyethoxy)-amide, which is a compound of formula (II)

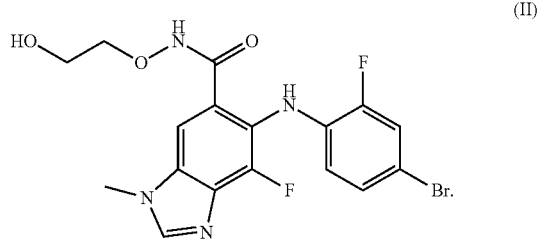 [SMILES: Cn1cnc2c(F)c(Nc3ccc(Br)cc3F)c(C(=O)NOCCO)cc21]

(II)

The MEK inhibitor 6-(4-bromo-2-fluorophenylamino)-7-fluoro-3-methyl-3H-benzoimidazole-5-carboxylic acid (2-hydroxyethoxy)-amide is described in PCT Publication No. WO 03/077914, which describes methods for its preparation, for example, in Example 18 (compound 29111). 6-(4-Bromo-2-fluorophenylamino)-7-fluoro-3-methyl-3H-benzoimidazole-5-carboxylic acid (2-hydroxyethoxy)-amide is also known as 5-[(4-bromo-2-fluorophenyl)amino]-4-fluoro-N-(2-hydroxyethoxy)-1-methyl-1H-benzimidazole-6-carboxamide, ARRY-162, MEK162, and binimetinib. In one embodiment, 6-(4-bromo-2-fluorophenylamino)-7-fluoro-3-methyl-3H-benzoimidazole-5-carboxylic acid (2-hydroxyethoxy)-amide is crystallized 6-(4-bromo-2-fluorophenylamino)-7-fluoro-3-methyl-3H-benzoimidazole-5-carboxylic acid (2-hydroxyethoxy)-amide. Crystallized 6-(4-bromo-2-fluorophenylamino)-7-fluoro-3-methyl-3H-benzoimidazole-5-carboxylic acid (2-hydroxyethoxy)-amide and methods of preparing crystallized 6-(4-bromo-2-fluorophenylamino)-7-fluoro-3-methyl-3H-benzoimidazole-5-carboxylic acid (2-hydroxyethoxy)-amide are described in PCT Publication No. WO 2014/063024, which is incorporated herein by reference.

In one embodiment, the MEK inhibitor is crystallized 6-(4-bromo-2-fluorophenylamino)-7-fluoro-3-methyl-3H-benzoimidazole-5-carboxylic acid (2-hydroxyethoxy)-amide. In one embodiment, crystallized 6-(4-bromo-2-fluorophenylamino)-7-fluoro-3-methyl-3H-benzoimidazole-5-carboxylic acid (2-hydroxyethoxy)-amide may be prepared according to Example 3. An X-ray powder diffraction pattern of crystallized 6-(4-bromo-2-fluorophenylamino)-7-fluoro-3-methyl-3H-benzoimidazole-5-carboxylic acid (2-hydroxyethoxy)-amide has characteristic diffraction peaks expressed in degrees 2theta (2θ). X-ray powder diffraction (XRPD) analysis was performed using a Shimadzu XRD-6000 X-ray powder diffractometer using Cu Kα radiation. The instrument is equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by NAI scintillation detector. A θ-2θ continuous scan at 1°/min (step size 0.02°) from 2 to 42' 2θ was used (Cnt. Time=1.200 seconds; wavelength=1.540562; number of points=2001; data file resolution=1600). Diffractometer optics: fixed slit; no X2 configuration. Tube: fixed slit; no X2 configuration. A silicon standard was analyzed to check the instrument alignment. Data were collected and analyzed using XRD-6100/7000 v.5.0. Samples were prepared for analysis by placing them in a stainless steel sample holder.

In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 20.38. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 28.39. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 11.18. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 29.18. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 22.43. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 22.75. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 25.23. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 16.05. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 11.82. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 23.74. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 16.33. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 19.00.

In some embodiments, crystallized 6-(4-bromo-2-fluorophenylamino)-7-fluoro-3-methyl-3H-benzoimidazole-5-carboxylic acid (2-hydroxyethoxy)-amide has an X-ray powder diffraction pattern comprising 2 to 12 of the following characteristic peaks expressed in degrees 2θ at 20.38, 28.39, 11.18, 29.18, 22.43, 22.75, 25.23, 16.05, 11.82, 23.74, 16.33, and 19.00. For example, crystallized 6-(4-bromo-2-fluorophenylamino)-7-fluoro-3-methyl-3H-benzoimidazole-5-carboxylic acid (2-hydroxyethoxy)-amide can have an X-ray powder diffraction pattern comprising characteristic peaks expressed in degrees 2θ at 20.38 or 28.39; or an X-ray powder diffraction pattern comprising characteristic peaks expressed in degrees 2θ at 20.38, 28.39, and 11.18; or an X-ray powder diffraction pattern comprising characteristic peaks expressed in degrees 2θ at 20.38, 28.39, 11.18, and 29.18; or an X-ray powder diffraction pattern comprising characteristic peaks expressed in degrees 2θ at 20.38, 28.39, 11.18, 29.18, 22.43, and 22.75; or an X-ray powder diffraction pattern comprising characteristic peaks expressed in degrees 2θ at 20.38, 28.39, 11.18, 29.18, 22.43, 22.75, 25.23, 16.05, and 11.82; or an X-ray powder diffraction pattern comprising characteristic peaks expressed in degrees 2θ at 20.38, 28.39, 11.18, 29.18, 22.43, 22.75, 25.23, 16.05, 11.82, 23.74, 16.33, and 19.00.

In certain embodiments, crystallized 6-(4-bromo-2-fluorophenylamino)-7-fluoro-3-methyl-3H-benzoimidazole-5-carboxylic acid (2-hydroxyethoxy)-amide has an X-ray powder diffraction pattern comprising characteristic peaks expressed in degrees 2θ at 20.38, 28.39, 11.18, 29.18, 22.43, 22.75, 25.23, 16.05, 11.82, 23.74, 16.33, 19.00, 30.01, 25.98, 37.35, 6.79, 9.47, 34.21, 30.43, and 31.40

In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 20.4±0.2. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 28.4±0.2. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 11.2±0.2. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 29.2±0.2. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 22.4±0.2. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 22.7±0.2. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 25.2±0.2. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 16.0±0.2. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 11.8±0.2. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 23.7±0.2. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 16.3±0.2. In some embodiments, crystallized 6-(4-bromo-2-fluorophenylamino)-7-fluoro-3-methyl-3H-benzoimidazole-5-carboxylic acid (2-hydroxyethoxy)-amide has a characteristic peak expressed in degrees 2θ at 19.0±0.2.

In some embodiments, crystallized 6-(4-bromo-2-fluorophenylamino)-7-fluoro-3-methyl-3H-benzoimidazole-5-carboxylic acid (2-hydroxyethoxy)-amide has an X-ray powder diffraction pattern comprising 2 to 12 of the following characteristic peaks expressed in degrees 2θ at 20.4±0.2, 28.4±0.2, 11.2±0.2, 29.2±0.2, 22.4±0.2, 22.7±0.2, 25.2±0.2, 16.0±0.2, 11.8±0.2, 23.7±0.2, 16.3±0.2, and 19.0±0.2. For example, crystallized 6-(4-bromo-2-fluorophenylamino)-7-fluoro-3-methyl-3H-benzoimidazole-5-carboxylic acid (2-hydroxyethoxy)-amide can have an X-ray powder diffraction pattern comprising characteristic peaks expressed in degrees 2θ at 20.4±0.2 and 28.4±0.2; or an X-ray powder diffraction pattern comprising characteristic peaks expressed in degrees 2θ at 20.4±0.2, 28.4±0.2, and 11.2±0.2; or an X-ray powder diffraction pattern comprising characteristic peaks expressed in degrees 2θ at 20.4±0.2, 28.4±0.2, 11.2±0.2, and 29.2±0.2; or an X-ray powder diffraction pattern comprising characteristic peaks expressed in degrees 2θ at 20.4±0.2, 28.4±0.2, 11.2±0.2, 29.2±0.2, 22.4±0.2, and 22.7±0.2; or an X-ray powder diffraction pattern comprising characteristic peaks expressed in degrees 2θ at 20.4±0.2, 28.4±0.2, 11.2±0.2, 29.2±0.2, 22.4±0.2, 22.7±0.2, 25.2±0.2, 16.0±0.2, and 11.8±0.2; or an X-ray powder diffraction pattern comprising characteristic peaks expressed in degrees 2θ at 20.4±0.2, 28.4±0.2, 11.2±0.2, 29.2±0.2, 22.4±0.2, 22.7±0.2, 25.2±0.2, 16.0±0.2, 11.8±0.2, 23.7±0.2, 16.3±0.2, and 19.0±0.2.

In certain embodiments, crystallized 6-(4-bromo-2-fluorophenylamino)-7-fluoro-3-methyl-3H-benzoimidazole-5-carboxylic acid (2-hydroxyethoxy)-amide has an X-ray powder diffraction pattern comprising characteristic peaks expressed in degrees 2θ at 20.4±0.2, 28.4±0.2, 11.2±0.2, 29.2±0.2, 22.4±0.2, 22.7±0.2, 25.2±0.2, 16.0±0.2, 11.8±0.2, 23.7±0.2, 16.3±0.2, 19.0±0.2, 30.0±0.2, 26.0±0.2, 37.3±0.2, 6.8±0.2, 9.5±0.2, 34.2±0.2, 30.4±0.2, and 31.4±0.2.

In some embodiments, crystallized 6-(4-bromo-2-fluorophenylamino)-7-fluoro-3-methyl-3H-benzoimidazole-5-carboxylic acid (2-hydroxyethoxy)-amide has an X-ray powder diffraction pattern with at least the 20 characteristic peaks (degrees 2θ) as listed in Table A.

TABLE A

XRPD peaks of crystallized 6-(4-bromo-2-fluorophenylamino)-7-fluoro-3-methyl-3H-benzoimidazole-5-carboxylic acid (2-hydroxyethoxy)-amide

| Peak Position | Relative Intensity |
| --- | --- |
| 20.3800 | 100.00 |
| 28.3913 | 79.16 |
| 11.1794 | 37.28 |

TABLE A-continued

XRPD peaks of crystallized 6-(4-bromo-2-fluorophenylamino)-
7-fluoro-3-methyl-3H-benzoimidazole-5-carboxylic
acid (2-hydroxyethoxy)-amide

| Peak Position | Relative Intensity |
|---|---|
| 29.1781 | 20.08 |
| 22.4263 | 19.60 |
| 22.7475 | 19.25 |
| 25.2388 | 18.65 |
| 16.0469 | 17.88 |
| 11.8200 | 17.53 |
| 23.7469 | 15.95 |
| 16.3331 | 14.72 |
| 18.9975 | 14.54 |
| 30.0125 | 11.60 |
| 25.9825 | 11.26 |
| 37.3462 | 10.86 |
| 6.7937 | 9.80 |
| 9.4694 | 9.10 |
| 34.2062 | 8.05 |
| 30.4287 | 7.67 |
| 31.4044 | 6.04 |

As related to COMPOUND B, the term "salt" or "salts", unless otherwise indicated, includes salts of acidic and basic groups which may be present in the compounds of the present invention. COMPOUND B is capable of forming salts with various inorganic and organic acids. The acids that may be used to prepare pharmaceutically acceptable acid addition salts of such basic compounds of the present invention are those that form non-toxic acid addition salts, i.e., salts containing pharmaceutically acceptable anions, such as the acetate, benzoate, bromide, chloride, citrate, fumarate, hydrobromide, hydrochloride, iodide, lactate, maleate, mandelate, nitrate, oxalate, salicylate, succinate, and tartrate salts. An example of a salt of this type is a hydrochloride or sulfate salt of COMPOUND B of the present invention.

Additional pharmaceutically acceptable salts of COMPOUND B suitable for the present invention include the salts disclosed in PCT Application No. WO 03/077914, which is incorporated by reference herein.

Pharmaceutical combinations of the present invention include an epidermal growth factor receptor (EGFR) inhibitor (referred to herein as COMPOUND C). In one embodiment, the EGFR inhibitor is a tyrosine kinase inhibitor (for example, erlotinib, gefitinib, or lapatinib). In one embodiment, the EGFR inhibitor is a monoclonal antibody, also referred to herein as an anti-EGFR antibody (for example, panitumumab or cetuximab). The term "anti-EGFR antibody" is defined herein to refer to an antibody or an antigen binding fragment thereof able to bind to EGFR (i.e., an EGFR antagonist). The anti-EGFR antibody competes for the ligand receptor binding by occluding the ligand-binding region. The anti-EGFR antibody may promote receptor internalization and subsequent degradation without receptor phosphorylation. In one embodiment the anti-EGFR antibody recognizes the same epitope as the C225 (also known as cetuximab) described in WO 96/40210. In another embodiment the anti-EGFR antibody has the same 6 CDR's (complementarity-determining regions) as C225 (cetuximab) describe in WO 96/40210. In one embodiment, COMPOUND C is the anti-EGFR antibody cetuximab (also known as C225 and Erbitux®). Cetuximab is a monoclonal antibody, and its sequences, and methods for its preparation and use for treating proliferative diseases is disclosed in U.S. Pat. No. 6,217,866 and in WO 96/40210, which are here incorporated by reference. As a monoclonal antibody, the mode of action of cetuximab is distinct from standard non-selective chemotherapy treatments in that it specifically targets and binds to the EGFR. This binding inhibits the activation of the receptor and the subsequent signal-transduction pathway, which results in reducing both the invasion of normal tissues by tumor cells and the spread of tumors to new sites. It is also believed to inhibit the ability of tumor cells to repair the damage caused by chemotherapy and radiotherapy and to inhibit the formation of new blood vessels inside tumors, which appears to lead to an overall suppression of tumor growth.

Hereinafter, triple combinations of COMPOUND A, COMPOUND B and COMPOUND C will be referred to as a COMBINATION OF THE INVENTION, wherein each of COMPOUND A, COMPOUND B and COMPOUND C may be referred to as a combination partner, combination component, or therapeutic agent.

The present invention pertains to a COMBINATION OF THE INVENTION useful for separate, simultaneous or sequential administration of the combination components, to a patient in need thereof for treating a proliferative disease.

The present invention further provides a commercial package comprising as therapeutic agents a COMBINATION OF THE INVENTION, together with instructions for separate, simultaneous or sequential administration thereof for use in the treatment of a proliferative disease.

The present invention further provides a commercial package comprising as therapeutic agents COMPOUND A (methyl N-[(2S)-1-({4-[3-(5-chloro-2-fluoro-3-methane-sulfonamidophenyl)-1-(propan-2-yl)-1H-pyrazol-4-yl]pyrimidin-2-yl}amino)propan-2-yl]carbamate or a pharmaceutically acceptable salt thereof) and COMPOUND B, together with instructions for separate, simultaneous or sequential administration of COMPOUND A and COMPOUND B together with COMPOUND C. In one embodiment, the MEK inhibitor is 6-(4-bromo-2-fluorophenylamino)-7-fluoro-3-methyl-3H-benzoimidazole-5-carboxylic acid (2-hydroxyethoxy)-amide or a pharmaceutically acceptable salt thereof. In one embodiment, the anti-EGFR-inhibitor antibody is cetuximab.

The general terms used herein are defined with the following meanings, unless explicitly stated otherwise:

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "combination" or "pharmaceutical combination" is defined herein to refer to either a fixed combination in one dosage unit form, or a non-fixed combination or a kit of parts for the combined administration of a prescribed triple therapy treatment regimen, where the BRAF inhibitor, i.e., COMPOUND A, or a pharmaceutically acceptable salt thereof, a MEK inhibitor, i.e., COMPOUND B, or a pharmaceutically acceptable salt thereof, and the EGFR inhibitor, i.e., COMPOUND C, e.g., an anti-EGFR antibody, may be administered simultaneously or independently at the same time or separately within time intervals. In one embodiment, the combination partners (i.e., COMPOUND A, COMPOUND B and COMPOUND C) are administered simultaneously, independently at the same time, or separately, optionally within specific time intervals that allow that the combination partners to show a cooperative, e.g., synergistic, effect. The term "fixed combination" means that the combination partners COMPOUND A and COMPOUND B are both administered to a patient simultaneously in the form of a single entity or unit dosage form, while COMPOUND C is administered as a separate entity or unit dosage form. The term "non-fixed combination" means that COMPOUND A, or a pharmaceutically acceptable salt thereof, COMPOUND B, or a pharmaceutically acceptable salt thereof, and COMPOUND C are each administered to a patient as separate unit dosage forms, either simultaneously, separately or sequentially, optionally at specific time intervals, wherein such administration provides therapeutically effective levels of the three compounds in the body of the patient.

The term "pharmaceutical composition" is defined herein to refer to a mixture or solution containing at least one therapeutic agent (i.e., COMPOUND A, COMPOUND B or COMPOUND C) to be administered to a subject, e.g., a mammal or human, in order to treat a particular disease or condition affecting the mammal.

The term "pharmaceutically acceptable" is defined herein to refer to those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

The terms "co-administration" or "combined administration" as used herein is defined to encompass the administration of the selected therapeutic agents to a single patient, and are intended to include treatment regimens in which the agents are not necessarily administered by the same route of administration or at the same time.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease. "Treatment" can also mean prolonging survival as compared to expected survival if not receiving treatment, for example, an increase in overall survival (OS) compared to a subject not receiving treatment as described herein, and/or an increase in progression-free survival (PFS) compared to a subject not receiving treatment as described herein. The term "treating" can also mean an improvement in the condition of a subject having a cancer, e.g., one or more of a decrease in the size of one or more tumor(s) in a subject, a decrease or no substantial change in the growth rate of one or more tumor(s) in a subject, a decrease in metastasis in a subject, and an increase in the period of remission for a subject (e.g., as compared to the one or more metric(s) in a subject having a similar cancer receiving no treatment or a different treatment, or as compared to the one or more metric(s) in the same subject prior to treatment). Additional metrics for assessing response to a treatment in a subject having a cancer are disclosed herein below.

The term "jointly therapeutically active" or "joint therapeutic effect" as used herein means that the therapeutic agents of a COMBINATION OF THE INVENTION may be given to the patient simultaneously or separately (e.g., in a chronologically staggered manner, for example a sequence-specific manner) in such time intervals that they show an interaction (e.g., a joint therapeutic effect, for example a synergistic effect). Whether this is the case can, inter alia, be determined by following the blood levels and showing that the combination components are present in the blood of the human to be treated at least during certain time intervals.

The term "pharmaceutically effective amount" or "clinically effective amount" or "therapeutically effective amount" of a combination of therapeutic agents of a COMBINATION OF THE INVENTION is an amount sufficient to provide an observable improvement over the baseline clinically observable signs and symptoms of the disorder treated with the combination.

The terms "antibody" and "antibodies" are used interchangeably in the broadest sense and include monoclonal antibodies, isolated, engineered, chemically synthesized, or recombinant antibodies (e.g., full length or intact monoclonal antibodies), polyclonal antibodies, multivalent antibodies or multispecific antibodies (e.g., bispecific antibodies) and also antibody fragments, so long as they exhibit the desired biological activity. In one embodiment, the antibody is a recombinant antibody.

As used herein, the expression "EGFR antibody" should be interpreted as similar to "anti-EGFR antibody" and means an antibody capable of binding to EGFR.

By "EGFR binding fragment" or "antigen-binding fragment" of an antibody, it is intended to indicate any peptide, polypeptide, or protein retaining the ability to bind to the EGFR target (also generally referred as antigen) of the antibody. In an embodiment, such "antigen binding fragments" are selected in the group consisting of Fv, scFv (sc for single chain), Fab, F(ab')$_2$, Fab', scFv-Fc fragments or diabodies, or any fragment of which the half-life time would have been increased by chemical modification, such as the addition of poly(alkylene) glycol such as poly(ethylene) glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation into a liposome, said fragments having at least one of the characteristic CDRs of the antibody according to the invention. In one embodiment, the "antigen binding fragments" will be constituted or will comprise a partial sequence of the heavy or light variable chain of the antibody from which they are derived, said partial sequence being sufficient to retain the same specificity of binding as the antibody from which it is descended and a sufficient affinity, for example at least equal to $1/100$, as a further example to at least equal to $1/10$, of the affinity of the antibody from which it is descended, with respect to the target.

The term "BRAF inhibitor" as used herein refers to a compound which targets, decreases or inhibits the kinase activity of a BRAF protein, including mutant forms of BRAF protein, such as BRAF V600 mutations, such as V600E, V600D and V600K. In one embodiment, the mutant BRAF protein includes a V600E mutation.

The term "MEK inhibitor" as used herein refers to a compound which targets, decreases or inhibits the kinase activity of MAP kinase (MEK), including mutant forms of MEK. In one embodiment, the MEK inhibitor is selected from 6-(4-bromo-2-fluorophenylamino)-7-fluoro-3-methyl-3H-benzoimidazole-5-carboxylic acid (2-hydroxyethoxy)-amide (binimetinib; MEK162; ARRY-162), trametinib, cometinib (GDC-0973), and selumetinib (AZD6244). In one embodiment, the MEK inhibitor is 6-(4-bromo-2-fluorophenylamino)-7-fluoro-3-methyl-3H-benzoimidazole-5-carboxylic acid (2-hydroxyethoxy)-amide. In one embodiment, the MEK inhibitor is crystallized 6-(4-bromo-2-fluorophenylamino)-7-fluoro-3-methyl-3H-benzoimidazole-5-carboxylic acid (2-hydroxyethoxy)-amide.

The term "EGFR inhibitor" as used herein refers to a compound which targets, decreases or inhibits the EGFR activity, including mutant forms of EGFR, including (EGFRvIII). In one embodiment, the EGFR inhibitor is an anti-EGFR antibody.

The term "anti-EGFR antibody" as used herein refers to an antibody or an antigen binding fragment thereof able to bind to EGFR (i.e., an EGFR antagonist) which targets, decreases or inhibits the kinase activity of EGFR activity, including mutant forms of EGFR. In one embodiment, the anti-EGFR antibody is cetuximab, gefitinib, erlotinib, lapatinib, dacomitinib, neratinib, vanetanib, or panitumumab. In one embodiment, the anti-EGFR antibody is cetuximab.

As used herein, the terms "subject," "individual," or "patient," used interchangeably, refer to any animal, including mammals such as humans, primates, mice, rats, other rodents, rabbits, dogs, cats, swine, cattle, sheep and horses. In some embodiments, the subject is a human. In some embodiments, the subject has experienced and/or exhibited at least one symptom of the disease or disorder to be treated. In some embodiments, the subject has been identified or diagnosed as having a BRAF-associated disease or disorder. In some embodiments, the subject has been identified or diagnosed as having a cancer with dysregulation of a BRAF gene, a BRAF protein, or expression or activity, or level of the same (e.g., a BRAF-associated cancer) (e.g., as determined using a regulatory agency-approved, e.g., FDA-approved, assay or kit). In some embodiments, the subject has a tumor that is positive for dysregulation of a BRAF gene, a BRAF protein, or expression or activity, or level of the same (e.g., as determined using a regulatory agency-approved assay or kit). The subject can be a subject with a tumor(s) that is positive for dysregulation of a BRAF gene, a BRAF protein, or expression or activity, or level of the same (e.g., identified as positive using a regulatory agency-approved, e.g., FDA-approved, assay or kit). The subject can be a subject whose tumors have dysregulation of a BRAF gene, a BRAF protein, or expression or activity, or a level of the same (e.g., where the tumor is identified as such using a regulatory agency-approved, e.g., FDA-approved, kit or assay). In some embodiments, the subject is suspected of having a BRAF-associated cancer. In some embodiments, the subject has a clinical record indicating that the subject has a tumor that has dysregulation of a BRAF gene, a BRAF protein, or expression or activity, or level of the same (and optionally the clinical record indicates that the subject should be treated with any of the combinations provided herein). In some embodiments, the subject has been identified or diagnosed as having a MEK-associated disease or disorder. In some embodiments, the subject has been identified or diagnosed as having a cancer with dysregulation of a MEK gene, a MEK protein, or expression or activity, or level of the same (e.g., a MEK-associated cancer) (e.g., as determined using a regulatory agency-approved, e.g., FDA-approved, assay or kit). In some embodiments, the subject has a tumor that is positive for dysregulation of a MEK gene, a MEK protein, or expression or activity, or level of the same (e.g., as determined using a regulatory agency-approved assay or kit). The subject can be a subject with a tumor(s) that is positive for dysregulation of a MEK gene, a MEK protein, or expression or activity, or level of the same (e.g., identified as positive using a regulatory agency-approved, e.g., FDA-approved, assay or kit). The subject can be a subject whose tumors have dysregulation of a MEK gene, a MEK protein, or expression or activity, or a level of the same (e.g., where the tumor is identified as such using a regulatory agency-approved, e.g., FDA-approved, kit or assay). In some embodiments, the subject is suspected of having a MEK-associated cancer. In some embodiments, the subject has a clinical record indicating that the subject has a tumor that has dysregulation of a MEK gene, a MEK protein, or expression or activity, or level of the same (and optionally the clinical record indicates that the subject should be treated with any of the combinations provided herein). In some embodiments, the subject has been identified or diagnosed as having an EGFR-associated disease or disorder. In some embodiments, the subject has been identified or diagnosed as having a cancer with dysregulation of an EGFR gene, an EGFR protein, or expression or activity, or level of the same (e.g., an EGFR-associated cancer) (e.g., as determined using a regulatory agency-approved, e.g., FDA-approved, assay or kit). In some embodiments, the subject has a tumor that is positive for dysregulation of an EGFR gene, an EGFR protein, or expression or activity, or level of the same (e.g., as determined using a regulatory agency-approved assay or kit). The subject can be a subject with a tumor(s) that is positive for dysregulation of an EGFR gene, an EGFR protein, or expression or activity, or level of the same (e.g., identified as positive using a regulatory agency-approved, e.g., FDA-approved, assay or kit). The subject can be a subject whose tumors have dysregulation of an EGFR gene, an EGFR protein, or expression or activity, or a level of the same (e.g., where the tumor is identified as such using a regulatory agency-approved, e.g., FDA-approved, kit or assay). In some embodiments, the subject is suspected of having an EGFR-associated cancer. In some embodiments, the subject has a clinical record indicating that the subject has a tumor that has dysregulation of an EGFR gene, an EGFR protein, or expression or activity, or level of the same (and optionally the clinical record indicates that the subject should be treated with any of the combinations provided herein). In some embodiments, the subject is a pediatric patient. In one embodiment, the subject has colorectal cancer. In one embodiment, the subject has metastatic colorectal cancer. In one embodiment, the subject has metastatic colorectal cancer having a BRAF V600E mutation. In one embodiment, the subject has stage IV metastatic colorectal cancer having a BRAF V600E mutation.

The term "regulatory agency" is a country's agency for the approval of the medical use of pharmaceutical agents with the country. For example, a non-limiting example of a regulatory agency is the U.S. Food and Drug Administration (FDA).

The term "pediatric patient" as used herein refers to a patient under the age of 16 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. *Nelson Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994.

The term "BRAF-associated disease or disorder" as used herein refers to diseases or disorders associated with or having a dysregulation of a BRAF gene, a BRAF kinase (also called herein BRAF kinase protein or BRAF kinase), or the expression or activity or level of any (e.g., one or more) of the same (e.g., any of the types of dysregulation of a BRAF gene, a BRAF kinase, a BRAF kinase domain, or the expression or activity or level of any of the same described herein). Non-limiting examples of a BRAF-associated disease or disorder include, for example, BRAF-associated cancer.

The term "BRAF-associated cancer" as used herein refers to cancers associated with or having a dysregulation of a BRAF gene, a BRAF kinase (also called herein BRAF kinase protein or BRAF), or expression or activity, or level of the same. In one embodiment, the BRAF-associated cancer is a cancer having a BRAF V600 mutation. In one embodiment, the BRAF-associated cancer is a cancer having a BRAF V600E mutation. In one embodiment, the BRAF associated cancer is colorectal cancer. In one embodiment, the colorectal cancer is metastatic colorectal cancer. In one embodiment, the BRAF associated cancer is metastatic colorectal cancer having a BRAF V600E mutation. In one embodiment, the BRAF associated cancer is metastatic colorectal cancer having a BRAF V600 mutation.

The phrase "dysregulation of a BRAF gene, a BRAF kinase, or the expression or activity or level of the same" refers to a genetic mutation (e.g., a BRAF gene translocation that results in the expression of a fusion protein, a deletion in a BRAF gene that results in the expression of a BRAF protein that includes a deletion of at least one amino acid as compared to the wild-type BRAF protein, a mutation in a BRAF gene that results in the expression of a BRAF protein with one or more point mutations, or an alternative spliced version of a BRAF mRNA that results in a BRAF protein that results in the deletion of at least one amino acid in the BRAF protein as compared to the wild-type BRAF protein), a BRAF gene amplification that results in overexpression of a BRAF protein, or an autocrine activity resulting from the overexpression of a BRAF gene a cell, that results in a pathogenic increase in the activity of a kinase domain of a BRAF protein (e.g., a constitutively active kinase domain of a BRAF protein) in a cell. For example, a dysregulation of a BRAF gene, a BRAF protein, or expression or activity, or level of the same, can be a mutation in a BRAF gene that encodes a BRAF protein that is constitutively active or has increased activity as compared to a protein encoded by a BRAF gene that does not include the mutation. As another example, a dysregulation of a BRAF gene, a BRAF protein, or expression or activity, or level of the same, can be the result of a gene or chromosome translocation which results in the expression of a fusion protein that contains a first portion of BRAF that includes a functional kinase domain, and a second portion of a partner protein (i.e., that is not BRAF). In some examples, dysregulation of a BRAF gene, a BRAF protein, or expression or activity, can be a result of a gene translation of one BRAF gene with another BRAF gene. Examples of BRAF mutations include V600E, V600K and V600G mutations. In one embodiment the mutation is a BRAF V600E mutation.

The term "MEK-associated disease or disorder" as used herein refers to diseases or disorders associated with the Ras/Raf/MEK pathway, for example diseases or disorders associated with or having a dysregulation of a MEK gene, a MEK kinase (also called herein MEK kinase protein or MEK kinase), or the expression or activity or level of any (e.g., one or more) of the same (e.g., any of the types of dysregulation of a MEK gene, a MEK kinase, a MEK kinase domain, or the expression or activity or level of any of the same described herein). Non-limiting examples of a MEK-associated disease or disorder include, for example, cancer.

The term "MEK-associated cancer" as used herein refers to cancers associated with or having a dysregulation of a MEK gene, a MEK kinase (also called herein MEK kinase protein or MEK), or expression or activity, or level of the same. Non-limiting examples of a MEK-associated cancer are described herein. In one embodiment, the MEK-associated cancer is colorectal cancer. In one embodiment, the colorectal cancer is metastatic colorectal cancer.

The phrase "dysregulation of a MEK gene, a MEK kinase, or the expression or activity or level of the same" refers to a genetic mutation (e.g., a MEK gene translocation that results in the expression of a fusion protein, a deletion in a MEK gene that results in the expression of a MEK protein that includes a deletion of at least one amino acid as compared to the wild-type MEK protein, a mutation in a MEK gene that results in the expression of a MEK protein with one or more point mutations, or an alternative spliced version of a MEK mRNA that results in a MEK protein that results in the deletion of at least one amino acid in the MEK protein as compared to the wild-type MEK protein), a MEK gene amplification that results in overexpression of a MEK protein, or an autocrine activity resulting from the overexpression of a MEK gene a cell, that results in a pathogenic increase in the activity of a kinase domain of a MEK protein (e.g., a constitutively active kinase domain of a MEK protein) in a cell. For example, a dysregulation of a MEK gene, a MEK protein, or expression or activity, or level of the same, can be a mutation in a MEK gene that encodes a MEK protein that is constitutively active or has increased activity as compared to a protein encoded by a MEK gene that does not include the mutation. As another example, a dysregulation of a MEK gene, a MEK protein, or expression or activity, or level of the same, can be the result of a gene or chromosome translocation which results in the expression of a fusion protein that contains a first portion of MEK that includes a functional kinase domain, and a second portion of a partner protein (i.e., that is not MEK). In some examples, dysregulation of a MEK gene, a MEK protein, or expression or activity, can be a result of a gene translation of one MEK gene with another MEK gene.

The term "EGFR-associated disease or disorder" as used herein refers to diseases or disorders associated with or having a dysregulation of an EGFR gene, an EGFR kinase (also called herein EGFR kinase protein or EGFR kinase), or the expression or activity or level of any (e.g., one or more) of the same (e.g., any of the types of dysregulation of an EGFR gene, an EGFR kinase, an EGFR kinase domain, or the expression or activity or level of any of the same described herein). Non-limiting examples of an EGFR-associated disease or disorder include, for example, cancer, for example colorectal cancer, for example metastatic colorectal cancer.

The term "EGFR-associated cancer" as used herein refers to cancers associated with or having a dysregulation of an EGFR gene, an EGFR kinase (also called herein EGFR kinase protein or EGFR), or expression or activity, or level of the same. In one embodiment, the EGFR-associated cancer is colorectal cancer. In one embodiment, the colorectal cancer is metastatic colorectal cancer.

The phrase "dysregulation of a EGFR gene, an EGFR kinase, or the expression or activity or level of the same" refers to a genetic mutation (e.g., an EGFR gene translocation that results in the expression of a fusion protein, a deletion in an EGFR gene that results in the expression of an EGFR protein that includes a deletion of at least one amino acid as compared to the wild-type EGFR protein, a mutation in an EGFR gene that results in the expression of an EGFR protein with one or more point mutations, or an alternative spliced version of an EGFR mRNA that results in an EGFR protein that results in the deletion of at least one amino acid in the EGFR protein as compared to the wild-type EGFR protein), an EGFR gene amplification that results in overexpression of an EGFR protein, or an autocrine activity resulting from the overexpression of an EGFR gene a cell, that results in a pathogenic increase in the activity of a kinase domain of an EGFR protein (e.g., a constitutively active kinase domain of an EGFR protein) in a cell. For example, a dysregulation of an EGFR gene, an EGFR protein, or expression or activity, or level of the same, can be a mutation in an EGFR gene that encodes an EGFR protein that is constitutively active or has increased activity as compared to a protein encoded by an EGFR gene that does not include the mutation. As another example, a dysregulation of an EGFR gene, an EGFR protein, or expression or activity, or level of the same, can be the result of a gene or chromosome translocation which results in the expression of a fusion protein that contains a first portion of EGFR that includes a functional kinase domain, and a second portion of a partner protein (i.e., that is not EGFR). In some examples, dysregulation of an EGFR gene, an EGFR protein, or expression or activity, can be a result of a gene translation of one EGFR gene with another EGFR gene.

When administered simultaneously, sequentially or separately, the BRAF inhibitor (COMPOUND A), the MEK inhibitor (COMPOUND B) and the anti-EGFR antibody (COMPOUND C) may interact in a synergistic manner to strongly inhibit cell proliferation. This unexpected synergistic reaction may allow reduction in the dose required for each compound, leading to a reduction in the side effects and enhancement of the long-term clinical effectiveness of the compounds in treatment.

The term "synergistic effect" as used herein refers to action of two or three therapeutic agents such as, for example, the BRAF inhibitor (COMPOUND A), and/or the MEK inhibitor (COMPOUND B), and/or the anti-EGFR antibody (COMPOUND C) producing an effect, for example, slowing the symptomatic progression of a proliferative disease, particularly cancer, or symptoms thereof, which is greater than the simple addition of the effects of each drug (i.e., therapeutic agent) administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

Also provided is a method of treating a proliferative disease in a subject in need thereof, comprising administering to the subject a COMBINATION OF THE INVENTION, wherein COMPOUND A, COMPOUND B and COMPOUND C are administered at therapeutically effective dosages which, when combined, provide a beneficial effect. The administration of the combination components may be simultaneous or sequential. In one embodiment, COMPOUND A, COMPOUND B and COMPOUND C are each formulated separately in single unit dosage form for simultaneous, separate or sequential administration.

In one embodiment, the proliferative disease treated by the COMBINATION OF THE INVENTION is cancer. Examples of cancers which may be treated with a COMBINATION OF THE INVENTION include colorectal cancer (CRC) (including metastatic colorectal cancer), melanoma (including metastatic melanoma), lung cancer (including non-small cell lung cancer (NSCLC)), breast cancer, kidney cancer such as e.g., renal cell carcinoma (RCC), liver cancer, endometrial cancer, acute myelogenous leukemia (AML), myelodysplasia syndromes (MDS), thyroid cancer, particularly papillary thyroid cancer, pancreatic cancer, neurofibromatosis or hepatocellular carcinoma. Colorectal cancer is the third most common cancer among men and women in the United States, with more than 134,000 new cases and nearly 50,000 deaths from the disease projected in 2016. In the United States, BRAF mutations occur in 8 to 15 percent of patients with colorectal cancer and represent a poor prognosis for these patients. Historical published progression-free survival (PFS) and overall survival (OS) results after first-line treatment range from 1.8 to 2.5 months and 4 to 6 months, respectively, and published response rates from various studies for EGFR-based therapy in this population range from 6 percent to 8 percent. In one embodiment, the cancer is a BRAF-associated cancer. In one embodiment, the cancer is a cancer having a BRAF V600 mutation. In one embodiment, the cancer is a cancer having a BRAF V600E mutation. In one embodiment, the cancer is colorectal cancer. In one embodiment, the colorectal cancer is metastatic colorectal cancer. In one embodiment, the cancer is colorectal cancer having a BRAF V600E mutation. In one embodiment, the cancer is metastatic colorectal cancer having a BRAF V600E mutation. In one embodiment, the cancer is a MEK-associated cancer. In one embodiment, the MEK-associated cancer is colorectal cancer. In one embodiment, the cancer is an EGFR-associated cancer. In one embodiment, the EGFR-associated cancer is colorectal cancer.

In accordance with the present invention, a therapeutically effective amount of each of the combination partners of the COMBINATION OF THE INVENTION may be administered simultaneously, separately or sequentially and in any order, and the components may be administered separately or as a fixed combination. In one embodiment, a method of treating a proliferative disease may comprise (i) administration of COMPOUND A in free or pharmaceutically acceptable salt form, (ii) administration of COMPOUND B in free or pharmaceutically acceptable salt form, and (iii) administration of COMPOUND C, simultaneously or sequentially in any order, in jointly therapeutically effective amounts, (for example in synergistically effective amounts), e.g. in daily or intermittently dosages corresponding to the amounts described herein. The individual combination partners of the COMBINATION OF THE INVENTION may be administered separately at different times during the course of therapy or concurrently in divided or single combination forms. In one embodiment, COMPOUND A may be administered on a daily basis, either once daily or twice daily, COMPOUND B may be administered on a daily basis, either once daily or twice daily, and COMPOUND C may be administered on a weekly basis. The instant invention is therefore to be understood as embracing all such regimens of simultaneous or alternating treatment and the term "administering" is to be interpreted accordingly.

The effective dosage of each of the combination partners employed in the COMBINATION OF THE INVENTION may vary depending on the particular compound or pharmaceutical composition employed, the mode of administration, the condition being treated, and the severity of the condition being treated. Thus, the dosage regimen of the COMBINATION OF THE INVENTION is selected in accordance with a variety of factors including the route of administration and the renal and hepatic function of the patient.

The optimum ratios, individual and combined dosages, and concentrations of the combination partners (COMPOUND A, COMPOUND B and COMPOUND C) of a COMBINATION OF THE INVENTION that yield efficacy without toxicity are based on the kinetics of the therapeutic agents' availability to target sites, and may be determined using methods known to those of skill in the art.

The effective dosage of each of the combination partners may require more frequent administration of one of the compound(s) as compared to the other compound(s) in the combination. Therefore, to permit appropriate dosing, in one embodiment packaged pharmaceutical products may contain one or more dosage forms that contain the combination of compounds, and one or more dosage forms that contain one of the combination of compounds, but not the other compound(s) of the combination. In yet another embodiment, packaged pharmaceutical products may contain one or more dosage forms of one, two and/or three of each of the combination partners.

When the combination partners employed in the COMBINATION OF THE INVENTION are applied in the form as marketed as single drugs, their dosage and mode of administration may be in accordance with the information provided on the package insert of the respective marketed drug, if not mentioned herein otherwise.

The BRAF inhibitor (COMPOUND A) may administered to a suitable subject daily in single or divided doses at an effective dosage in the range of about 0.05 to about 50 mg per kg body weight per day, (e.g., about 0.10 mg/kg/day, 0.30 mg/kg/day, 0.50 mg/kg/day, 0.80 mg/kg/day, 1 mg/kg/day, 5 mg/kg/day, 10 mg/kg/day, 15 mg/kg/day, 20 mg/kg/day, 25 mg/kg/day, 30 mg/kg/day, 35 mg/kg/day, 40 mg/kg/day, 50 mg/kg/day, 0.1-25 mg/kg/day, or 0.5-10 mg/kg/day). For example, doses may be about 35 mg to about 700 mg (e.g., about 50 mg, about 75 mg, about 100 mg, about 120 mg, about 150 mg, about 175 mg, about 200 mg, about 225 mg, about 250 mg, about 275 mg, about 300 mg, about 325 mg, about 350 mg, about 375 mg, about 400 mg, about 450 mg, about 500 mg, about 550 mg, about 600 mg, or about 650 mg), in single or divided doses. For a 70 kg human, this would amount to a preferable dosage range of about 35-700 mg per day, for example 300 mg per day. In one embodiment, COMPOUND A is orally administered. In one embodiment, COMPOUND A is in a capsule form. In one embodiment, a capsule formulation of COMPOUND A comprises 50 mg of COMPOUND A. In one embodiment, a capsule formulation of COMPOUND A comprises 75 mg of COMPOUND A. In one embodiment, a capsule formulation of COMPOUND A comprises 100 mg of COMPOUND A. In one embodiment, a capsule formulation of COMPOUND A comprises amorphous COMPOUND A. In one embodiment, 300 mg of COMPOUND A is orally administered once daily. In one embodiment, 225 mg of COMPOUND A is orally administered once daily. In one embodiment, 150 mg of COMPOUND A is orally administered once daily. In one embodiment, 300 mg of COMPOUND A is initially orally administered once daily until observation of adverse effects, after which 225 mg of COMPOUND A is administered once daily. In one embodiment, patients who have been dose reduced to 225 mg of COMPOUND A once daily may re-escalate to 300 mg of COMPOUND A once daily if the adverse effects that resulted in dose reduction improve to baseline and remain stable for, e.g., up to 6 days, or up to 10 days, or up to 14 days, or up to 15 days, or up to 4 weeks, or up to 6 weeks, depending on the severity of the adverse reaction, provided there are no other concomitant toxicities related to COMPOUND A that would prevent drug re-escalation. In one embodiment, 300 mg of COMPOUND A is initially orally administered once daily until observation of adverse effects, after which 150 mg of COMPOUND A is administered once daily. In one embodiment, patients who have been dose reduced to 150 mg of COMPOUND A once daily may re-escalate to 300 mg of COMPOUND A once daily if the adverse effects that resulted in dose reduction improve to baseline and remain stable for, e.g., up to 6 days, or up to 10 days, or up to 14 days, or up to 15 days, or up to 4 weeks, or up to 6 weeks, depending on the severity of the adverse reaction, provided there are no other concomitant toxicities related to COMPOUND A that would prevent drug re-escalation.

The MEK inhibitor (COMPOUND B) may be administered to a suitable subject daily in single or divided doses at an effective dosage in the range of about 0.001 to about 100 mg per kg body weight per day, (e.g., about 0.01 mg/kg/day, about 0.10 mg/kg/day, 0.30 mg/kg/day, 0.50 mg/kg/day, 0.80 mg/kg/day, 1 mg/kg/day, 5 mg/kg/day, 10 mg/kg/day, 15 mg/kg/day, 20 mg/kg/day, 25 mg/kg/day, 30 mg/kg/day, 35 mg/kg/day, 40 mg/kg/day, 50 mg/kg/day, 60 mg/kg/day, 70 mg/kg/day, 80 mg/kg/day, 90 mg/kg/day, 100 mg/kg/day, 0.1-25 mg/kg/day, 0.5-10 mg/kg/day, or 1-35 mg/kg/day). For example, doses may be about 10 mg to about 85 mg (e.g., about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, or about 85 mg). For a 70 kg human, this would amount to a preferable dosage range of about 0.05 to 7 g/day, preferably about 0.05 to about 2.5 g/day, notably 0.9 g/day. In one embodiment, COMPOUND B is orally administered. In one embodiment, COMPOUND B is formulated as a tablet. In one embodiment, a tablet formulation of COMPOUND B comprises 15 mg of COMPOUND B. In one embodiment, COMPOUND B is orally administered twice daily. In one embodiment, COMPOUND B is orally administered twice daily, wherein the second dose of COMPOUND B is administered about 12 hours after the first dose of COMPOUND B. In one embodiment, 45 mg of COMPOUND B is orally administered twice daily. In one embodiment, COMPOUND B is 6-(4-bromo-2-fluorophenylamino)-7-fluoro-3-methyl-3H-benzoimidazole-5-carboxylic acid (2-hydroxyethoxy)-amide or a pharmaceutically acceptable salt thereof. In one embodiment, COMPOUND B is crystallized 6-(4-bromo-2-fluorophenylamino)-7-fluoro-3-methyl-3H-benzoimidazole-5-carboxylic acid (2-hydroxyethoxy)-amide. In one embodiment, a tablet formulation of COMPOUND B comprises 15 mg of crystallized 6-(4-bromo-2-fluorophenylamino)-7-fluoro-3-methyl-3H-benzoimidazole-5-carboxylic acid (2-hydroxyethoxy)-amide. In one embodiment, 45 mg of crystallized 6-(4-bromo-2-fluorophenylamino)-7-fluoro-3-methyl-3H-benzoimidazole-5-carboxylic acid (2-hydroxyethoxy)-amide is administered twice daily until observation of adverse effects, after which 30 mg of crystallized 6-(4-bromo-2-fluorophenylamino)-7-fluoro-3-methyl-3H-benzoimidazole-5-carboxylic acid (2-hydroxyethoxy)-amide is administered twice daily. In one embodiment, patients who have been dose reduced to 30 mg twice daily may re-escalate to 45 mg twice daily if the adverse effects that resulted in a dose reduction improve to baseline and remain stable for, e.g., up to 14 days, or up to three weeks, or up to 4 weeks, provided there are no other concomitant toxicities related to 6-(4-bromo-2-fluorophenylamino)-7-fluoro-3-methyl-3H-benzoimidazole-5-carboxylic acid (2-hydroxyethoxy)-amide that would prevent drug re-escalation.

In one embodiment, 45 mg of crystallized 6-(4-bromo-2-fluorophenylamino)-7-fluoro-3-methyl-3H-benzoimidazole-5-carboxylic acid (2-hydroxyethoxy)-amide is administered twice daily until observation of adverse effects, after which 15 mg of crystallized 6-(4-bromo-2-fluorophenylamino)-7-fluoro-3-methyl-3H-benzoimidazole-5-carboxylic acid (2-hydroxyethoxy)-amide is administered twice daily. In one embodiment, patients who have been dose reduced to 15 mg twice daily may re-escalate to 45 mg twice daily if the adverse effects that resulted in a dose reduction improve to baseline and remain stable for, e.g., up to 14 days, or up to three weeks, or up to 4 weeks, provided there are no other concomitant toxicities related to 6-(4-bromo-2-fluorophenylamino)-7-fluoro-3-methyl-3H-benzoimidazole-5-carboxylic acid (2-hydroxyethoxy)-amide that would prevent drug re-escalation.

The anti-EGFR antibody (COMPOUND C) may be administered daily or weekly to a suitable subject in single or divided doses at an effective dosage in the range of about 0.001 to about 100 mg per kg body weight per day, (e.g., about 0.01 mg/kg/day, about 0.10 mg/kg/day, 0.30 mg/kg/day, 0.50 mg/kg/day, 0.80 mg/kg/day, 1 mg/kg/day, 5 mg/kg/day, 10 mg/kg/day, 15 mg/kg/day, 20 mg/kg/day, 25 mg/kg/day, 30 mg/kg/day, 35 mg/kg/day, 40 mg/kg/day, 50 mg/kg/day, 60 mg/kg/day, 70 mg/kg/day, 80 mg/kg/day, 90 mg/kg/day, 100 mg/kg/day, 0.1-25 mg/kg/day, 0.5-10 mg/kg/day, or 1-35 mg/kg/day). For example, doses may be about 50 mg, to about 1000 mg, for example about 150 mg to about 500 mg (e.g., about 175 mg, about 200 mg, about 225 mg, about 250 mg, about 275 mg, about 300 mg, about 325 mg, about 350 mg, about 375 mg, about 400 mg, about 425 mg, about 450 mg, or about 475 mg) or about 100 mg to about 350 mg (e.g., about 125 mg, about 150 mg, about 175 mg, about 200 mg, about 225 mg, about 250 mg, about 275 mg, about 300 mg, or about 325 mg). For a 70 kg human, this would amount to a preferable dosage range of about 0.07 to 2.45 g/day, preferably about 0.05 to about 1.0 g/day. In one embodiment, the anti-EGFR antibody is administered as an intravenous infusion. In one embodiment, the anti-EGFR antibody is cetuximab (Erbutux®), wherein cetuximab is administered weekly as an intravenous infusion. In one embodiment, the anti-EGFR antibody is cetuximab (Erbutux®), wherein cetuximab is administered as an intravenous infusion in the amount of 400 mg/m$^2$ over 120 minutes as an initial dose, followed by weekly intravenous infusions in the amount of 250 mg/m$^2$ over 30 minutes according to prescribing information. In one embodiment, the anti-EGFR antibody is cetuximab (Erbutux®), wherein cetuximab is administered as an intravenous infusion in the amount of 400 mg/m$^2$ over 120 minutes as an initial dose, followed by weekly intravenous infusions in the amount of 250 mg/m$^2$ over 60 minutes according to prescribing information. However, dose reduction is also a possibility. Therefore, according one embodiment, cetuximab is administered initially as an intravenous infusion at a dose of from 200 to 400 mg/m$^2$ over 120 minutes followed by weekly intravenous infusions at a dose of from 125 to 250 mg/m$^2$. For example, in one embodiment the dose of cetuximab administered after the initial intravenous infusion in the amount of 400 mg/m$^2$ is reduced to 200 mg/m$^2$ (60-minute infusion) once weekly. In another embodiment, the dose of cetuximab administered after the initial intravenous infusion in the amount of 400 mg/m$^2$ is reduced to 150 mg/m$^2$ (60-minute infusion) once weekly.

In one embodiment, a dosing regimen of a COMBINATION OF THE INVENTION comprises oral administration of a therapeutically effective amount of COMPOUND A, oral administration of a therapeutically effective amount of COMPOUND B, and intravenous administration of a therapeutically effective amount of COMPOUND C. In one embodiment, a dosing regimen of a COMBINATION OF THE INVENTION comprises oral administration of COMPOUND A (300 mg orally administered twice daily), oral administration of COMPOUND B (45 mg orally administered once daily) and intravenous administration of COMPOUND C. In one embodiment, a dosing regimen of a COMBINATION OF THE INVENTION comprises oral administration of COMPOUND A (300 mg orally administered twice daily), oral administration of COMPOUND B (45 mg orally administered once daily) and weekly intravenous administration of COMPOUND C. In one embodiment, COMPOUND A is in the amorphous form. In one embodiment, COMPOUND B is 6-(4-bromo-2-fluorophenylamino)-7-fluoro-3-methyl-3H-benzoimidazole-5-carboxylic acid (2-hydroxyethoxy)-amide. In one embodiment, COMPOUND B is crystallized 6-(4-bromo-2-fluorophenylamino)-7-fluoro-3-methyl-3H-benzoimidazole-5-carboxylic acid (2-hydroxyethoxy)-amide. In one embodiment, COMPOUND B is orally administered twice daily, wherein the second dose of COMPOUND B is administered about 12 hours after the first dose of COMPOUND B. In one embodiment, COMPOUND C is cetuximab. In one embodiment, cetuximab is administered as an intravenous infusion in the amount of 400 mg/m$^2$ over 120 minutes as an initial dose, followed by weekly intravenous infusions in the amount of 250 mg/m$^2$ over 30 minutes. In one embodiment, cetuximab is administered initially as an intravenous infusion at a dose of from 200 to 400 mg/m$^2$ over 120 minutes as an initial dose followed by weekly intravenous infusions at a dose of from 125 to 250 mg/m$^2$ over 30 minutes. In one embodiment, cetuximab is administered as an intravenous infusion in the amount of 400 mg/m$^2$ over 120 minutes as an initial dose, followed by weekly intravenous infusions in the amount of 250 mg/m$^2$ over 60 minutes. In one embodiment, cetuximab is administered initially as an intravenous infusion at a dose of from 200 to 400 mg/m$^2$ over 120 minutes as an initial dose followed by weekly intravenous infusions at a dose of from 125 to 250 mg/m$^2$ over 60 minutes. In one embodiment, a dosing regimen of a COMBINATION OF THE INVENTION comprises oral administration of COMPOUND A (300 mg in a capsule formulation orally administered once daily), oral administration of COMPOUND B (45 mg orally administered twice daily, wherein the administration comprises orally administering three tablets of a tablet formulation of COMPOUND B wherein each tablet comprises 15 mg of COMPOUND B), and intravenous administration of COMPOUND C. In one embodiment, COMPOUND B is orally administered twice daily, wherein the second dose of COMPOUND B is administered about 12 hours after the first dose of COMPOUND B. In one embodiment, on the days when COMPOUND C is administered, COMPOUND A and COMPOUND B are administered at least 30 minutes prior to administration of COMPOUND C.

A COMBINATION OF THE INVENTION can be administered as a COMBINATION THERAPY. The term "combination therapy" as used herein refers to a dosing regimen of the therapeutically active agents COMPOUND A, COMPOUND B, and COMPOUND C encompassed in single or multiple compositions, wherein the therapeutically active agents are administered together or separately (each or in any combinations thereof) in a manner prescribed by a medical care taker or according to a regulatory agency as defined herein. Accordingly, in one embodiment, provided herein is a method of treating a proliferative disease, comprising administering to a patient in need thereof a combination therapy comprising therapeutically effective amounts, independently, of: (a) a BRAF inhibitor which is methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate (COMPOUND A) or a pharmaceutically acceptable salt thereof, (b) at least one MEK inhibitor (COMPOUND B) or a pharmaceutically acceptable salt thereof, and (c) an anti-EGFR antibody (COMPOUND C).

In one embodiment any of the dosing regimens of a COMBINATION THERAPY as described herein, a therapeutically effective amount of COMPOUND A is taken together with the first therapeutically effective dose of COMPOUND B. As used herein, the phrase "taken together with" means that not more than 5 minute, or not more than 10 minutes, or not more than 15 minutes, or not more than 20 minutes, or not more than 25 minutes, or not more than 30 minutes have passed between the administration of COMPOUND A and COMPOUND B.

In one embodiment any of the dosing regimens of a COMBINATION THERAPY as described herein, the second therapeutically effective dose of COMPOUND B is administered about 12 hours after the administration of the first dose of COMPOUND B. As used herein, the phrase "about 12 hours after the administration of the first dose of COMPOUND B" means that the second dose of COMPOUND B is administered 10 to 14 hours after the administration of the first dose of COMPOUND B.

In one embodiment of any of the dosing regimens of a COMBINATION THERAPY as described herein, on days when COMPOUND C is administered, COMPOUND C is administered at least 30 minutes after the latter of administration of a therapeutically effective amount of COMPOUND A and the first therapeutically effective dose of COMPOUND B. As used herein, the phrase "at least 30 minutes after" means that COMPOUND C is administered at least 30 minutes, or at least 35 minutes, or at least 40 minutes, or at least 45 minutes, or at least 50 minutes, or at least 55 minutes, or at least 60 minutes, or at least 65 minutes, or at least 70 minutes, or at least 75 minutes, or at least 80 minutes, or at least 85 minutes, or at least 90 minutes after the latter of administration of COMPOUND A and the first dose of COMPOUND B.

In one embodiment of any of the dosing regimens of a COMBINATION THERAPY as described herein, on days when COMPOUND C is administered, a therapeutically effective amount of COMPOUND C is administered at least 30 minutes before administration of a therapeutically effective amount of COMPOUND A and the first therapeutically effective dose of COMPOUND B, whichever is first. As used herein, the phrase "at least 30 minutes before" means that COMPOUND C is administered at least 30 minutes, or at least 35 minutes, or at least 40 minutes, or at least 45 minutes, or at least 50 minutes, or at least 55 minutes, or at least 60 minutes before administration of COMPOUND A and the first dose of COMPOUND B, whichever is first.

In one embodiment, the dosing regimen of a COMBINATION THERAPY comprises:

| Drug | administration |
| --- | --- |
| A therapeutically effective amount of COMPOUND A: amorphous methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate | Orally, once daily, in the morning |
| A therapeutically effective amount of COMPOUND B: crystalline 6-(4-bromo-2-fluorophenylamino)-7-fluoro-3-methyl-3H-benzoimidazole-5-carboxylic acid (2-hydroxyethoxy)-amide | Orally, twice daily [i.e., once daily in the morning (first dose) and once daily in the evening (second dose)]; wherein the first dose of COMPOUND B may be administered: (i) together with COMPOUND A; (ii) before administration of COMPOUND A; or (iii) after administration of COMPOUND A and wherein the second dose of COMPOUND B is administered 12 hours ±2 hours after the first dose of COMPOUND B |
| COMPOUND C: cetuximab | Intravenous infusion, in the amount of 400 mg/m$^2$ over 120 minutes as an initial dose on the first day of administration of a COMBINATION OF THE INVENTION, followed by weekly intravenous infusions in the amount of 250 mg/m$^2$ over 60 minutes |

In one embodiment, the dosing regimen comprises:

| Drug | administration |
| --- | --- |
| COMPOUND A: amorphous methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate | Orally, 300 mg (four 75 mg capsules) once daily in the morning, with or without food |

| Drug | administration |
|---|---|
| COMPOUND B:<br>crystalline 6-(4-bromo-2-fluorophenylamino)-7-fluoro-3-methyl-3H-benzoimidazole-5-carboxylic acid (2-hydroxyethoxy)-amide | Orally, 45 mg (three 15 mg tablets) twice daily [i.e., once daily in the morning (first dose) and once daily in the evening (second dose)], with or without food,<br>wherein the first dose of COMPOUND B may be administered<br>(i) together with COMPOUND A;<br>(ii) before administration of COMPOUND A; or<br>(iii) after administration of COMPOUND A;<br>and wherein the second dose of COMPOUND B is administered 12 hours ±2 hours after the first dose of COMPOUND B |
| COMPOUND C:<br>cetuximab | Intravenous infusion, in the amount of 400 mg/m² over 120 minutes as an initial dose on the first day of administration of a COMBINATION OF THE INVENTION, followed by weekly intravenous infusions in the amount of 250 mg/m² over 60 minutes; wherein COMPOUND C is administered at least 30 minutes after administration of the latter of dosing of COMPOUND A or COMPOUND B |

In one embodiment, the dosing regimen comprises:

| Drug | administration |
|---|---|
| COMPOUND A:<br>amorphous methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate | Orally, 300 mg (four 75 mg capsules) once daily in the morning, with or without food |
| COMPOUND B:<br>crystalline 6-(4-bromo-2-fluorophenylamino)-7-fluoro-3-methyl-3H-benzoimidazole-5-carboxylic acid (2-hydroxyethoxy)-amide | Orally, 45 mg (three 15 mg tablets) twice daily [i.e., once daily in the morning (first dose) and once daily in the evening (second dose)], with or without food,<br>wherein the first dose may be administered<br>(i) together with COMPOUND A;<br>(ii) before administration of COMPOUND A; or<br>(iii) after administration of COMPOUND A;<br>and wherein the second dose of COMPOUND B is administered 12 hours ±2 hours after the first dose of COMPOUND B |
| COMPOUND C:<br>cetuximab | Intravenous infusion, in the amount of 400 mg/m² over 120 minutes as an initial dose on the first day of administration of a COMBINATION OF THE INVENTION, followed by weekly intravenous infusions in the amount of 250 mg/m² over 60 minutes; wherein COMPOUND C is administered at least 60 minutes after administration of the latter of dosing of COMPOUND A or COMPOUND B |

In one embodiment, the dosing regimen comprises:

| Drug | administration |
|---|---|
| COMPOUND A:<br>amorphous methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate | Orally, 300 mg (four 75 mg capsules) once daily in the morning, with or without food |
| COMPOUND B:<br>crystalline 6-(4-bromo-2-fluorophenylamino)-7-fluoro-3-methyl-3H-benzoimidazole-5-carboxylic acid (2-hydroxyethoxy)-amide | Orally, 45 mg (three 15 mg tablets) twice daily [i.e., once daily in the morning (first dose) and once daily in the evening (second dose)], with or without food,<br>wherein the first dose of Compound B may be administered |

| Drug | administration |
|---|---|
| | (i) together with COMPOUND A;<br>(ii) before administration of COMPOUND A; or<br>(iii) after administration of COMPOUND A<br>and wherein the second dose of COMPOUND B is administered 12 hours ±2 hours after the first dose of COMPOUND B |
| COMPOUND C:<br>cetuximab | intravenous infusion, in the amount of 400 mg/m$^2$ over 120 minutes as an initial dose in the morning on the first day of administration of a COMBINATION OF THE INVENTION, followed by weekly intravenous infusions in the amount of 250 mg/m$^2$ over 60 minutes; wherein COMPOUND C is administered at least 30 minutes before administration of COMPOUND A and the first dose of COMPOUND B |

In one embodiment, any COMBINATION THERAPY described herein optionally further comprises administration of one or more pre-medications prior to administration of COMPOUND C. In one embodiment, the one or more pre-medication(s) is administered no sooner than 1 hour after administration of COMPOUND A and binimetinib COMPOUND B. In one embodiment, the one or more premedication(s) is administered 30-60 minutes prior administration of COMPOUND C. In one embodiment, the one or more premedication(s) is administered 30 minutes prior administration of COMPOUND C. In one embodiment, the one or more pre-medications is selected from one or more of a Hi antagonists (e.g., antihistamines such as diphenhydramine) and systemic corticosteroids (e.g., a low-dose systemic corticosteroid, e.g., dexamethasone or prednisolone).

In one embodiment, any COMBINATION THERAPY described herein further comprises instructing the patient to avoid consumption of grapefruit, pomegranates, star fruits, Seville oranges or products containing any of these juices.

The optimal dosage of each combination partner for treatment of a proliferative disease can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

The amount of each combination partner that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage may vary depending on the compound used and the particular condition to be treated. In general, the use of the minimum dosage that is sufficient to provide effective therapy is preferred. Patients may generally be monitored for therapeutic effectiveness using assays suitable for the condition being treated, which will be familiar to those of ordinary skill in the art.

Also provided herein is a method of treating a subject having a proliferative disease comprising administering to said subject a COMBINATION OF THE INVENTION in a quantity which is jointly therapeutically effective against a proliferative disease. In one embodiment, the proliferative disease to be treated with a COMBINATION OF THE INVENTION is cancer. In one embodiment, the cancer is selected from colorectal cancer (CRC) (including metastatic colorectal cancer), melanoma (including metastatic and unresectable melanoma), lung cancer (including non-small cell lung cancer (NSCLC)), breast cancer, kidney cancer such as e.g., renal cell carcinoma (RCC), liver cancer, endometrial cancer, acute myelogenous leukemia (AML), myelodysplasia syndromes (MDS), thyroid cancer, particularly papillary thyroid cancer, pancreatic cancer, neurofibromatosis and hepatocellular carcinoma. In one embodiment, the cancer is colorectal cancer (CRC). In one embodiment, the colorectal cancer is metastatic colorectal cancer. In one embodiment, the cancer is a BRAF-associated cancer. In one embodiment, the cancer is a cancer having a BRAF V600 mutation. In one embodiment, the cancer is a cancer having a BRAF V600E mutation. In one embodiment, the cancer is colorectal cancer. In one embodiment, the cancer is colorectal cancer having a BRAF V600E mutation. In one embodiment, the cancer is metastatic colorectal cancer having a BRAF V600E mutation. In one embodiment, the cancer is a MEK-associated cancer. In one embodiment, the cancer is an EGFR-associated cancer.

In one embodiment, provided herein is a method of treating cancer in a patient in need thereof, the method comprising: (a) determining if the cancer in the patient is a BRAF-associated cancer; and (b) if the cancer is determined to be a BRAF-associated cancer, administering to the patient a therapeutically effective amount of a COMBINATION OF THE INVENTION. In some embodiments, the patient is determined to have a BRAF-associated cancer through the use of a regulatory agency-approved, e.g., FDA-approved test or assay for identifying dysregulation of a BRAF gene, a BRAF kinase, or expression or activity or level of any of the same, in a patient or a biopsy sample from the patient or by performing any of the non-limiting examples of assays described herein. In some embodiments, the test or assay is provided as a kit. In some embodiments, the cancer is a BRAF mutant colorectal cancer. In one embodiment, the cancer is metastatic colorectal cancer having a BRAF mutation. In one embodiment, the cancer is metastatic colorectal cancer having a BRAF V600E mutation.

In one embodiment, provided herein is a method of treating cancer in a subject in need thereof, the method comprising (a) determining if the cancer has a mutant BRAF kinase, and (b) if the cancer is determined to have a mutant BRAF kinase, administering to said subject a therapeutically effective amount of COMBINATION OF THE INVENTION.

In one embodiment, provided herein is a method (e.g., in vitro method) of selecting a treatment for a patient identified or diagnosed as having a BRAF-associated cancer. Some embodiments can further include administering the selected treatment to the patient identified or diagnosed as having a BRAF-associated cancer. For example, the selected treatment can include administration of a therapeutically effective amount of a COMBINATION OF THE INVENTION. Some embodiments can further include a step of performing an assay on a sample obtained from the patient to determine whether the patient has a dysregulation of a BRAF gene, a BRAF kinase, or expression or activity or level of any of the same, and identifying and diagnosing a patient determined to have a dysregulation of a BRAF gene, a BRAF kinase, or expression or activity or level of any of the same, as having a BRAF-associated cancer. In some embodiments, the patient has been identified or diagnosed as having a BRAF-associated cancer through the use of a regulatory agency-approved, e.g., FDA-approved, kit for identifying dysregulation of a BRAF gene, a BRAF kinase, or expression or activity or level of any of the same, in a patient or a biopsy sample from the patient. In some embodiments, the BRAF-associated cancer is a cancer described herein or known in the art. In some embodiments, the BRAF-associated cancer is colorectal cancer. In some embodiments, the BRAF-associated cancer is colorectal cancer having a BRAF V600E mutation. In some embodiments, the BRAF-associated cancer is metastatic colorectal cancer. In some embodiments, the BRAF-associated cancer is metastatic colorectal cancer having a BRAF V600E mutation. In some embodiments, the assay is an in vitro assay, for example, an assay that utilizes the next generation sequencing, immunohistochemistry, or break apart FISH analysis. In some embodiments, the assay is a regulatory agency-approved, e.g., FDA-approved, kit.

In one embodiment, provided herein is a method of selecting a patient for treatment, wherein the methods include selecting, identifying, or diagnosing a patient having a BRAF-associated cancer, and selecting the patient for treatment including administration of a therapeutically-effective amount of a COMBINATION OF THE INVENTION. In some embodiments, identifying or diagnosing a patient as having a BRAF-associated cancer can include a step of performing an assay on a sample obtained from the patient (e.g., a biopsy sample) to determine whether the patient has a dysregulation of a BRAF gene, a BRAF kinase, or expression or activity or level of any of the same, and identifying or diagnosing a patient determined to have a dysregulation of a BRAF gene, a BRAF kinase, or expression or activity or level of any of the same, as having a BRAF-associated cancer. In some embodiments, the BRAF-associated cancer is colorectal cancer having a BRAF V600E mutation. In some embodiments, the BRAF-associated cancer is metastatic colorectal cancer. In some embodiments, the BRAF-associated cancer is metastatic colorectal cancer having a BRAF V600E mutation. In some embodiments, the assay is an in vitro assay, for example, an assay that utilizes the next generation sequencing, immunohistochemistry, or break apart FISH analysis. In some embodiments, the assay is a regulatory agency-approved, e.g., FDA-approved, kit.

Also provided are methods of determining the likelihood that a subject having a cancer will have a positive response to treatment with a COMBINATION OF THE INVENTION that include: determining whether a cancer cell in a sample obtained from the subject has one or more BRAF mutations; and determining that the subject having the cancer cell that has one or more BRAF mutations has an increased likelihood of having a positive response to treatment with a COMBINATION OF THE INVENTION.

Also provided are methods of predicting the efficacy of treatment with a pharmaceutical combination of the invention in a subject having cancer that include: determining whether a cancer cell in a sample obtained from the subject has one or more BRAF mutations; and determining that treatment with a COMBINATION OF THE INVENTION is more likely to be effective in a subject having a cancer cell in a sample obtained from the subject that has one or more BRAF mutations. In one embodiment, the BRAF mutation is a V600E mutation.

In one embodiment, provided herein is a method of treating a BRAF-associated cancer (e.g., a cancer having a BRAF kinase mutation) in a subject in need thereof, the method comprising (a) determining if the cancer has a mutant BRAF kinase, and (b) if the cancer is determined to have a mutant BRAF kinase, administering to said subject a therapeutically effective amount of a COMBINATION OF THE INVENTION. In one embodiment, the COMBINATION OF THE INVENTION comprises amorphous methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate or a pharmaceutically acceptable salt thereof (COMPOUND A), 6-(4-bromo-2-fluorophenylamino)-7-fluoro-3-methyl-3H-benzoimidazole-5-carboxylic acid (2-hydroxyethoxy)-amide or a pharmaceutically acceptable salt thereof (COMPOUND B) and cetuximab (COMPOUND C). In one embodiment, COMPOUND B is crystallized 6-(4-bromo-2-fluorophenylamino)-7-fluoro-3-methyl-3H-benzoimidazole-5-carboxylic acid (2-hydroxyethoxy)-amide. In one embodiment, the cancer is a cancer having a BRAF V600 mutation. In one embodiment, the cancer is a cancer having a BRAF V600E mutation. In one embodiment, the cancer is colorectal cancer. In one embodiment, the cancer is metastatic colorectal cancer. In one embodiment, the cancer is colorectal cancer having a BRAF V600E mutation. In one embodiment, the cancer is metastatic colorectal cancer having a BRAF V600E mutation. In one embodiment, the subject has stage IV colorectal cancer. In one embodiment, the subject has stage IV colorectal cancer having a BRAF V600E mutation. In some embodiments, the subject was previously treated with another anticancer treatment, e.g., first- or second-line systemic anticancer therapy (e.g., treatment with one or more cytotoxic agents), resection of a tumor, or radiation therapy. In one embodiment, the subject has metastatic colorectal cancer and was previously treated with one or two treatment regimens with first- or second-line systemic anticancer therapy (e.g., treatment with one or more cytotoxic agents). In one embodiment, the subject has metastatic colorectal cancer which has progressed after one or two treatment regimens with first- or second-line systemic anticancer therapy (e.g., treatment with one or more cytotoxic agents). In one embodiment, the cytotoxic agents are selected from irinotecan, oxaliplatin, capecitabine, folinic acid and 5-fluorouracil. In one embodiment, the subject has a cancer that also expresses wild-type KRAS ($KRAS^{wt}$).

In one embodiment, provided herein is a method of treating a BRAF-associated cancer (e.g., a cancer having a BRAF kinase mutation) in a subject in need thereof, the method comprising (a) detecting a mutant BRAF kinase in the cancer, and (b) administering to said subject a therapeutically effective amount of a COMBINATION OF THE INVENTION. In one embodiment, the COMBINATION OF THE INVENTION comprises amorphous methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate or a pharmaceutically acceptable salt thereof (COMPOUND A), 6-(4-bromo-2-fluorophenylamino)-7-fluoro-3-methyl-3H-benzoimidazole-5-carboxylic acid (2-hydroxyethoxy)-amide or a pharmaceutically acceptable salt thereof (COMPOUND B) and cetuximab (COMPOUND C). In one embodiment, COMPOUND B is crystallized 6-(4-bromo-2-fluorophenylamino)-7-fluoro-3-methyl-3H-benzoimidazole-5-carboxylic acid (2-hydroxyethoxy)-amide. In one embodiment, the cancer is a cancer having a BRAF V600 mutation. In one embodiment, the cancer is a cancer having a BRAF V600E mutation. In one embodiment, the cancer is colorectal cancer. In one embodiment, the cancer is metastatic colorectal cancer. In one embodiment, the cancer is colorectal cancer having a BRAF V600E mutation. In one embodiment, the cancer is metastatic colorectal cancer having a BRAF V600E mutation. In some embodiments, the subject was previously treated with another anticancer treatment, e.g., first- or second-line systemic anticancer therapy (e.g., treatment with one or more cytotoxic agents), resection of a tumor, or radiation therapy. In one embodiment, the subject has metastatic colorectal cancer and was previously treated with one or two treatment regimens with first- or second-line systemic anticancer therapy (e.g., treatment with one or more cytotoxic agents). In one embodiment, the subject has metastatic colorectal cancer which has progressed after one or two treatment regimens with first- or second-line systemic anticancer therapy (e.g., treatment with one or more cytotoxic agents). In one embodiment, the cytotoxic agents are selected from irinotecan, oxaliplatin, capecitabine, folinic acid and 5-fluorouracil. In one embodiment, the subject has a cancer that also expresses wild-type KRAS (KRAS$^{wt}$).

In one embodiment, provided herein is a method of treating a subject having colorectal cancer, comprising administering to said subject a COMBINATION OF THE INVENTION in a quantity which is jointly therapeutically effective against said colorectal cancer. In one embodiment, the subject has colorectal cancer having a BRAF V600E mutation. In one embodiment, the subject is determined to have colorectal cancer having a BRAF V600E mutation as determined using a regulatory agency-approved, e.g., FDA-approved assay or kit. In one embodiment, the colorectal cancer is metastatic colorectal cancer. In one embodiment, the subject has stage IV colorectal cancer. In one embodiment, the subject has stage IV colorectal cancer having a BRAF V600E mutation. In some embodiments, the subject was previously treated with another anticancer treatment, e.g., first- or second-line systemic anticancer therapy (e.g., treatment with one or more cytotoxic agents), resection of a tumor, or radiation therapy. In one embodiment, the subject has metastatic colorectal cancer and was previously treated with one or two treatment regimens with first- or second-line systemic anticancer therapy (e.g., treatment with one or more cytotoxic agents). In one embodiment, the subject has metastatic colorectal cancer which has progressed after one or two treatment regimens with first- or second-line systemic anticancer therapy (e.g., treatment with one or more cytotoxic agents). In one embodiment, the cytotoxic agents are selected from irinotecan, oxaliplatin, capecitabine, folinic acid and 5-fluorouracil. In one embodiment, the subject has a cancer that also expresses wild-type KRAS (KRAS$^{wt}$).

Also provided are methods of treating a patient that include performing an assay on a sample obtained from the patient to determine whether the patient has a BRAF-associated cancer (e.g., a cancer having a BRAF kinase mutation), and administering a therapeutically effective amount of a COMBINATION OF THE INVENTION to the patient determined to have BRAF-associated cancer (e.g., a cancer having a BRAF kinase mutation). In some embodiments, the subject was previously treated with another anticancer treatment, e.g., first- or second-line systemic anticancer therapy (e.g., treatment with one or more cytotoxic agents), resection of a tumor, or radiation therapy. In one embodiment, the subject has metastatic colorectal cancer and was previously treated with one or two treatment regimens with first- or second-line systemic anticancer therapy (e.g., treatment with one or more cytotoxic agents). In one embodiment, the subject has metastatic colorectal cancer which has progressed after one or two treatment regimens with first- or second-line systemic anticancer therapy (e.g., treatment with one or more cytotoxic agents). In one embodiment, the cytotoxic agents are selected from irinotecan, oxaliplatin, capecitabine, folinic acid and 5-fluorouracil. In some embodiments, the patient is a patient suspected of having a BRAF-associated cancer (e.g., a cancer having a BRAF kinase mutation), a patient presenting with one or more symptoms of a BRAF-associated cancer (e.g., a cancer having a BRAF kinase mutation), or a patient having an elevated risk of developing a BRAF-associated cancer (e.g., a cancer having a BRAF kinase mutation). In one embodiment, the cancer is a cancer having a BRAF V600 mutation. In one embodiment, the cancer is a cancer having a BRAF V600E mutation. In some embodiments, the cancer is colorectal cancer. In one embodiment, the colorectal cancer is metastatic colorectal cancer. In one embodiment, the cancer is colorectal cancer having a BRAF V600 mutation. In one embodiment, the cancer is colorectal cancer having a BRAF V600E mutation. In one embodiment, the subject has stage IV colorectal cancer. In one embodiment, the method further comprises performing an assay to determine if the patient has a cancer that also expresses wild-type KRAS (KRAS$^{wt}$).

In one embodiment, provided herein is a method of treating a subject having a BRAF-associated cancer (e.g., a cancer having a BRAF kinase mutation), said method comprising administering to said subject a therapeutically effective amount of a COMBINATION OF THE INVENTION, wherein the subject was treated with first- or second-line systemic anticancer therapy prior to treatment with said COMBINATION OF THE INVENTION. In one embodiment, the subject has received one or two treatment regimens of systemic anticancer therapy prior to treatment with a COMBINATION OF THE INVENTION. In one embodiment, the subject has metastatic colorectal cancer and was previously treated with one or two treatment regimens with first- or second-line systemic anticancer therapy (e.g., treatment with one or more cytotoxic agents). In one embodiment, the subject has metastatic colorectal cancer which has progressed after one or two treatment regimens with first- or second-line systemic anticancer therapy (e.g., treatment with one or more cytotoxic agents). In one embodiment, the first- and second-line systemic therapies include treatment with one or more cytotoxic agents. In one embodiment, the one or more cytotoxic agents are selected from irinotecan, oxaliplatin, capecitabine, folinic acid and 5-fluorouracil. In one embodiment, the systemic anticancer therapy does not include a BRAF inhibitor, a MEK inhibitor or an EGFR inhibitor. In one embodiment, the cancer is a cancer having a BRAF V600 mutation. In one embodiment, the cancer is a cancer having a BRAF V600E mutation. In one embodiment, the cancer is colorectal cancer. In one embodiment, the cancer is metastatic colorectal cancer. In one embodiment, the cancer is colorectal cancer having a BRAF V600E mutation. In one embodiment, the cancer is metastatic colorectal cancer having a BRAF V600E mutation. In one embodiment, the subject has a cancer that also expresses wild-type KRAS ($KRAS^{wt}$).

In one embodiment, provided herein is a method of treating a subject having colorectal cancer wherein said colorectal cancer has a BRAF V600E mutation, the method comprising (i) administering at least one cytotoxic agent to said subject for a period of time; and (ii) ceasing administration of said at least one cytotoxic agent and initiating treatment with a COMBINATION OF THE INVENTION, wherein said treatment with said COMBINATION OF THE INVENTION includes any of the treatment regimens described herein. In one embodiment, the subject has stage IV colorectal cancer having a BRAF V600E mutation. In one embodiment, the cytotoxic agents are selected from irinotecan, oxaliplatin, capecitabine, folinic acid and 5-fluorouracil. In one embodiment, the subject has a cancer that also expresses wild-type KRAS ($KRAS^{wt}$).

In one embodiment, provided herein is a method of treating a subject having colorectal cancer having a BRAF V600E mutation, the method comprising administering to said subject a COMBINATION OF THE INVENTION in a quantity which is jointly therapeutically effective against said colon cancer, wherein the subject has not received prior treatment with a BRAF inhibitor prior to treatment with a COMBINATION OF THE INVENTION. In one embodiment, the cancer also expresses wild-type KRAS ($KRAS^{wt}$).

In one embodiment, provided herein is a method of treating a subject having colorectal cancer having a BRAF V600E mutation comprising administering to said subject a COMBINATION OF THE INVENTION in a quantity which is jointly therapeutically effective against said colon cancer, wherein the subject has not received prior treatment with a MEK inhibitor prior to treatment with a COMBINATION OF THE INVENTION. In one embodiment, the cancer also expresses wild-type KRAS ($KRAS^{wt}$).

In one embodiment, provided herein is a method of treating a subject having colorectal cancer having a BRAF V600E mutation, the method comprising administering to said subject a COMBINATION OF THE INVENTION in a quantity which is jointly therapeutically effective against said colon cancer, wherein the subject has not received prior treatment with an EGFR inhibitor prior to treatment with a COMBINATION OF THE INVENTION. In one embodiment, the subject has not received treatment with an EGFR inhibitor selected from cetuximab and panitumumab prior to treatment with a COMBINATION OF THE INVENTION. In one embodiment, the cancer also expresses wild-type KRAS ($KRAS^{wt}$).

In one embodiment, provided herein is a method of treating a subject having colorectal cancer having a BRAF V600E mutation, the method comprising administering to said subject a COMBINATION OF THE INVENTION in a quantity which is jointly therapeutically effective against said colon cancer, wherein the subject has not received treatment with a BRAF inhibitor, a MEK inhibitor and/or an EGFR inhibitor prior to treatment with a COMBINATION OF THE INVENTION. In one embodiment, the cancer also expresses wild-type KRAS ($KRAS^{wt}$).

In one embodiment, provided herein is a method of reducing the size of a malignant tumor, comprising contacting the tumor with a COMBINATION OF THE INVENTION. In one embodiment, the contacting is in vitro. In one embodiment, the contacting is in vivo. In one embodiment, the tumor is selected from colorectal cancer (CRC) (including metastatic colorectal cancer), melanoma (including metastatic melanoma), lung cancer (including non-small cell lung cancer (NSCLC)), breast cancer, kidney cancer such as e.g., renal cell carcinoma (RCC), liver cancer, endometrial cancer, acute myelogenous leukemia (AML), myelodysplasia syndromes (MDS), thyroid cancer, particularly papillary thyroid cancer, pancreatic cancer, neurofibromatosis and hepatocellular carcinoma. In one embodiment, the cancer is colorectal cancer (CRC). In one embodiment, the colorectal cancer is metastatic colorectal cancer. In one embodiment, the cancer is a BRAF-associated cancer. In one embodiment, the cancer is a cancer having a BRAF V600 mutation. In one embodiment, the cancer is a cancer having a BRAF V600E mutation. In one embodiment, the cancer is colorectal cancer having a BRAF V600E mutation. In one embodiment, the cancer is metastatic colorectal cancer having a BRAF V600E mutation. In one embodiment, the cancer also expresses wild-type KRAS ($KRAS^{wt}$).

An improvement in a cancer or cancer-related disease can be characterized as a complete or partial response. "Complete response" or "CR" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions.

Treatment may be assessed by inhibition of disease progression, inhibition of tumor growth, reduction of primary tumor, relief of tumor-related symptoms, inhibition of tumor secreted factors (including expression levels of checkpoint proteins as identified herein), delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP as used herein means the time from treatment onset until tumor progression; TTP does not comprise deaths. As used herein, PFS means the time from treatment onset until tumor progression or death. In the extreme, complete inhibition, is referred to herein as prevention or chemoprevention.

In some embodiments of the methods described herein, the treatment can be assessed by one or more clinical endpoints selected from positive tumor response, complete response, partial response or stable disease, increased survival without tumor progression, inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS) or increased Duration of Response (DOR).

Thus, provided herein are methods for achieving one or more clinical endpoints associated with treating a hematological cancer (or solid tumor) described herein. In one embodiment, a patient described herein can show a positive tumor response, such as inhibition of tumor growth or a reduction in tumor size after treatment with a combination described herein. In certain embodiments, a patient described herein can achieve a Response Evaluation Criteria in Solid Tumors (for example, RECIST 1.1) of complete response, partial response or stable disease after administration of an effective amount a COMBINATION OF THE INVENTION. In certain embodiments, a patient described herein can show increased survival without tumor progression. In some embodiments, a patient described herein can show inhibition of disease progression, inhibition of tumor growth, reduction of primary tumor, relief of tumor-related symptoms, inhibition of tumor secreted factors (including tumor secreted hormones, such as those that contribute to carcinoid syndrome), delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), and/or increased Overall Survival (OS), among others.

In another embodiment, methods are provided for increasing the overall survival, objective response rate, time to progression, progression-free survival and/or time-to-treatment failure of a patient having a cancer described herein, comprising administering an effective amount of a COMBINATION OF THE INVENTION as described herein. In one embodiment, a method is provided for increasing the overall survival of a patient having a cancer described herein, comprising administering an effective amount of a COMBINATION OF THE INVENTION as described herein. In one embodiment, is a method for increasing the objective response rate of a patient a cancer described herein, comprising administering an effective amount of a COMBINATION OF THE INVENTION as described herein. In one embodiment, is a method for increasing the time to progression of a patient having a cancer described herein, comprising administering an effective amount of a COMBINATION OF THE INVENTION as described herein. In one embodiment, is a method for increasing the progression-free survival of a patient having a cancer described herein, comprising administering an effective amount of a COMBINATION OF THE INVENTION as described herein. In one embodiment, is a method for increasing the time-to-treatment failure of a patient having a cancer described herein, comprising administering an effective amount of a COMBINATION OF THE INVENTION as described herein. In one embodiment, the cancer is a cancer having a BRAF V600 mutation. In one embodiment, the cancer is a cancer having a BRAF V600E mutation. In some embodiments, the cancer is colorectal cancer. In one embodiment, the colorectal cancer is metastatic colorectal cancer. In one embodiment, the cancer is colorectal cancer having a BRAF V600 mutation. In one embodiment, the cancer is colorectal cancer having a BRAF V600E mutation.

In some embodiments of any of the methods or uses described herein, an assay used to determine whether the patient has a BRAF-associated cancer using a sample from a patient can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a BRAF gene, a BRAF kinase, or expression or activity or levels of any of the same (see, e.g., the references cited herein). In some embodiments, the sample is a biological sample or a biopsy sample (e.g., a paraffin-embedded biopsy sample) from the patient. In some embodiments, the patient is a patient suspected of having a BRAF-associated cancer, a patient having one or more symptoms of a BRAF-associated cancer, and/or a patient that has an increased risk of developing a BRAF-associated cancer).

In one embodiment, the methods of treating cancer according to the invention also include surgery or radiotherapy. Non-limiting examples of surgery include, e.g., open surgery or minimally invasive surgery. Surgery can include, e.g., removing an entire tumor, debulking of a tumor, or removing a tumor that is causing pain or pressure in the subject. Methods for performing open surgery and minimally invasive surgery on a subject having a cancer are known in the art. Non-limiting examples of radiation therapy include external radiation beam therapy (e.g., external beam therapy using kilovoltage X-rays or megavoltage X-rays) or internal radiation therapy. Internal radiation therapy (also called brachytherapy) can include the use of, e.g., low-dose internal radiation therapy or high-dose internal radiation therapy. Low-dose internal radiation therapy includes, e.g., inserting small radioactive pellets (also called seeds) into or proximal to a cancer tissue in the subject. High-dose internal radiation therapy includes, e.g., inserting a thin tube (e.g., a catheter) or an implant into or proximal to a cancer tissue in the subject, and delivering a high dose of radiation to the thin tube or implant using a radiation machine. Methods for performing radiation therapy on a subject having a cancer are known in the art.

The present invention further relates to a COMBINATION OF THE INVENTION for use in the treatment of a proliferative disease. In one embodiment, the proliferative disease is cancer. In one embodiment, the cancer is selected from colorectal cancer (CRC) (including metastatic colorectal cancer), melanoma (including metastatic and unresectable melanoma), lung cancer (including non-small cell lung cancer (NSCLC)), breast cancer, kidney cancer such as e.g., renal cell carcinoma (RCC), liver cancer, endometrial cancer, acute myelogenous leukemia (AML), myelodysplasia syndromes (MDS), thyroid cancer, particularly papillary thyroid cancer, pancreatic cancer, neurofibromatosis and hepatocellular carcinoma. In one embodiment, the cancer is colorectal cancer (CRC). In one embodiment, the colorectal cancer is metastatic colorectal cancer. In one embodiment, the cancer is a BRAF-associated cancer. In one embodiment, the cancer is a cancer having a BRAF V600 mutation. In one embodiment, the cancer is a cancer having a BRAF V600E mutation. In one embodiment, the cancer is colorectal cancer. In one embodiment, the cancer is colorectal cancer having a BRAF V600E mutation. In one embodiment, the cancer is a MEK-associated cancer. In one embodiment, the cancer is an EGFR-associated cancer.

Also provided is a COMBINATION OF THE INVENTION useful for treating a proliferative disease in a subject in need thereof. In one embodiment, the proliferative disease is cancer. In one embodiment, the cancer is selected from colorectal cancer (CRC) (including metastatic colorectal cancer), melanoma (including metastatic and unresectable melanoma), lung cancer (including non-small cell lung cancer (NSCLC)), breast cancer, kidney cancer such as e.g., renal cell carcinoma (RCC), liver cancer, endometrial cancer, acute myelogenous leukemia (AML), myelodysplasia syndromes (MDS), thyroid cancer, particularly papillary thyroid cancer, pancreatic cancer, neurofibromatosis and hepatocellular carcinoma. In one embodiment, the cancer is colorectal cancer (CRC). In one embodiment, the colorectal cancer is metastatic colorectal cancer. In one embodiment, the cancer is a BRAF-associated cancer. In one embodiment, the cancer is a cancer having a BRAF V600 mutation. In one embodiment, the cancer is a cancer having a BRAF V600E mutation. In one embodiment, the cancer is colorectal cancer. In one embodiment, the cancer is colorectal cancer having a BRAF V600E mutation. In one embodiment, the cancer is a MEK-associated cancer. In one embodiment, the MEK-associated cancer is colorectal cancer. In one embodiment, the cancer is an EGFR-associated cancer. In one embodiment, the EGFR-associated cancer is colorectal cancer.

The combination therapy comprising the COMBINATION OF THE INVENTION may result in unexpected improvement in the treatment of proliferative diseases as compared to the monotherapy. In one embodiment, when administered simultaneously, sequentially or separately, the BRAF inhibitor (COMPOUND A), the MEK inhibitor, (COMPOUND B), and (c) the anti-EGFR antibody (COMPOUND C) interact synergistically to inhibit cell proliferation.

The nature of proliferative diseases is multifactorial. Under certain circumstances, drugs with different mechanisms of action may be combined. However, just considering any combination of therapeutic agents having different mode of action does not necessarily lead to combinations with advantageous effects.

The administration of a COMBINATION OF THE INVENTION may result not only in a beneficial effect, e.g. a synergistic therapeutic effect, e.g. with regard to alleviating, delaying progression of (e.g., increasing progression-free survival (PFS)), increasing overall survival (OS), or inhibiting the symptoms, but also in further surprising beneficial effects, e.g. fewer side-effects, an improved quality of life or a decreased morbidity, compared with a monotherapy applying only one of the pharmaceutically therapeutic agents used in a COMBINATION OF THE INVENTION.

A further benefit is that lower doses of the therapeutic agents of the COMBINATION OF THE INVENTION can be used, for example, that the dosages need not only often be smaller, but are also applied less frequently, or can be used in order to diminish the incidence of side-effects observed with one of the combination partners alone. This is in accordance with the desires and requirements of the patients to be treated.

It may be shown by established test models that a COMBINATION OF THE INVENTION results in the beneficial effects described herein before. The person skilled in the art is fully enabled to select a relevant test model to prove such beneficial effects. The pharmacological activity of a COMBINATION OF THE INVENTION may, for example, be demonstrated in a clinical study or in a test procedure, for example as described below.

Suitable clinical studies are, for example, open label, dose escalation studies in patients with a proliferative disease. Such studies may demonstrate in particular the synergism of the therapeutic agents of the COMBINATION OF THE INVENTION. The beneficial effects on proliferative diseases may be determined directly through the results of these studies. Such studies may, in particular, be suitable for comparing the effects of a monotherapy using any one of COMPOUND A, COMPOUND B or COMPOUND C versus the effects of a COMBINATION OF THE INVENTION, or for comparing the effects of dual therapy using any two of COMPOUND A, COMPOUND B or COMPOUND C versus the effects of a COMBINATION OF THE INVENTION.

In one embodiment, the dose of the BRAF inhibitor (COMPOUND A) is escalated until the Maximum Tolerated Dosage is reached, and the MEK inhibitor (COMPOUND B) and the anti-EGFR antibody (COMPOUND C) are each administered as a fixed dose. Alternatively, COMPOUND A and COMPOUND B may be administered as a fixed dose and the dose of COMPOUND C may be escalated until the Maximum Tolerated Dosage is reached. Alternatively, COMPOUND A and COMPOUND C may each be administered as a fixed dose and the dose of COMPOUND B may be escalated until the Maximum Tolerated Dosage is reached.

Each patient may receive doses of the BRAF inhibitor (COMPOUND A) and/or the MEK inhibitor (COMPOUND B) and/or the EGFR inhibitor (COMPOUND C) either daily or intermittently. The efficacy of the treatment may be determined in such studies, e.g., after 6, 12, 18 or 24 weeks by evaluation of symptom scores, e.g., every 6 weeks.

Determining a synergistic interaction between one or more components of a COMBINATION OF THE INVENTION, the optimum range for the effect, and absolute dose ranges of each component for the effect may be definitively measured by administration of the components over different w/w ratio ranges and doses to patients in need of treatment.

In one embodiment, the present invention provides a synergistic combination for human administration for treating a proliferative disease such as cancer comprising (a) a BRAF inhibitor (COMPOUND A) or a pharmaceutically acceptable salt thereof, (b) a MEK inhibitor (COMPOUND B), or a pharmaceutically acceptable salt thereof, and (c) an EGFR inhibitor (COMPOUND C) in a weight:weight:weight combination range, e.g., in a w/w/w range of the combination components, which corresponds to the ranges observed in a tumor model used to identify a synergistic interaction.

In a COMBINATION OF THE INVENTION, the combination partners (COMPOUND A), (COMPOUND B) and (COMPOUND C) can be either administered in a single formulation or unit dosage form, or may administered concurrently but separately as single dosage forms, or may administered sequentially as single unit dosage forms in any order and at specific or non-specific time intervals, by any suitable route. The unit dosage form may also be a fixed combination, for example, of COMPOUND A and COMPOUND B.

COMPOUND A, COMPOUND B and COMPOUND C may be administered as pharmaceutical compositions by any conventional route, in particular enterally, e.g., orally, e.g., in the form of tablets or capsules, parenterally, e.g., in the form of injectable solutions or suspensions, topically, e.g., in the form of lotions, gels, ointments or creams, or in a nasal or suppository form. Pharmaceutical compositions comprising COMPOUND A, COMPOUND B or COMPOUND C in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. For example, compounds of the invention can be formulated into a microemulsion pre concentrate (MEPC).

The unit dosage forms of COMPOUND A, COMPOUND B and COMPOUND C may optionally further comprise additional conventional carriers or excipients used for pharmaceuticals. Examples of such carriers include, but are not limited to, disintegrants, binders, lubricants, glidants, stabilizers, and fillers, diluents, colorants, flavors and preservatives. One of ordinary skill in the art may select one or more of the aforementioned carriers with respect to the particular desired properties of the dosage form by routine experimentation and without any undue burden. The amount of each carriers used may vary within ranges conventional in the art. The following references which are all hereby incorporated by reference disclose techniques and excipients used to formulate oral dosage forms. See *The Handbook of Pharmaceutical Excipients,* 4$^{th}$ edition, Rowe et al., Eds., American Pharmaceuticals Association (2003); and *Remington: the Science and Practice of Pharmacy,* 20$^{th}$ edition, Gennaro, Ed., Lippincott Williams & Wilkins (2003).

These optional additional conventional carriers may be incorporated into the oral dosage form either by incorporating the one or more conventional carriers into the initial mixture before or during granulation or by combining the one or more conventional carriers with granules comprising the combination of agents or individual agents of the combination of agents in the oral dosage form. In the latter embodiment, the combined mixture may be further blended, e.g., through a V-blender, and subsequently compressed or molded into a tablet, for example a monolithic tablet, encapsulated by a capsule, or filled into a sachet.

Examples of pharmaceutically acceptable disintegrants include, but are not limited to, starches; clays; celluloses; alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1% to about 5% by weight of composition.

Examples of pharmaceutically acceptable binders include, but are not limited to, starches; celluloses and derivatives thereof, for example, microcrystalline cellulose, e.g., AVICEL PH from FMC (Philadelphia, Pa.), hydroxypropyl cellulose hydroxylethyl cellulose and hydroxylpropylmethyl cellulose METHOCEL from Dow Chemical Corp. (Midland, Mich.); sucrose; dextrose; corn syrup; polysaccharides; and gelatin. The binder may be present in an amount from about 0% to about 50%, e.g., 2-20% by weight of the composition.

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant may be present in an amount from about 0% to about 10% by weight of the composition. In one embodiment, the lubricant may be present in an amount from about 0.1% to about 1.5% by weight of composition. The glidant may be present in an amount from about 0.1% to about 10% by weight.

Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 0% to about 80% by weight of the composition.

In one embodiment, the BRAF inhibitor (COMPOUND A) is formulated for oral administration.

In one embodiment, the BRAF inhibitor (COMPOUND A) is formulated as a tablet or capsule. Methods of preparing oral formulations of COMPOUND A are described in PCT publication No. WO 2013/078264, which is incorporated herein by reference.

In one embodiment, COMPOUND A is formulated as a solid oral pharmaceutical formulation, which comprises (i) an inner phase which is a solid dispersion comprising amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (COMPOUND A), a hydrophilic binder, a surfactant and (ii) an external phase which comprises an acidifier, a filler, and a lubricant.

In one embodiment of the solid oral formulations of COMPOUND A, the amount of COMPOUND A can be present in the ranges of 1-1500 mg, 2.5-800 mg, or 5-400 mg. In one embodiment, a solid oral formulation comprises 10 mg, 20 mg, 25 mg, 50 mg, 75 mg, 100 mg, 200 mg, 300 mg, 400 mg or 500 mg of COMPOUND A. In one embodiment, a solid oral formulation comprises 50 mg of amorphous COMPOUND A. In one embodiment, a solid oral formulation comprises 75 mg of amorphous COMPOUND A. In one embodiment, the solid oral formulation of amorphous COMPOUND A is formulated as a capsule.

In one embodiment, COMPOUND A is formulated as a solid oral pharmaceutical formulation, which comprises (i) an inner phase which is a solid dispersion comprising amorphous COMPOUND A; copovidone; and poloxamer 188 or sorbitol; and (ii) an external phase which comprises succinic acid, microcrystalline cellulose, crospovidone, colloidal silicon dioxide, and magnesium stearate. In one embodiment, the inner phase comprises from 5% to 40% by weight of amorphous COMPOUND A, from 50% to 80% by weight of copovidone, and from 5% to 20% by weight of poloxamer 188 or sorbitol. In one embodiment, the external phase comprises from 2% to 60% by weight of succinic acid, from 30% to 70% by weight of microcrystalline cellulose, from 5% to 20% by weight of crospovidone, from 0.5% to 5% by weight of colloidal silicon dioxide, and from 0.5% to 5% by weight of magnesium stearate. In one embodiment, the solid oral pharmaceutical formulation comprises a blend of the internal and external phases in a ratio of from 80:20 to 40:60. In one embodiment, the solid oral pharmaceutical formulation comprises a blend of the internal and external phases in a ratio of from 75:25 to 50:50. In one embodiment, the solid oral pharmaceutical formulation comprises 0 mg, 25 mg, 50 mg, 75 mg, or 100 mg of amorphous COMPOUND A. In one embodiment, the solid oral pharmaceutical formulation comprises 10 mg, 25 mg, 50 mg, 75 mg, or 100 mg of amorphous COMPOUND A. In one embodiment, a solid oral formulation comprises 50 mg of amorphous COMPOUND A. In one embodiment, a solid oral formulation comprises 75 mg of amorphous COMPOUND A. In one embodiment, the solid oral pharmaceutical formulation comprises 15% by weight of amorphous COMPOUND A. Pharmaceutical formulations of COMPOUND A are described in PCT publication No. WO 2013/078264.

In one embodiment, the solid oral pharmaceutical formulation of

A)

| Ingredient | % w/w |
|---|---|
| Internal Phase | |
| amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (COMPOUND A) | 15 |
| copovidone | 45 |
| Poloxamer 188 | 5 |
| External Phase | |
| Succinic acid | 13 |
| Microcrystalline cellulose | 16 |
| Crosspovidone | 5 |
| magnesium Stearate | 0.5 |
| Colloidal silicon dioxide | 0.5 |
| Total | 100 | and

B)

| Ingredient | % w/w |
|---|---|
| Internal | |
| amorphous (S)-methyl (1- ((4-(3-(5-chloro-2-fluoro-3-(methylsulfonamido)phenyl)-1-isopropyl-1H-pyrazol-4- yl)pyrimidin-2-yl)amino)propan-2-yl)carbamate (COMPOUND A) | 17 |
| PVP-K30 | 51 |
| Sorbitol | 5 |
| External | |
| Succinic Acid | 9 |
| Microcrystalline cellulose | 12 |
| Crosspovidone | 5 |
| Mg Stearate | 0.5 |
| Colloidal silicon dioxide | 0.5 |
| Total | 100. |

In one embodiment, the solid oral pharmaceutical formulation of amorphous COMPOUND A is selected from:

| Ingredient | (mg) |
|---|---|
| Internal Phase | |
| amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (COMPOUND A) | 10.0 |
| Copovidone | 29.9 |
| Poloxamer 188 | 3.3 |
| External Phase | |
| Succinic acid | 8.7 |
| Cellulose microcrystalline | 10.7 |
| Crospovidone | 3.3 |
| Colloidal silicon dioxide | 0.3 |
| Magnesium Stearate | 0.3 |
| Total (mg) | 66.6, |

| Ingredient | (mg) |
|---|---|
| Internal Phase | |
| amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (COMPOUND A) | 25.0 |
| Copovidone | 74.8 |
| Poloxamer 188 | 8.4 |
| External Phase | |
| Succinic acid | 21.7 |
| Cellulose microcrystalline | 26.7 |
| Crospovidone | 8.4 |
| Colloidal silicon dioxide | 0.9 |
| Magnesium Stearate | 0.9 |
| Total (mg) | 166.5, |

| Ingredient | (mg) |
|---|---|
| Internal Phase | |
| amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (COMPOUND A) | 50.0 |
| Copovidone | 150.0 |
| Poloxamer 188 | 16.7 |
| External Phase | |
| Succinic acid | 43.3 |
| Cellulose microcrystalline | 53.3 |
| Crospovidone | 16.7 |
| Colloidal silicon dioxide | 1.7 |
| Magnesium Stearate | 1.7 |
| Total (mg) | 333.4, | and

| Ingredient | (mg) |
|---|---|
| Internal Phase | |
| amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (COMPOUND A) | 100.0 |
| Copovidone | 300.0 |
| Poloxamer 188 | 33.3 |
| External Phase | |
| Succinic acid | 86.7 |
| Cellulose microcrystalline | 106.7 |
| Crospovidone | 33.3 |
| Colloidal silicon dioxide | 3.3 |
| Magnesium Stearate | 3.3 |
| Total (mg) | 666.6. |

In one embodiment, the solid oral formulation of COMPOUND A is prepared by a process comprising: (i) blending a mixture comprising amorphous COMPOUND A; copovidone; and poloxamer 188 or sorbitol to provide a first blend; (ii) extruding the first blend to provide an extrudate; (iii) milling the extrudate to provide a milled extrudate; (iv) blending the milled extrudate with at least one of succinic acid, microcrystalline cellulose, crospovidone, colloidal silicon dioxide, and magnesium stearate to provide a second blend; (v) optionally repeating step (iv) as needed to provide a third blend comprising the succinic acid, microcrystalline cellulose, crospovidone, colloidal silicon dioxide, magnesium stearate, and the milled extrudate; and (vi) optionally tableting or encapsulating the third blend.

In one embodiment, the MEK inhibitor (COMPOUND B) is formulated for oral administration. In one embodiment, the MEK inhibitor (COMPOUND B) is formulated as a tablet or capsule. In one embodiment, the MEK inhibitor (COMPOUND B) is formulated as a tablet. In one embodiment, the tablet is a coated tablet. In one embodiment, the MEK inhibitor (COMPOUND B) is 6-(4-bromo-2-fluorophenylamino)-7-fluoro-3-methyl-3H-benzoimidazole-5-carboxylic acid (2-hydroxyethoxy)-amide. In one embodiment, the MEK inhibitor (COMPOUND B) is crystallized 6-(4-bromo-2-fluorophenylamino)-7-fluoro-3-methyl-3H-benzoimidazole-5-carboxylic acid (2-hydroxyethoxy)-amide. Methods of preparing oral formulations of 6-(4-bromo-2-fluorophenylamino)-7-fluoro-3-methyl-3H-benzoimidazole-5-carboxylic acid (2-hydroxyethoxy)-amide are described in PCT publication No. WO 2014/063024.

In one embodiment, a pharmaceutical composition of COMPOUND B comprises crystallized COMPOUND B, at least one sugar, and at least one cellulose-derivative excipient. In one embodiment of the pharmaceutical composition provided herein, the pharmaceutical composition comprises about 5-35% crystallized COMPOUND B by weight of composition. In a further embodiment, the pharmaceutical composition comprises about 5-11% crystallized COMPOUND B by weight of composition. In another preferred embodiment, the pharmaceutical composition comprises about 6.25% crystallized COMPOUND B by weight of composition. In another preferred embodiment, the pharmaceutical composition comprises about 10% crystallized COMPOUND B by weight of composition. In another embodiment, the pharmaceutical composition comprises approximately 15 mg or 45 mg crystallized COMPOUND B. In another embodiment, the pharmaceutical composition comprises approximately 15 mg of crystallized COMPOUND B. Suitable sugars for use in the pharmaceutical compositions include, but are not limited to, lactose (e.g., spray-dried lactose, lactose monohydrate), maltose, fructose, galactose, confectioner's sugar, compressible sugar, dextrates, dextrin, dextrose, mannitol, Nu-Tab, Di-Pac, Emdex, and sucrose. In a preferred embodiment, the sugar used in the pharmaceutical composition is lactose, particularly lactose monohydrate. In one embodiment of the pharmaceutical composition provided herein, the pharmaceutical composition comprises about 30-70% of at least one sugar by weight of composition. In a further embodiment, the pharmaceutical composition comprises about 50-60% of lactose by weight of composition. In a further embodiment, the pharmaceutical composition comprises about 50-60% of lactose monohydrate by weight of composition. In a preferred embodiment, the pharmaceutical composition comprises about 55-56% of lactose monohydrate by weight of composition. Suitable cellulose-derivative excipients include, but are not limited to, microcrystalline cellulose, microfine cellulose, powdered cellulose, methyl cellulose, hydroxyethyl cellulose, hydroxymethyl cellulose, hydroxypropyl cellulose, and hydroxypropyl methylcellulose. In a preferred embodiment, the cellulose-based excipient is microcrystalline cellulose. In one embodiment of the pharmaceutical composition provided herein, the pharmaceutical composition comprises about 20-40% cellulose-derivative excipient by weight of composition. In a further embodiment, the pharmaceutical composition comprises about 20-40% microcrystalline cellulose by weight of composition. In a further embodiment, the pharmaceutical composition comprises about 30-40% microcrystalline cellulose by weight of composition. In a one embodiment, the pharmaceutical composition comprises about 30-36% microcrystalline cellulose by weight of composition. In one embodiment, a pharmaceutic composition of COMPOUND B comprises 6-(4-bromo-2-fluorophenylamino)-7-fluoro-3-methyl-3H-benzoimidazole-5-carboxylic acid (2-hydroxyethoxy)-amide. In one embodiment, a pharmaceutic composition of COMPOUND B comprises crystallized 6-(4-bromo-2-fluorophenylamino)-7-fluoro-3-methyl-3H-benzoimidazole-5-carboxylic acid (2-hydroxyethoxy)-amide. In one embodiment, a pharmaceutic composition of COMPOUND B comprises 15 mg of crystallized 6-(4-bromo-2-fluorophenylamino)-7-fluoro-3-methyl-3H-benzoimidazole-5-carboxylic acid (2-hydroxyethoxy)-amide.

The pharmaceutical composition of COMPOUND B can comprise additional excipients or carriers, including but not limited to disintegrants, lubricants, glidants, binders, stabilizers, and fillers, diluents, colorants, flavors and preservatives. One of ordinary skill in the art may select one or more of the aforementioned carriers with respect to the particular desired properties of the dosage form by routine experimentation and without any undue burden. The amount of each carriers used may vary within ranges conventional in the art. The following references which are all hereby incorporated by reference disclose techniques and excipients used to formulate oral dosage forms. See *The Handbook of Pharmaceutical Excipients*, 4th edition, Rowe et al., Eds., American Pharmaceuticals Association (2003); and *Remington: the Science and Practice of Pharmacy*, 20th edition, Gennaro, Ed., Lippincott Williams & Wilkins (2003). These optional additional conventional carriers may be incorporated into the oral dosage form either by incorporating the one or more conventional carriers into the initial mixture or added during the mixing phases.

Examples of pharmaceutically acceptable disintegrants for compositions of COMPOUND B include, but are not limited to, starches; clays; celluloses; alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium (e.g., AC-DI-SOL from FMC); and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1-5%, or about 1-3%, or about 1.5-2.5% by weight of composition.

In one embodiment, the pharmaceutical composition of COMPOUND B includes the disintegrant croscarmellose sodium. In a further embodiment, the pharmaceutical composition of the present invention includes about 2% croscarmellose sodium by weight of composition.

Examples of pharmaceutically acceptable lubricants and pharmaceutically acceptable glidants for compositions of COMPOUND B include, but are not limited to, colloidal silicon dioxide/colloidal anhydrous silica (e.g., Aerosil 200®), magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant may be present in an amount from about 0% to about 10% by weight of the composition. In one embodiment, the lubricant may be present in an amount from about 0.1-1.5%, about 0.1-1%, or about 0.5-0.9% by weight of composition. The glidant may be present in an amount from about 0.1-10%, about 0.1-5%, or about 0.1-1% by weight of composition.

In one embodiment, the pharmaceutical composition of COMPOUND B includes the glidant colloidal silicon dioxide/colloidal anhydrous silica. In a further embodiment, the pharmaceutical composition of COMPOUND B includes about 0.25% (by weight of composition) colloidal silicon dioxide/colloidal anhydrous silica.

In another embodiment, the pharmaceutical composition of COMPOUND B includes the lubricant magnesium stearate. In a further embodiment, the pharmaceutical composition of COMPOUND B includes about 0.75% magnesium stearate by weight of composition.

In another embodiment, the pharmaceutical composition of COMPOUND B includes colloidal silicon dioxide/colloidal anhydrous silica and magnesium stearate. In a further embodiment, the pharmaceutical composition of COMPOUND B includes about 0.25% colloidal silicon dioxide/colloidal anhydrous silica by weight of composition and about 0.75% magnesium stearate by weight of composition.

Examples of pharmaceutically acceptable binders for compositions of COMPOUND B include, but are not limited to, starches; celluloses and derivatives thereof, for example, microcrystalline cellulose, e.g., AVICEL PH from FMC (Philadelphia, Pa.), hydroxypropyl cellulose hydroxyethyl cellulose and hydroxylpropylmethyl cellulose METHOCEL from Dow Chemical Corp. (Midland, Mich.); sucrose; dextrose; corn syrup; polysaccharides; and gelatin. The binder may be present in an amount from about 0-50%, or about 2-20% by weight of the composition.

Examples of pharmaceutically acceptable diluents for compositions of COMPOUND B include, but are not limited to, confectioner's sugar, compressible sugar, dextrates, dextrin, dextrose, lactose, mannitol, microcrystalline cellulose, powdered cellulose, sorbitol, sucrose and talc. The diluent, e.g., may be present in an amount from about 0-80%, or about 0-50%, or about 1-40% or about 1-10% by weight of the composition.

In one embodiment, the pharmaceutical composition of COMPOUND B further comprises one or more of croscarmellose sodium, magnesium stearate, and silicon dioxide.

When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

In one embodiment, the pharmaceutical composition of COMPOUND B comprises about 5-11% crystallized COMPOUND B by weight of composition, about 55-56% lactose monohydrate by weight of composition, and about 30-36% microcrystalline cellulose by weight of composition. In one embodiment, the pharmaceutic composition of COMPOUND B comprises 6-(4-bromo-2-fluorophenylamino)-7-fluoro-3-methyl-3H-benzoimidazole-5-carboxylic acid (2-hydroxyethoxy)-amide.

In one embodiment, the pharmaceutical composition of COMPOUND B comprises about 5-11% of crystallized COMPOUND B, about 55-56% of lactose monohydrate, about 30-36% of microcrystalline cellulose, by weight of composition, about 1.5-2.5% of croscarmellose sodium, about 0.5-0.9% of magnesium stearate, and about 0.1-1% percent colloidal silicon dioxide/colloidal anhydrous silica, by weight of composition. In one embodiment, the pharmaceutic composition of COMPOUND B comprises 6-(4-bromo-2-fluorophenylamino)-7-fluoro-3-methyl-3H-benzoimidazole-5-carboxylic acid (2-hydroxyethoxy)-amide.

In one embodiment, the pharmaceutical composition of COMPOUND B comprises about 5-11% crystallized COMPOUND B by weight of composition, about 55-56% lactose monohydrate by weight of composition, about 30-36% microcrystalline cellulose by weight of composition, about 2% croscarmellose sodium by weight of composition, about 0.75 percent magnesium stearate by weight of composition, and about 0.25 percent colloidal silicon dioxide/colloidal anhydrous silica by weight of composition. In one embodiment, the pharmaceutic composition of COMPOUND B comprises 6-(4-bromo-2-fluorophenylamino)-7-fluoro-3-methyl-3H-benzoimidazole-5-carboxylic acid (2-hydroxyethoxy)-amide.

In one embodiment, the pharmaceutical composition of COMPOUND B comprises 15 mg of crystallized COMPOUND B. In one embodiment, the pharmaceutical composition of COMPOUND B comprises crystalline COMPOUND B, lactose monohydrate, microcrystalline cellulose, colloidal silicon dioxide, croscarmellose sodium, and magnesium stearate. In one embodiment, the pharmaceutic composition of COMPOUND B comprises 6-(4-bromo-2-fluorophenylamino)-7-fluoro-3-methyl-3H-benzoimidazole-5-carboxylic acid (2-hydroxyethoxy)-amide.

In one embodiment, the pharmaceutical composition of COMPOUND B comprises:

| Formulation | | Form 1 (% by weight) | Form 1 (in mg/ unit) | Form 2 (% by weight) | Form 2 (in mg/ unit) |
|---|---|---|---|---|---|
| Tablet core | | | | | |
| Crystallized COMPOUND B | Active agent | 6.25% | 15 | 10.00% | 15.00 |
| Lactose monohydrate | Filler | 55.63% | 133.5 | 55.62% | 83.43 |
| Microcrystalline cellulose | Filler | 35.13% | 84.3 | 31.37% | 47.06 |
| Croscarmellose Sodium | Disintegrant | 2.00% | 4.8 | 2.00% | 3 |
| Magnesium Stearate | Lubricant | 0.75% | 1.8 | 0.75% | 1.13 |
| Colloidal Silicon Dioxide/Silica, colloidal anhydrous(e.g., Aerosil 200 ©) | Glidant | 0.25% | 0.6 | 0.25% | 0.38 |
| TOTAL: | | | 240 | | 150 |
| Tablet coating | | | | | |
| Tablet core (from above) | | 100% | | 100% | |
| Opadry II (Yellow) ® | Film coat | 3.50% | 8.4 | 3.50% | 8.4 |
| Sterile water for irrigation | Solvent | — | | — | |

In one embodiment of the above formulation, the crystallized COMPOUND B is crystallized 6-(4-bromo-2-fluorophenylamino)-7-fluoro-3-methyl-3H-benzoimidazole-5-carboxylic acid (2-hydroxyethoxy)-amide.

In embodiments where the EGFR inhibitor (COMPOUND C) is a tyrosine kinase inhibitor, the compound may be formulated for oral administration.

In embodiments where the EGFR inhibitor (COMPOUND C) is a monoclonal antibody (i.e., an anti-EGFR antibody), the antibody is formulated for intravenous administration. In one embodiment, the anti-EGFR antibody is formulated in a solution with no preservatives, which contains 8.48 mg/mL sodium chloride, 1.88 mg/mL sodium phosphate dibasic heptahydrate, 0.41 mg/mL sodium phosphate monobasic monohydrate, and water for injection.

Also provided is a commercial package comprising as therapeutic agents COMBINATION OF THE INVENTION, together with instructions for simultaneous, separate or sequential administration thereof for use in the delay of progression or treatment of a proliferative disease in a subject in need thereof.

Also provided is commercial package comprising (a) a BRAF inhibitor which is methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate or a pharmaceutically acceptable salt thereof, (b) at least one MEK inhibitor, together with instructions for simultaneous, separate or sequential administration thereof together with (COMPOUND C) in the treatment of a proliferative disease. In one embodiment, the MEK inhibitor is 6-(4-bromo-2-fluorophenylamino)-7-fluoro-3-methyl-3H-benzoimidazole-5-carboxylic acid (2-hydroxyethoxy)-amide or a pharmaceutically acceptable salt thereof. In one embodiment, the anti-EGFR-inhibitor antibody is cetuximab.

The following Examples illustrate the invention described above; they are not, however, intended to limit the scope of the invention in any way. The beneficial effects of the pharmaceutical combination of the present invention can also be determined by other test models known as such to the person skilled in the pertinent art.

Example 1

Anti-Tumor Effects of Triple Combination of LGX818 (Encorafenib; BRAF Inhibitor), MEK162 (Binimetinib: MEK Inhibitor), and Cetuximab (EGFR Inhibitor) in HT-29 CRC Model LGX818 (COMPOUND A), MEK162 (COMPOUND B), and cetuximab (COMPOUND C) were tested in combinations in the HT-29 BRAF mutant colorectal cancer (CRC) xenograft tumor model. LGX818, MEK162 and cetuximab, as single agents, exhibited T/C of 42%, 28%, and 95%, respectively. The combination of LGX818 or MEK162 with cetuximab resulted in T/C of 22%. The triple combination of LGX818, MEK162 and cetuximab led to tumor regression with T/T0 of −14%. These results demonstrated combination benefit of LGX818 with MEK162 and cetuximab in BRAF V600E mutant CRC.

1. Abbreviations

| | |
|---|---|
| ANOVA | Analysis of variance |
| BW | Body weight |
| CLE | Cell line encyclopedia |
| C | Mean tumor size - control group |
| Δ Tumor volume | Delta tumor volume calculated by subtracting final tumor volume from initial tumor volume |
| Δ BW % | Percent body weight difference calculated as ($BW_{final\ day}$ − $BW_{Day\ 0}$)/$BW_{Day\ 0}$ × 100% |
| FBS | Fetal bovine serum |
| PBS | Phosphate-buffered saline |
| kg | Kilogram |
| μL | Microliter |
| mg | milligram |
| mL | Milliliter |
| NS | Not significant |
| TRP | Oncology translational research pharmacology |
| qd | Every day |
| bid | Twice a day |
| 2qw | Twice a week |
| % Reg | % Tumor regression |
| S | Significant |
| Sc | Subcutaneous |
| SEM | Standard Error of the Mean |
| T | Mean tumor size - treated group |
| % T/C | Percent tumor volume change treated over control group |
| PC | Pharmacodynamics |
| CMC | Carboxymethylcellulose |
| CRC | Colorectal cancer |

2. Methods 2.1 Materials

TABLE 1

Animal characteristics

| Species | Strain | Category | Vendor | Gender | Weight | Age |
|---|---|---|---|---|---|---|
| Mouse (Mus musculus) | Nude | Mutant | Harlan | Female | 18-22 g | Adult |

2.1.1 Animals and Maintenance Conditions

For all experiments, nude mice were housed in a 12 hour light/dark cycle facility and had access to food and water ad libitum.

2.1.2 Statement on Animal Welfare

Animals were allowed to acclimate in the Novartis NIBRI animal facility for at least 3 days prior to experimentation. Animals were handled in accordance with Novartis IACUC regulations and guidelines.

2.1.3 Cells and Cell Culture Conditions

HT-29 cells were purchased from ATCC, and master stocks were generated by CLE. Our working stock was obtained from the CLE and cultured in McCoy's 5A medium containing 10% heat-inactivated fetal bovine serum without antibiotics until the time of implantation. Cells tested were free of *mycoplasma* and viral contamination in the IMPACT VIII PCR assay panel (IDEXX RADIL, IDEXX Laboratories INC. Westbrook, Me.). HT-29 cells were at passage 10 for study TRP-377-HT-29-XEF.

2.1.4 Test Compound Formulation

LGX818 was dissolved in 0.5% CMC/0.5% Tween 80. It is stable for at least one week at room temperature; and it was dosed at 20 mg/kg, po, qd×21.

MEK162 was dissolved in 1% CMC/0.5% Tween 80. It is stable for at least one week at room temperature; and it was dosed at 3.5 mg/kg po, bid×21.

Cetuximab (Erbitux) is a product of ImClone LLC, Eli Lilly subsidiary. It is supplied at a concentration of 2 mg/mL. It was dosed at 20 mg/kg ip, 2qw×10.

2.2 Methods 2.2.1 HT-29 Colon Cancer Xenograft Model in Female Nude Mice

HT-29 cells were harvested in exponential growth. Five million cells in 200 μL PBS were subcutaneously implanted into the upper right flank of 112 female nude mice. The tumors reached approximately 200 mm³ at day 22 post cell implantation. On Day 22, tumor-bearing mice were randomized into treatment groups, and treatment started on Day 22 and ended on Day 43. Tumors were monitored for growth after termination of treatment.

2.2.2 Animal Monitoring

Animal wellbeing and behavior, including grooming and ambulation were monitored twice daily. General health of mice was monitored and mortality recorded daily. Any moribund animals were sacrificed.

2.2.3 Exclusion Criteria

Animals were excluded from all final analysis based on the following criteria: (1) euthanized based on morbidity criteria including 20% or greater body weight loss compared to vehicle control, (2) 15% or greater body weight loss on 3 consecutive days compared to vehicle control, or (3) tumor volume greater than or equal to 10% of body weight or tumor ulceration.

Preclinical pharmacology is run on a relatively large scale and it is not uncommon to observe isolated incidents of mortality. This can be due to individual variations within an animal cohort or unknown reasons. Rare and isolated events do not necessarily indicate any increased safety risk to the compound(s) in question. All studies adhere to pre-determined guidelines to define acceptable toxicity for the maximal tolerable dose (MTD).

2.2.4 Efficacy Study Design

The design for TRP-377-HT29-XEF including dose schedule for all treatment groups are summarized in Table 2. Animals were weight at dosing day(s) and dose was body weight adjusted, dosing volume was 10 mL/kg. Tumor dimensions and body weights were collected at the time of randomization and twice weekly thereafter for the study duration. The following data were provided after each day of data collection: incidence of mortality, individual and group average body weights, and individual and group average tumor volume.

TABLE 2

Dose and Schedule for Study TRP-377-HT29-XEF

| Group | Treatment | Dose & Schedule | Number of mice |
|---|---|---|---|
| 1 | Vehicle (1% CMC/ 0.5% Tween 80) IgG control | 10 mL/kg po bid 20 mg/kg ip 2qw | 10 |
| 2 | cetuximab | 20 mg/kg ip 2qw | 10 |
| 3 | LGX818 | 20 mg/kg po qd | 10 |
| 4 | MEK162 | 3.5 mg/kg po bid | 10 |
| 5 | LGX818 MEK162 | 20 mg/kg po qd 3.5 mg/kg po bid | 10 |
| 6 | LGX818 cetuximab | 20 mg/kg po qd 20 mg/kg ip 2qw | 10 |
| 7 | MEK162 cetuximab | 3.5 mg/kg po bid 20 mg/kg ip 2qw | 10 |
| 8 | LGX818 MEK162 cetuximab | 20 mg/kg po qd 3.5 mg/kg po bid 20 mg/kg ip 2qw | 10 |

For Study TRP-377-HT29-XEF, treatments were initiated in day 22 following tumor cell implantation of five million HT29 cells, when the average tumor volume was 220 mm³. Treatments continued for 21 days.

2.2.5 Data Analysis 2.2.5.1 Body Weight

The % change in body was calculated as $(BW_{current} - BW_{initial})/(BW_{initial}) \times 100$. Data is presented as percent body weight change from the day of treatment initiation.

2.2.5.2 Tumor Volume

Percent treatment/control (T/C) values were calculated using the following formulas:

$$\% \, T/C = 100 \times \Delta T/\Delta C \text{ if } \Delta T > 0$$

$$\% \, \text{Regression} = 100 \times \Delta T/T_0 \text{ if } \Delta T < 0$$

where:

T=mean tumor volume of the drug-treated group on the final day of the study or the last day of treatment;

ΔT=mean tumor volume of the drug-treated group on the final day of the study or last day of treatment−mean tumor volume of the drug-treated group on initial day of dosing;

$T_0$=mean tumor volume of the drug-treated group on the day of cohort;

C=mean tumor volume of the control group on the final day of the study or last day of treatment; and ΔC=mean tumor volume of the control group on the final day of the study or last day of treatment−mean tumor volume of the control group on initial day of dosing.

2.2.5.3 Statistical Analysis

All data were expressed as mean±standard error of the mean (SEM). Delta tumor volume and percent body weight changes were used for statistical analysis. Between group comparisons were carried out using the Kruskal-Wallis ANOVA followed by a post hoc Dunn's test. For all statistical evaluations, the level of significance was set at p<0.05. Significance compared to the vehicle control group is reported unless otherwise stated.

The standard protocols used in pharmacology studies are not pre-powered to demonstrate statistically significant superiority of a combination over the respective single agent treatments. The statistical power is often limited by potent single agent responses and/or model variability. The p-values for combination vs. single agent treatments are, however, provided.

3. Results

3.1 Tolerability

Figure 2:
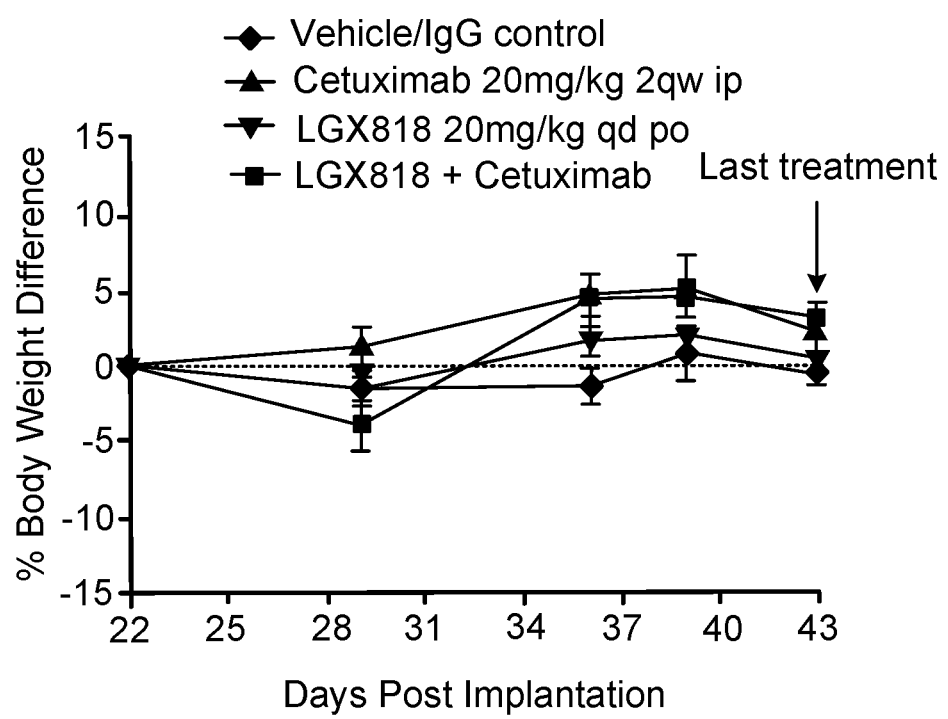
FIG. 2 is a body weight change curve in a HT29 xenograft model following 21 days of vehicle (IgG control), cetuximab, LGX818, and LGX818+cetuximab treatment, presented as tumor volume (mm³) vs. days post implantation, where the closed diamond represent vehicle (IgG control), the closed triangle represents cetuximab, the closed inverted triangle represents LGX818, and the closed square represents LGX818+cetuximab.
Figure 3:
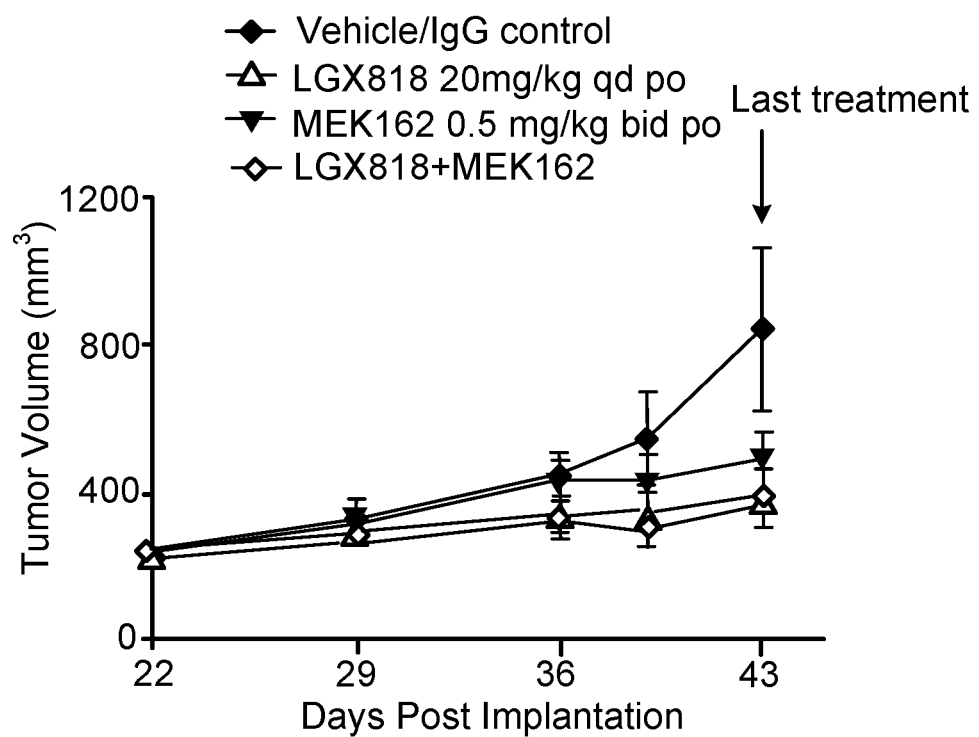
FIG. 3 is a tumor growth curve in a HT29 xenograft model following 21 days of vehicle (IgG control), LGX818, MEK162, and LGX818+MEK162 treatment, presented as tumor volume (mm³) vs. days post implantation, where the closed diamond represent vehicle, the open triangle represents LGX818, the closed inverted triangle represents MEK162, and the open diamond represents LGX818+MEK162.
Figure 4:
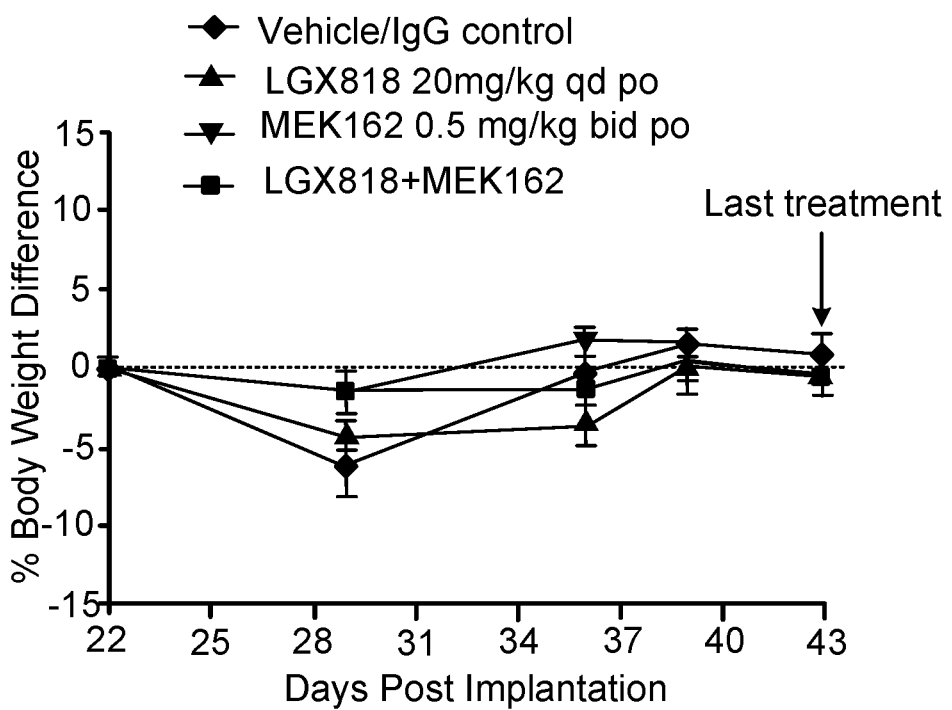
FIG. 4 is a body weight change curve in a HT29 xenograft model following 21 days of vehicle (IgG control), LGX818, MEK162, and LGX818+MEK162 treatment, presented as tumor volume (mm³) vs. days post implantation where the closed diamond represent vehicle (IgG control), the closed triangle represents LGX818, the closed inverted triangle represents MEK162, and the closed square represents LGX818+MEK162.
Figure 5:
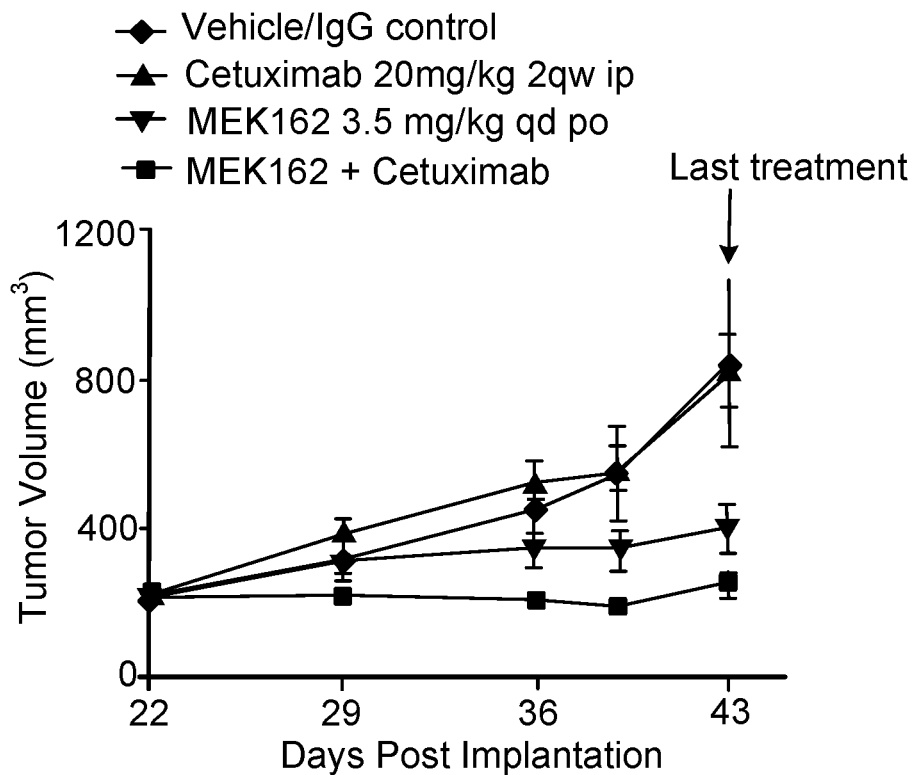
FIG. 5 is a tumor growth curve in a HT29 xenograft model following 21 days of vehicle (IgG control), cetuximab, MEK162, and MEK162+cetuximab treatment, presented as tumor volume (mm³) vs. days post implantation where the closed diamond represent vehicle, (IgG control), the closed triangle represents cetuximab, the closed inverted triangle represents MEK162, and the closed square represents MEK162+cetuximab.
Figure 6:
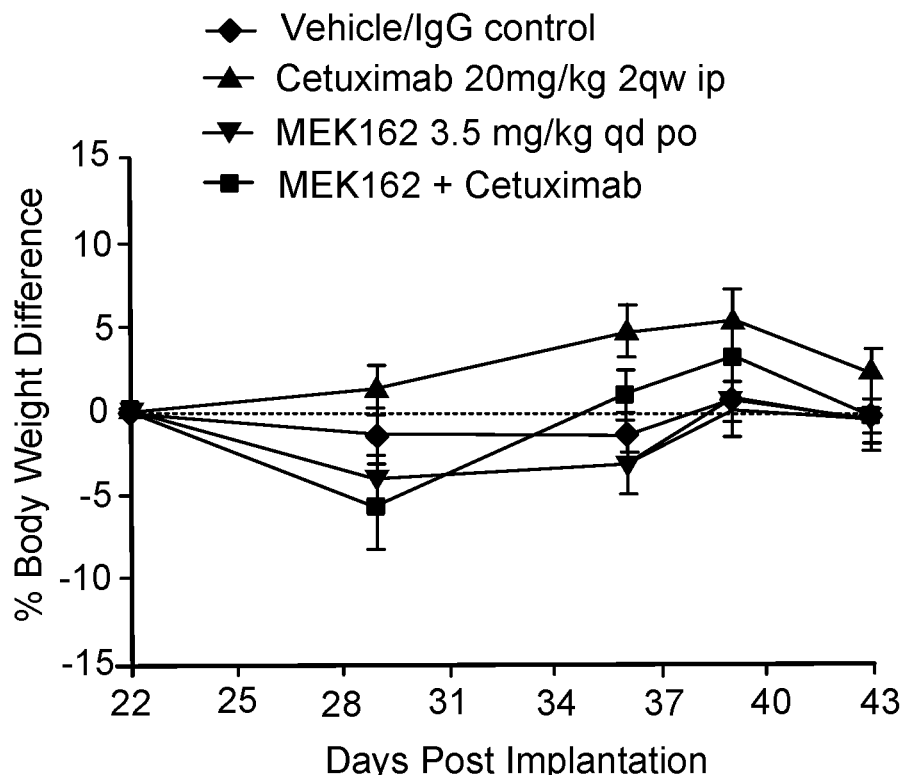
FIG. 6 is a body weight change curve in a HT29 xenograft model following 21 days of vehicle (IgG control), cetuximab, MEK162, and MEK162+cetuximab treatment, presented as tumor volume (mm³) vs. days post implantation, where the closed diamond represent vehicle, (IgG control), the closed triangle represents cetuximab, the closed inverted triangle represents MEK162, and the closed square represents MEK162+cetuximab.

The initial mean body weight (BW) and maximum body weight changes at day 43 are summarized in Table 3. The average body weight change is shown in FIGS. 2, 4 and 6. All treatments were tolerated with maximum body weight loss as −7.7%. No other signs of adverse events were observed in this study.

TABLE 3

Mean initial body weight and maximum body weight change during treatment (TRP-377-HT-29-XEF)

| Group | Treatment | Initial BW (g) mean ± SEM | % Maximum BW change (day) |
|---|---|---|---|
| 1 | Vehicle IgG control | 22.9 ± 0.5 | −1.4 ± 1.3 (day 29) |
| 2 | cetuximab | 22.7 ± 0.6 | 2.3 ± 1.5 (day 43) |
| 3 | LGX818 | 23.4 ± 0.7 | −1.6 ± 0.98 (day 29) |
| 4 | MEK162 | 23.6 ± 0.4 | −4.1 ± 1.02 (day 29) |
| 5 | LGX818 MEK162 | 23.8 ± 0.5 | −6.2 ± 1.9 (day 29) |
| 6 | LGX818 cetuximab | 23.3 ± 0.2 | −3.9 ± 1.6 (day 29) |
| 7 | MEK162 cetuximab | 23.4 ± 0.5 | −5.9 ± 2.3 (day 29) |
| 8 | LGX818 MEK162 cetuximab | 23.6 ± 0.5 | −7.7 ± 1.3 (day 29) |

3.2 In Vivo Efficacy

Anti-tumor effects and percent body weight changes on day 43 are illustrated in FIGS. 1-6.

LGX818 at 20 mg/kg, MEK162 at 3.5 mg/kg, and cetuximab at 20 mg/kg produced statistically non-significant anti-tumor effects with T/C 42%, 28%, and 95% respectively. LGX818 in combination with MEK162 resulted in T/C 22% (p>0.05 vs. vehicle treated group); LGX818 in combination with cetuximab resulted in T/C 6% (p<0.05 vs. vehicle or cetuximab treated groups); MEK162 in combination with cetuximab resulted in T/C 5% (p<0.05 vs. vehicle or cetuximab treated groups). The Triple combination of LGX818+MEK162+cetuximab led to tumor regression with T/T0 −14%. The Triple combination treatment is statistically significant (p<0.05), when compared with vehicle, LGX818 or cetuximab monotherapy.

Figure 7:
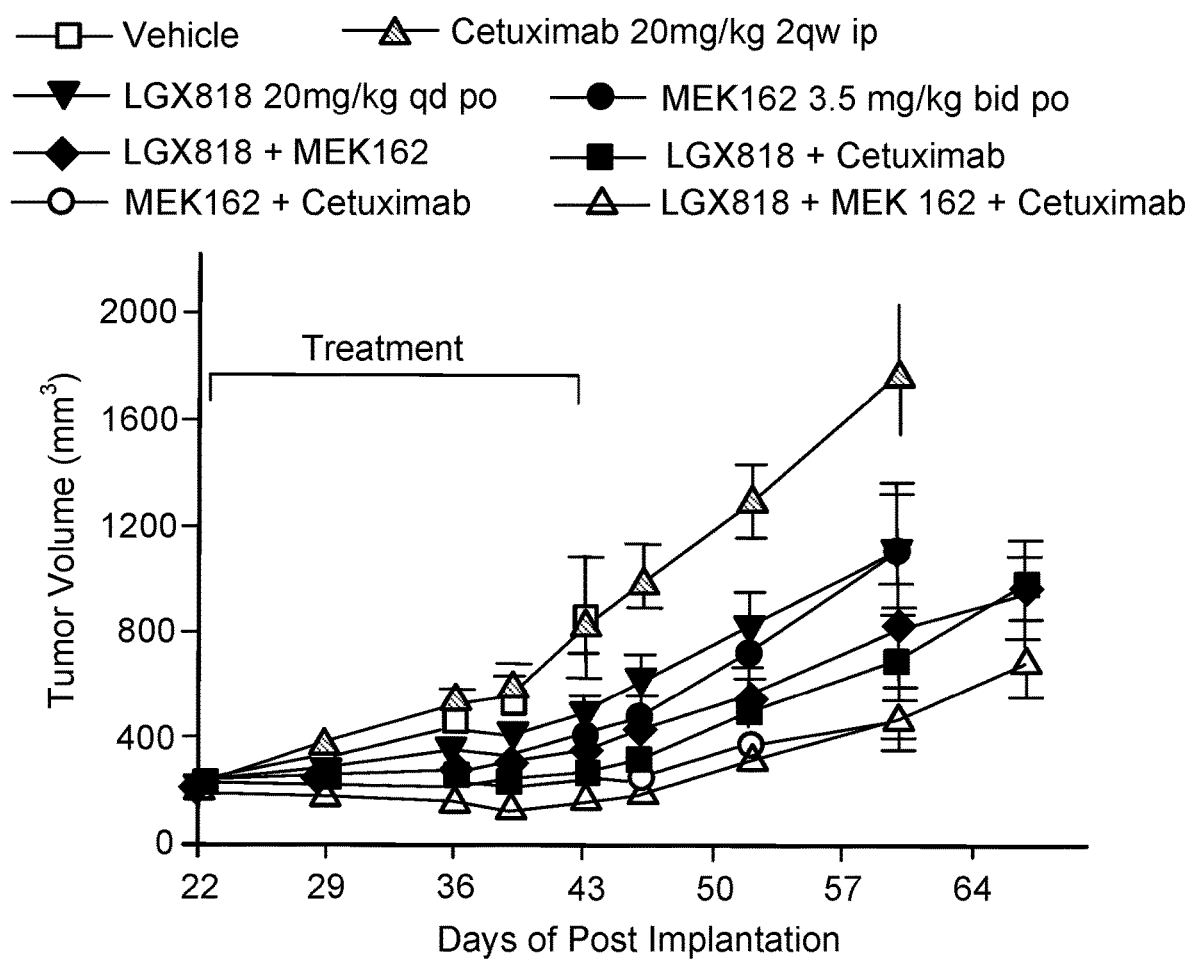
FIG. 7 is tumor re-growth curve in a HT29 xenograft model following termination of vehicle (IgG control), cetuximab, LGX818, MEK162, LGX818+MEK162, LGX818+cetuximab, MEK162+cetuximab, and LGX818+MEK162+cetuximab treatment, presented as tumor volume (mm³) vs. days post implantation where the open square represents vehicle, the hashed triangle represents cetuximab, the closed inverted triangle represents LGX818, the closed circle represents MEK162, the closed diamond represents LGX818+MEK162, the closed square represents LGX818+cetuximab, the open circle represents MEK162+cetuximab, and the open triangle represents LGX818+MEK162+cetuximab.

The last dose was given on day 43, and tumors were monitored for an additional 3 weeks. After termination of treatment, tumors resumed growth in all the treatment groups (FIG. 7), which suggests that continuous treatment is necessary to achieve sustained anti-tumor efficacy.

REFERENCES

Flaherty K T, Puzanov I, Kim K B, Ribas A, McArthur G A, Sosman J A, O'Dwyer P J, Lee R J, Grippo J F, Nolop K, Chapman P B. Inhibition of mutated, activated BRAF in metastatic melanoma. N Engl J Med. 2010 Aug. 26; 363(9), 809-19.

Kefford R, Arkenau H, Brown J P, et al. Phase I/II study of GSK118436, a selective inhibitor of oncogenic mutant BRAF kinase, in patients with metastatic melanoma and other solid tumours. J Clin Oncol. 2010; 28(15s); abstr 8503.

Prahallad A. Sun C. Huang S, Di Nicolantonio F, Salazar R, Zecchin D, Beijersbergen R L, Bardelli A, Bernards R. Unresponsiveness of colon cancer to BRAF(V600E) inhibition through feedback activation of EGFR. Nature. 2012 Jan. 26; 483 (7387):100-3.

Corcoran R B, Ebi H, Turke A B, Coffee E M, Nishino M, Cogdill A P, Brown R D, Della Pelle P, Dias-Santagata D, Hung K E, Flaherty K T, Piris A, Wargo J A, Settleman J, Mino-Kenudson M, Engelman J A. EGFR-mediated re-activation of MAPK signaling contributes to insensitivity of BRAF mutant colorectal cancers to RAF inhibition with vemurafenib. Cancer Discov. 2012 March; 2(3):227-35.

Example 2

Clinical Trial of Encorafenib (BRAF Inhibitor), Binimetinib (MEK Inhibitor), and Cetuximab (EGFR Inhibitor) in Patients with BRAF-Mutant Metastatic Colorectal Cancer (CRC)

Summary: This trial is a randomized, open-label, Phase 3 global study designed to demonstrate the efficacy and safety of encorafenib (COMPOUND A), binimetinib (COMPOUND B), and cetuximab (COMPOUND C) in patients with BRAF-mutant CRC (BRAF$^{V600E}$) who have previously received first-line systemic anticancer therapy. Patients in the trial are at least 18 years of age, have stage IV CRC with confirmed BRAF mutation, have received either one or two regimens of systemic anticancer therapy in the locally advanced or metastatic setting, and have not received prior therapy with a MEK, BRAF or EGFR inhibitor.

Patients are randomized 1:1:1 to receive triplet therapy (binimetinib, encorafenib and cetuximab), doublet therapy (encorafenib and cetuximab) or the control arm (irinotecan-based therapy and cetuximab).

The primary endpoint of the trial is overall survival (OS) of the triplet therapy compared to the control arm. The secondary endpoints address efficacy of the doublet therapy compared to the control arm, and the triplet therapy compared to the doublet therapy. Other key secondary endpoints include progression-free survival (PFS), objective response rate (ORR), duration of response, safety and tolerability. Health related quality of life data will also be assessed.

List of Abbreviations and Definition of Terms

| Abbreviation or special term | Explanation |
|---|---|
| AE | adverse event |
| ALT | alanine aminotransferase |
| ANC | absolute neutrophil count |
| AST | aspartate aminotransferase |
| AUC | area under the concentration-time curve |
| BID | twice daily |
| BRAF | B-RAF proto-oncogene, serine/threonine kinase |
| BRAF$^{V600E}$ | B-RAF proto-oncogene, serine/threonine kinase V600E-mutant |
| BRAF$^{wt}$ | B-RAF proto-oncogene, serine/threonine kinase wild-type |
| BSA | body surface area |
| CI | confidence interval |
| CK | creatine kinase |
| $C_{max}$ | maximum concentration |
| CR | complete response |
| CRC | colorectal cancer |
| CTCAE | Common Terminology Criteria for Adverse Events |

| Abbreviation or special term | Explanation |
|---|---|
| CYP | cytochrome P450 |
| DLT | dose-limiting toxicity |
| DMC | Data Monitoring Committee |
| DOR | duration of response |
| $EC_{50}$ | half maximal effective concentration |
| ECG | electrocardiogram |
| ECHO | echocardiogram |
| ECOG | Eastern Cooperative Oncology Group |
| ECOG PS | Eastern Cooperative Oncology Group performance status |
| EGFR | epidermal growth factor receptor |
| EORTC | European Organization for Research and Treatment of Cancer |
| EQ-5D-5L | EuroQol-5D-5L |
| FA | folinic acid |
| FACT-C | Functional Assessment of Cancer Therapy-Colon Cancer |
| FDA | United States Food and Drug Administration |
| FOLFIRI | 5-fluorouracil/folinic acid/irinotecan |
| FOLFOX | 5-fluorouracil/folinic acid/oxaliplatin |
| FOLFOXIRI | 5-fluorouracil/folinic acid/oxaliplatin/irinotecan |
| 5-FU | 5-fluorouracil |
| GI | gastrointestinal |
| hCG | human chorionic gonadotropin |
| HFSR | rash, hand foot skin reaction |
| HIV | human immunodeficiency virus |
| $IC_{50}$ | half maximal inhibitory concentration |
| IV | intravenous(ly) |
| KA | keratoacanthoma |
| KRAS | V-Ki-ras2 Kirsten rat sarcoma viral oncogene homolog |
| LLN | lower limit of the normal reference range |
| LVEF | left ventricular ejection fraction |
| mCRC | metastatic colorectal cancer |
| MRI | magnetic resonance imaging |
| MTD | maximum tolerated dose |
| MUGA | multi-gated acquisition |
| NCI | National Cancer Institute |
| NGS | next generation sequencing |
| OCT | optical coherence tomography |
| OC$\underline{T}$ | organic cationic transporter |
| ORR | objective response rate (overall response rate) |
| OS | overall survival |
| PCR | polymerase chain reaction |
| PFS | progression-free survival |
| PGIC | Patient Global Impression of Change |
| PK | pharmacokinetic(s) |
| PO | oral(ly) |
| PR | partial response |
| QD | once daily |
| QLQ-C30 | Quality of Life Questionnaire for Cancer Patients |
| QoL | quality of life |
| QTc | corrected QT interval |
| QTcF | QT interval corrected for heart rate using Fridericia's formula |
| RECIST | Response Evaluation Criteria in Solid Tumors |
| RVO | retinal vein occlusion |
| SCC | squamous cell carcinoma |
| $t_{1/2}$ | terminal half-life |
| UGT | UDP-glucuronosyl transferase |
| ULN | upper limit of normal |
| wt | wild-type |

Safety Lead-in Phase

The primary objective of the Safety Lead-in Phase will be to assess the safety/tolerability of the combination of encorafenib+binimetinib+cetuximab. The primary endpoints are:

incidence of dose-limiting toxicities (DLT's)

Incidence and severity of adverse events (AEs) graded according to the National Cancer Institute (NCI) Common Terminology Criteria for Adverse Events (CTCAE), version 4.03, and changes in clinical laboratory parameters, vital signs, electrocardiograms, echocardiogram/multi-gated acquisition scans and ophthalmic examinations Incidence of dose interruptions, dose modifications and discontinuations due to Adverse Events (AEs)

The Safety Lead-in will be conducted at a limited number of sites. Dose-limiting toxicities will be evaluated and the tolerability of the binimetinib, encorafenib, and cetuximab combination will be assessed by the Sponsor and the Investigator in (approximately) weekly communications. The Data Monitoring Committee (DMC) will evaluate the safety data at pre-specified intervals and at additional points during the conduct of the Safety Lead-in, if necessary. The first 9 evaluable patients will be enrolled on a rolling basis in a single cohort to evaluate the combination of encorafenib 300 mg once daily (QD)+binimetinib 45 mg twice daily (BID)+cetuximab 400 mg/m$^2$ followed by 250 mg/m$^2$ IV weekly. Additional patients will be enrolled based on assessments of the safety data by the DMC during the Safety Lead-in. The doses for the Triplet Arm in the randomized Phase 3 portion of the study will be determined after a total of 25-30 patients have been treated at the proposed doses and their data evaluated by the DMC.

Randomized Phase 3 Study

The primary objective of the Randomized Phase 3 study will be to compart the activity of encorafenib+binimetinib+cetuximab (Triplet Arm) vs. Irinotecan/cetuximab or 5-fluorouracil (5-FU)/folinic acid (FA)/irinotecan (FOLFIRI)/cetuximab (Control Arm) as measured by overall survival (OS). The primary endpoint is Overall Survival (OS), defined as the time from randomization to death due to any cause, of Triplet Arm vs. Control Arm. A key secondary endpoint is Overall Survival (OS) of encorafenib+binimetinib (Doublet Arm) vs. Control Arm. Other secondary endpoints are:

Confirmed objective response rate (ORR) per RECIST (Response Evaluation Criteria in Solid Tumors), v1.1 of Triplet Arm vs. Control Arm, defined as the number of patients achieving an overall best response of complete response (CR) or partial response (PR) divided by the total number of patients Confirmed objective response rate (ORR) per RECIST, v1.1 of Doublet Arm vs. Control Arm, defined as the number of patients achieving an overall best response of complete response (CR) or partial response (PR) divided by the total number of patients Investigator-determined progression-free survival (PFS), defined as the time from randomization to the earliest documented disease progression or death due to any cause, of Triplet Arm vs. Control Arm Investigator-determined progression-free survival (PFS) of Doublet Arm vs. Control Arm Overall Survival (OS) of Triplet Arm vs. Doublet Arm Confirmed ORR per RECIST, v1.1 of Triplet Arm vs. Doublet Arm PFS of Triplet Arm vs. Doublet Arm Duration of Response (DOR) of Triplet Arm vs. Control Arm, of Doublet Arm vs. Control Arm and of Triplet Arm vs. Doublet Arm Time to response, defined as the time from randomization to first radiographic evidence of response, of Triplet Arm vs. Control Arm, of Doublet Arm vs. Control Arm and of Triplet Arm vs. Doublet Arm Incidence and severity of AEs, graded according to NCI CTCAE, v.4.03, and changes in clinical laboratory parameters, vital signs, ECGs, ECHO/MUGA scans and ophthalmic examinations Change from baseline in the European Organization for Research and Treatment of Cancer (EORTC) Quality of Life Questionnaire for Cancer Patients (QLQ-C30), Functional Assessment of Cancer Therapy-Colon Cancer (FACT-C), EuroQol-5D-5L (EQ-5D-5L), and Patient Global Impression of Change (PGIC) of Triplet Arm vs. Control Arm, of Doublet Arm vs. Control Arm and of Triplet Arm vs. Doublet Arm Model-based PK parameters of encorafenib, cetuximab, binimetinib and the active metabolite of binimetinib Model-based PK assessment of drug-drug interactions between encorafenib, cetuximab, binimetinib and the active metabolite of binimetinib (AR00426032)

Treatment will be administered in 28-day cycles until disease progression, unacceptable toxicity, withdrawal of consent, initiation of subsequent anticancer therapy or death.

BRAF Testing

Patients will be eligible for the study based on identification of a $BRAF^{V600E}$ mutation in the tumor as determined by the central laboratory as part of the Molecular Prescreening for the trial or by a local assay result obtained any time prior to Screening.

Molecular Prescreening

Prior to eligibility assessment for study enrollment/randomization, patients may undergo molecular tumor prescreening with the central laboratory BRAF mutation assay at any time prior to Screening as long as they meet all the Molecular Prescreening inclusion/exclusion criteria.

Population a) Patient Population

The study will be conducted in patients with $BRAF^{V600E}$ metastatic colorectal cancer (mCRC) whose disease has progressed after 1 or 2 prior regimens in the metastatic setting.

b) Inclusion Criteria

All the following inclusion criteria must be met for a patient to be included in the study:

1. Provide a signed and dated Screening informed consent document
2. Age ≥18 years at time of informed consent
3. Histologically- or cytologically-confirmed CRC that is metastatic
4. Presence of $BRAF^{V600E}$ in tumor tissue previously determined by a local assay at any time prior to Screening or by the central laboratory Notes:
   a. Only PCR and NGS-based local assays results will be acceptable.
   b. Central testing cannot be repeated to resolve discordances with a local result once the central laboratory delivers a definitive result (positive or negative).
   c. If the result from the central laboratory is indeterminate or the sample is deemed is inadequate for testing, a second sample may be submitted.
   d. If at any time there is discordance in the results between the local assay and the central laboratory (potential false-positive local result), or lack of $BRAF^{V600E}$ confirmation in 18 patients, all subsequent patients will be required to have $BRAF^{V600E}$ determined by the central laboratory prior to enrollment.
   e. Results from local laboratories with more than 1 discordant result leading to patient enrollment will not be accepted for further patient enrollment.
5. Able to provide a sufficient amount of representative tumor specimen (primary or metastatic, archival or newly obtained) for confirmatory central laboratory testing of BRAF and KRAS mutation status (minimum of 6 slides; optimally up to 15 slides)
   Note: Tumor samples must be submitted to the central laboratory for BRAF testing as soon as possible following the signing of the Molecular Prescreening informed consent. The BRAF status must be confirmed no later than 30 days following first dose of study drug.
6. Eligible to receive cetuximab per locally approved label with regard to tumor RAS status
7. Progression of disease after 1 or 2 prior regimens in the metastatic setting Notes:
   a. Disease relapse during treatment or within 6 months following adjuvant therapy will be considered metastatic disease.
   b. Patients who have received 2 prior regimens (i.e. those entering the study in the $3^{rd}$ line setting), must have received or have been offered prior oxaliplatin unless it was contraindicated due to underlying conditions.
   c. Maintenance therapy given in the metastatic setting will not be considered a separate regimen.
   d. In the Phase 3 portion of study, the number of patients having received 2 prior regimens will be limited to 215 (35% of the total randomized). Patients with 2 prior regimens who have entered Screening at the time that the limit has been reached will be permitted to continue into the study if they are otherwise determined to be eligible.
8. Evidence of measurable or evaluable non-measurable disease per RECIST, v1.1
9. ECOGPS of 0 or 1
10. Adequate bone marrow function characterized by the following at screening:
    a. Absolute neutrophil count (ANC) $≥1.5×10^9$/L;
    b. Platelets $≥100×10^9$/L;
    c. Hemoglobin ≥9.0 g/dL
       Note: Transfusions will be allowed to achieve this. Transfusions will be permitted provided the patient has not received more than 2 units red blood cells in the prior 4 weeks to achieve this criteria.
11. Adequate renal function characterized by serum creatinine ≤1.5× upper limit of normal (ULN), or calculated by Cockroft-Gault formula or directly measured creatinine clearance ≥50 mL/min at screening
12. Adequate hepatic function characterized by the following at screening:
    a. Serum total bilirubin ≤1.5×ULN and <2 mg/dL
       Note: Patients who have a total bilirubin level >1.5× ULN will be allowed if their indirect bilirubin level is ≤1.5×ULN
    b. Alanine aminotransferase (ALT) and/or aspartate aminotransferase (AST) ≤2.5×ULN, or ≤5×ULN in presence of liver metastases
13. Adequate cardiac function characterized by the following at screening:
    a. Left ventricular ejection fraction (LVEF) ≥50% as determined by a MUGA scan or ECHO;
    b. Mean triplicate QT interval corrected for heart rate using Fridericia's formula (QTcF) value ≤480 msec
14. Able to take oral medications
15. Willing and able to comply with scheduled visits, treatment plan, laboratory tests and other study procedures
16. Female patients are either postmenopausal for at least 1 year, are surgically sterile for at least 6 weeks, or must agree to take appropriate precautions to avoid pregnancy from screening through follow-up if of childbearing potential For all females, the pregnancy test result must be negative at screening. Note: Permitted contraceptive methods should be communicated to the patients and their understanding confirmed.
17. Males must agree to take appropriate precautions to avoid fathering a child from screening through follow-up.
Note: Permitted contraceptive methods should be communicated to the patients and their understanding confirmed.

c) Exclusion Criteria

Patients meeting any of the following criteria will not be included in the study:
1. Prior treatment with any RAF inhibitor, MEK inhibitor, cetuximab, panitumumab or other EGFR inhibitors
2. Prior irinotecan hypersensitivity or toxicity that would suggest an inability to tolerate irinotecan 180 mg/m$^2$ every 2 weeks
3. Symptomatic brain metastasis
   Notes: Patients previously treated or untreated for this condition who are asymptomatic in the absence of corticosteroid and anti-epileptic therapy are allowed. Brain metastases must be stable for ≥4 weeks, with imaging (e.g., magnetic resonance imaging [MRI] or computed tomography [CT]) demonstrating no current evidence of progressive brain metastases at screening.
4. Leptomeningeal disease
5. History or current evidence of RVO or current risk factors for RVO (e.g., uncontrolled glaucoma or ocular hypertension, history of hyperviscosity or hypercoagulability syndromes)
6. Use of any herbal medications/supplements or any medications or foods that are strong inhibitors or inducers of cytochrome P450 (CYP) 3A4/5≤1 week prior to the start of study treatment
7. Known history of acute or chronic pancreatitis
8. History of chronic inflammatory bowel disease or Crohn's disease requiring medical intervention (immunomodulatory or immunosuppressive medications or surgery) ≤12 months prior to randomization
9. Impaired cardiovascular function or clinically significant cardiovascular diseases, including any of the following:
   a. History of acute myocardial infarction, acute coronary syndromes (including unstable angina, coronary artery bypass graft [CABG], coronary angioplasty or stenting)≤6 months prior to start of study treatment;
   b. Symptomatic congestive heart failure (i.e., Grade 2 or higher), history or current evidence of clinically significant cardiac arrhythmia and/or conduction abnormality ≤6 months prior to start of study treatment, except atrial fibrillation and paroxysmal supraventricular tachycardia
10. Uncontrolled hypertension defined as persistent systolic blood pressure ≥150 mmHg or diastolic blood pressure ≥100 mmHg despite current therapy
11. Impaired hepatic function, defined as Child-Pugh class B or C
12. Impaired gastrointestinal (GI) function or disease that may significantly alter the absorption of encorafenib or binimetinib (e.g., ulcerative diseases, uncontrolled vomiting, malabsorption syndrome, small bowel resection with decreased intestinal absorption)
13. Concurrent or previous other malignancy within 5 years of study entry, except cured basal or squamous cell skin cancer, superficial bladder cancer, prostate intraepithelial neoplasm, carcinoma in-situ of the cervix, or other noninvasive or indolent malignancy without Sponsor approval
14. History of thromboembolic or cerebrovascular events ≤6 months prior to starting study treatment, including transient ischemic attacks, cerebrovascular accidents, deep vein thrombosis or pulmonary emboli
15. Concurrent neuromuscular disorder that is associated with the potential of elevated CK (e.g., inflammatory myopathies, muscular dystrophy, amyotrophic lateral sclerosis, spinal muscular atrophy)
16. Treatment with any of the following:
    a. Cyclical chemotherapy within a period of time that was shorter than the cycle length used for that treatment (e.g., 6 weeks for nitrosourea, mitomycin-C) prior to starting study treatment
    b. Biologic therapy (e.g., antibodies) except bevacizumab or aflibercept, continuous or intermittent small molecule therapeutics, or any other investigational agents within a period of time that is ≤5 half-lives ($t_{1/2}$) or ≤4 weeks (whichever is shorter) prior to starting study treatment
    c. Bevacizumab or aflibercept therapy ≤3 weeks prior to starting study treatment
    d. Radiation therapy that included >30% of the bone marrow
17. Residual CTCAE ≥Grade 2 toxicity from any prior anticancer therapy, with the exception of Grade 2 alopecia or Grade 2 neuropathy
18. Known history of HIV infection
19. Active hepatitis B or hepatitis C infection
20. Known history of Gilbert's syndrome or is known to have any of the following genotypes: UGT1A*6/*6, UGT1A1*28/*28, or UGT1A*6/*28.
21. Known contraindication to receive cetuximab or irinotecan at the planned doses.
22. Current treatment with a non-topical medication known to be a strong inhibitor of CYP3A4. However, patients who either discontinue this treatment or switch to another medication at least 7 days prior to starting study treatment are eligible.
23. Concomitant use of St. John's Wort (*Hypericum perforatum*).
24. Other severe, acute or chronic medical or psychiatric condition or laboratory abnormality that may increase the risk associated with study participation or study drug administration or that may interfere with the interpretation of study results and, in the judgment of the Investigator, would make the patient an inappropriate candidate for the study.
25. Pregnant, confirmed by a positive human chorionic gonadotropin (hCG) laboratory test result, or nursing (lactating).
26. Persons under guardianship or temporary guardianship are to be excluded unless participation is required to be offered in the local jurisdiction according to local laws or regulations.
27. Prior enrollment into this clinical study.

Treatment Regimens

The investigational products in this study are encorafenib (COMPOUND A) and binimetinib (COMPOUND B), which will be administered orally (PO) in combination with cetuximab (COMPOUND C) (i.e., encorafenib+binimetinib+cetuximab [Safety Lead-in and Triplet Arm] and encorafenib+cetuximab [Doublet Arm]). The comparator combination treatment will be the Investigator's choice of either irinotecan/cetuximab or FOLFIRI/cetuximab (Control Arm).

Patients will receive the following per 28-day cycle. Starting doses and Treatment Schedule are shown in Table 5.

TABLE 5

| Study Treatments | Pharmaceutical Form and Route of Administration | Dose | Frequency |
|---|---|---|---|
| Safety Lead-in and Triplet Arm | | | |
| Encorafenib | 4 × 75 mg oral capsule | 300 mg | QD |
| Binimetinib | 3 × 15 mg oral film-coated tablet | 45 mg | BID |
| Cetuximab | IV infusion | 400 mg/m$^2$ initial dose (120-minute infusion), then 250 mg/m$^2$ (60-minute infusion) thereafter | once weekly |
| Doublet Arm | | | |
| Encorafenib | 4 × 75 mg oral capsule | 300 mg | QD |
| Cetuximab | IV infusion | 400 mg/m$^2$ initial dose (120-minute infusion), then 250 mg/m$^2$ (60-minute infusion) thereafter | once weekly |
| Control Arm Irinotecan/ Cetuximab | | | |
| Irinotecan | IV infusion | 180 mg/m$^2$ (90-minute infusion or as per institutional standards) | every 2 weeks |
| Cetuximab | IV infusion | 400 mg/m$^2$ initial dose (120-minute infusion), then 250 mg/m$^2$ (60-minute infusion) thereafter | once weekly |
| FOLFIRI/ Cetuximab | | | |
| Irinotecan | IV infusion | 180 mg/m$^2$ (90-minute infusion or as per institutional standards) | every 2 weeks |
| Folinic acid[a] | IV infusion | 400 mg/m$^2$ (120-minute infusion or as per institutional standards) or maximal dose tolerated in a prior regimen | every 2 weeks |
| 5-FU[a] | IV bolus/IV infusion | 400 mg/m$^2$ initial dose bolus (not to exceed 15 minutes), then 1200 mg/m$^2$/day × 2 days (total 2400 mg/m$^2$ over 46-48 hours) continuous infusion or maximal dose tolerated in a prior regimen | every 2 weeks |
| Cetuximab | IV infusion | 400 mg/m$^2$ initial dose (120-minute infusion), then 250 mg/m$^2$ (60-minute infusion) thereafter | once weekly |

[a]Patients who experienced unacceptable toxicities requiring 5-FU and FA dose reductions in prior regimens (e.g. as part of FOLFOX or FOLFOXIRI regimens) may be initiated at the highest doses which were previously tolerated.

For an individual patient, the dose of study drug(s) may be reduced or interrupted as appropriate based on protocol-defined treatment modifications.

Administration of Encorafenib or Encorafenib+Binimetinib

Encorafenib will be administered on a QD schedule and binimetinib will be administered on a BID schedule, both PO as a flat-fixed dose, and not by body weight or body surface area (BSA) (Table 5). Binimetinib and encorafenib should be taken without regard to food. Patients are instructed to swallow the capsules/tablets whole and not to chew or crush them.

QD Dosing: Patients are instructed to take encorafenib capsules daily with a large glass of water (~250 mL) in the morning at approximately the same time every day. Doses of encorafenib that are omitted for AEs or any other reason can be taken up to 12 hours prior to the next dose.

BID Dosing: Patients are instructed to take binimetinib tablets 12±2 hours apart with a large glass of water (~250 mL) in the morning and in the evening at approximately the same times every day. Doses of binimetinib that are omitted for AEs or any other reason should not be made up later in the day, or at the end of the dosing period.

In the Safety Lead-in and Triplet Arm, both oral study drugs (encorafenib+binimetinib) are to be taken together in the morning and only the BID administered drug (binimetinib) is to be taken in the evening without regard to food.

On days when a blood collection is scheduled at the investigational site, patients will take the morning dose of encorafenib and binimetinib (as applicable) at the site, after the collection, under the supervision of the Investigator or designee. On the evening of the visit day, patients will take binimetinib (as applicable) at home (Safety Lead-in and Triplet Arm). On all other days, patients will take encorafenib and binimetinib (as applicable) at home. Pre-dose PK samples for encorafenib and binimetinib analysis should be collected just prior to intake of encorafenib and binimetinib (as applicable).

If a patient vomits at any time after dosing, the dose of study drug should not be re-administered.

Patients must avoid consumption of grapefruit, pomegranates, star fruits, Seville oranges or products containing the juice of each during the entire study and preferably 7 days before the first dose of study drugs, due to potential CYP3A4 interaction with the study drugs. Orange juice is allowed.

Encorafenib and binimetinib (if applicable) will be administered at least 30 minutes prior to cetuximab.

Administration of Cetuximab

Cetuximab will be administered IV weekly on Days 1, 8, 15 and 22 (+3 days) of every 28-day cycle at the study site (Table 5) according to institutional standards. The initial cetuximab dose (Cycle 1 Day 1) is 400 mg/m$^2$ administered as a 120-minute IV infusion followed thereafter by a 250 mg/m$^2$ dose administered as a 60-minute IV infusion. The infusion rate should be consistent with the local label but should not exceed 10 mg/min. Close monitoring is required during the infusion and for at least 1 hour after the end of the infusion. If an infusion reaction occurs while cetuximab is being administered, the infusion should be stopped immediately, and the patients should be closely monitored and treated in line with institutional standards. Pre-medications for routine cetuximab infusions may be used in accordance with the label and with the national and/or institutional standards. Pre-medications should be administered no sooner than 1 hour after administration of encorafenib and binimetinib (if applicable) and 30 minutes prior to cetuximab infusion.

Administration of Irinotecan

Irinotecan will be administered IV biweekly on Days 1 and 15 (+3 days) of every 28-day cycle at the study site according to institutional standards. The initial irinotecan dose (Cycle 1 Day 1) is 180 mg/m² administered as a 90-minute IV infusion or as per institutional standards.

Administration of FOLFIRI

The starting doses of 5-FU, FA and irinotecan are provided in Table 55. Patients who required 5-FU and FA dose reductions in prior regimens (e.g., as part of FOLFOX or FOLFOXIRI regimens) should be initiated at the doses listed in Table 5 which most closely approximate, without exceeding, the previously tolerated dose. In these circumstances, the starting irinotecan dose should not be reduced.

Folinic acid will be administered IV biweekly on Days 1 and 15 (+3 days) of every 28-day cycle at the study site Table 5 according to institutional standards. The initial FA dose is 400 mg/m² administered as a 120-minute IV infusion or as per institutional standards. Alternatively FA may be administered (via separate infusion lines) concurrently with irinotecan. Doses of FA that are omitted for AEs or any other reason should not be made up.

5-Fluorouracil will be administered IV biweekly on Days 1 and 15 (+3 days) of every 28-day cycle at the study site Table 5 immediately following completion of the FA infusion according to institutional standards. The initial 5-FU dose is 400 mg/m² bolus (not to exceed 15 minutes) administered IV on Days 1 and 15, followed by 1200 mg/m²/day×2 days (total 2400 mg/m² over 46-48 hours) continuous IV infusion or as per institutional standards. Doses of 5-FU that are omitted for AEs or any other reason should not be made up.

Dose Modifications

Patients will be monitored for AEs on an ongoing basis. The severity of AEs will be evaluated using the NCI CTCAE, v.4.03. If a patient develops a toxicity, the dose may be modified as outlined in Table 6. All dose modifications should be based on the worst preceding toxicity.

In the Safety Lead-in and Triplet Arms, if a patient permanently discontinues binimetinib due to an AE or clinically significant laboratory value, they may continue to receive encorafenib in combination with cetuximab. Due to the lack of efficacy of binimetinib, encorafenib, or cetuximab when used as single agents in patients with BRAF-mutant mCRC, patients who cannot tolerate these agents in combination with at least one other agent, should discontinue study treatment altogether, complete the end of treatment visit and continue to be followed for survival (and disease progression, if applicable).

Cetuximab may be reduced 2 dose levels to a minimum of 150 mg/m² for AEs or laboratory abnormalities (Table 6). When a dose reduction is required because of an AE, no subsequent dose re-escalation of cetuximab will be permitted for that patient for the duration of study treatment. If after resolution of an AE, treatment is resumed at the same dose, and the same toxicity reoccurs with the same severity, any re-initiation of treatment must be at the next lower dose level irrespective of duration, with some exceptions for skin toxicity. In addition, a patient must discontinue study treatment if, after treatment is resumed at a lower dose of cetuximab, the same toxicity reoccurs with the same or worse severity.

If a patient misses >28 consecutive doses of encorafenib, or binimetinib, >4 consecutive cetuximab doses, or 2 consecutive irinotecan, 5-FU or FA doses, as the result of an AE or clinically significant laboratory abnormality, then the respective agent should be discontinued. As previously noted, due to the lack of efficacy in patients with BRAF-mutant mCRC, patients will not be permitted to continue on single agent binimetinib, encorafenib or cetuximab and will be discontinued from study treatment altogether, and following completion of the end of treatment visit, will continue to be followed for survival (and disease progression, if applicable).

TABLE 6

Dose Levels for Dose Modification

| | Encorafenib (mg QD) | Binimetinib (mg BID) | Cetuximab (mg/m² once weekly) | Irinotecan (mg/m² every 2 weeks) | 5-FU Bolus (mg/m² every 2 weeks) | 5-FU Infusion (mg/m² over 46-48 hours every 2 weeks) |
|---|---|---|---|---|---|---|
| Starting Dose | 300 | 45 | 400 initial dose then 250 thereafter<sup>a</sup> | 180 | 400 | 2400 |
| Dose level - 1 | 225 | 30 | 200 | 150 | 200 | 2000 |
| Dose level - 2 | 150 | 15 | 150 | 120 | 0 | 1600 |
| Dose level - 3 | | | | 100 | 0 | 1200 |

Abbreviations: BID = twice daily; 5-FU = 5-fluorouracil; QD = once daily.
<sup>a</sup>400 mg/m² initial dose (120-minute infusion), then 250 mg/m² (60-minute infusion) thereafter.

Dose Modifications for Encorafenib and/or Binimetinib

Doses of encorafenib and/or binimetinib should be adjusted for AEs throughout the study (Table 12). In general, doses should not be reduced or interrupted for Grade 1 AEs unless the AE is a specific ocular AE referred to in Table 12 but treatment to control symptoms should be provided as appropriate, if applicable.

An individual patient may have their dose of encorafenib and/or binimetinib reduced to the dose levels specified in Table 6. The lowest recommended dose level of encorafenib is 150 mg QD and the lowest recommended dose level of binimetinib is 15 mg BID. When the AE that resulted in a dose reduction improves to and remains stable at the patient's Baseline for a minimum of 14 days, the dose can be re-escalated to the next dose level at the discretion of the Investigator, provided there are no other concomitant toxicities that would prevent drug re-escalation. There is no limit to the number of times the patient can have their dose reduced or re-escalated (in increments specified in Table 6); however:

- no dose re-escalation of encorafenib is allowed after a dose reduction due to prolonged QTcF ≥501 msec;
- no dose re-escalation of binimetinib is allowed after a dose reduction due to LVEF dysfunction or prolonged QTcF ≥501 msec;
- no dose re-escalation of binimetinib or encorafenib is allowed after a dose reduction due to retinal toxicity ≥Grade 2.

Refer to Table 12 for recommended dose modifications for encorafenib and/or binimetinib, if applicable, based on the occurrence of encorafenib and/or binimetinib treatment-related AEs.

Eye disorders that cannot be specifically graded according to NCI CTCAE, v.4.03 should be graded according to Table 7. Serous detachment of the retina should be graded according to Table 8. Uveitis should be graded according to NCI CTCAE, v.4.03 as described in Table 9. Hand-foot skin reaction should be graded according to NCI CTCAE, v.4.03 as described in Table 10. Diarrhea should be graded according to modified NCI CTCAE, v.4.03 as described in Table 11.

TABLE 7

Modified NCI CTCAE, Version 4.03 Grading of Eye Disorders

| Grade | Description |
|---|---|
| 1 | Asymptomatic or mild symptoms; clinical or diagnostic observations only; intervention not indicated |
| 2 | Moderate; minimal, local or noninvasive intervention indicated; limiting age-appropriate instrumental activities of daily living |
| 3 | Severe or medically significant but not immediately sight threatening; hospitalization or prolongation of existing hospitalization indicated; disabling; limiting self-care activities of daily living |
| 4 | Sight-threatening consequences; urgent intervention indicated; blindness (20/200 or worse) in the affected eye |

TABLE 8

NCI CTCAE, Version 4.03 Grading of Serous Detachment of the Retina

| Grade | Description |
|---|---|
| 1 | Asymptomatic (but with findings in ocular coherence tomography, fundoscopy and/or slit lamp biomicroscopy) |
| 2 | Symptomatic with moderate decrease in visual acuity (20/40 or better); limiting instrumental activities of daily living |
| 3 | Symptomatic with marked decrease in visual acuity (worse than 20/40[a]); limiting self-care activities of daily living |
| 4 | Blindness (20/200[a] or worse) in the affected eye |

Note:
For rhegmatogenous retinal detachment, grade according to NCI CTCAE v.4.03 Retinal Detachment.

TABLE 9

NCI CTCAE, Version 4.03 Grading of Uveitis

| Grade | Description |
|---|---|
| 1 | Asymptomatic; clinical or diagnostic observations only |
| 2 | Anterior uveitis; medical intervention indicated |
| 3 | Posterior or pan-uveitis |
| 4 | Blindness (20/200 or worse) in the affected eye |

TABLE 10

NCI CTCAE, Version 4.03 Grading of Hand-foot Skin Reaction (HFSR)[a]

| Grade | Description[b] |
|---|---|
| 1 | Minimal skin changes or dermatitis (e.g., erythema, edema, numbness, dysesthesia, paresthesia, tingling or hyperkeratosis) without pain |
| 2 | Skin changes (e.g., peeling, blisters, bleeding, edema, or hyperkeratosis) with pain; limiting instrumental ADL |
| 3 | Severe skin changes (e.g., peeling, ulceration, blisters, bleeding, edema, or hyperkeratosis) with pain; limiting self-care ADL |

Abbreviations: ADL = activities of daily living.
[a]HFSR or palmar-plantar erythrodysesthesia syndrome, a disorder characterized by redness, marked discomfort, swelling, and tingling in the palms of the hands or the soles of the feet;
[b]More specifics examples to Grade 1 and Grade 3 are added to facilitate proper grading [from the sorafenib package insert (West Haven, CT: Bayer Pharmaceuticals Corporation; 2007).

TABLE 11

Modified NCI CTCAE, Version 4.03 Grading of Diarrhea

| Grade | Description |
|---|---|
| 1 | Increase of <4 stools per day over Baseline; mild increase in ostomy output compared to Baseline |
| 2 | Increase of 4-6 stools per day over Baseline; moderate increase in ostomy output compared to Baseline |
| 1/2 Complicated | Definition as above (Grade 1/2) with the following complicating signs/symptoms: Moderate to severe cramping; Grade ≥2 nausea/vomiting; Decreased performance status; Fever; Sepsis; Neutropenia; Frank bleeding; Dehydration; Unresolved diarrhea after 48 hours of treatment with loperamide (including high-dose administration) and initiation of second-line treatment |

TABLE 11-continued

Modified NCI CTCAE, Version 4.03 Grading of Diarrhea

| Grade | Description |
|---|---|
| 3 | Increase of ≥7 stools per day over Baseline; incontinence; hospitalization indicated; severe increase in ostomy output compared to Baseline; limiting self-care activities of daily living |
| 4 | Life threatening consequences; urgent intervention indicated |

TABLE 12

Recommended Dose Modifications for Encorafenib-related and/or Binimetinib-related Adverse Events

| Worst toxicity CTCAE, v.4.03 Grade (unless otherwise specified[a]) | Dose Modification for Encorafenib (Doublet Arm and Triplet Arm) and for Binimetinib (Triplet Arm) |
|---|---|

Eye Disorders - Retinal Events (including serous detachment of the retina), Posterior Uveitis[c]
Note: Results and images of ocular coherence tomography (OCT) must be made available upon request.
Any visual acuity impairment at screening should be documented and should be considered as baseline.

| | |
|---|---|
| Grade 1 | Maintain dose levels of encorafenib and binimetinib and repeat ophthalmic monitoring including visual acuity assessment and OCT within 10 days
If patient remains asymptomatic (Grade 1), maintain dose level of encorafenib and binimetinib and continue the schedule of visual assessments established per protocol
If patient becomes symptomatic (blurred vision, photophobia, etc.) or visual acuity assessment shows Grade 2, follow Grade 2 dose guidelines below |
| Grade 2 | Interrupt dosing of encorafenib and binimetinib and repeat ophthalmic monitoring including visual acuity assessment and OCT within 10 days
If resolved to baseline or Grade ≤1, resume treatment at current dose level of encorafenib and binimetinib and continue the schedule of visual assessments established per protocol
If not resolved to baseline or Grade ≤1, resume treatment at 1 reduced dose level[b] of encorafenib and binimetinib and continue the schedule of visual assessments established per protocol |
| Grade 3 | Interrupt dosing of encorafenib and binimetinib and repeat ophthalmic monitoring including visual acuity assessment and OCT within 10 days:
If resolved to baseline or Grade ≤2, resume treatment at 1 reduced dose level[b] of encorafenib and binimetinib and continue the schedule of visual assessments established per protocol
If not resolved to baseline or Grade ≤2, continue the interruption and repeat the ophthalmic assessment in 10 days.
If resolved to baseline or Grade ≤2, resume treatment at 1 reduced dose level[b] of encorafenib and binimetinib and continue the schedule of visual assessments established per protocol
If remains Grade 3, permanently discontinue encorafenib and binimetinib |

TABLE 12-continued

Recommended Dose Modifications for Encorafenib-related and/or Binimetinib-related Adverse Events

| Worst toxicity CTCAE, v.4.03 Grade (unless otherwise specified$^a$) | Dose Modification for Encorafenib (Doublet Arm and Triplet Arm) and for Binimetinib (Triplet Arm) |
|---|---|
| Grade 4 | Permanently discontinue encorafenib and binimetinib and immediate follow-up with ophthalmic monitoring$^c$ |

Eye Disorder - RVO$^e$

Note: Results and images of ophthalmic examinations should be made available upon request. This includes scans/images of fluorescein angiography should a patient be assessed using this technique.

| RVO of any grade | Permanently discontinue encorafenib and binimetinib and immediately follow-up with ophthalmic monitoring$^c$ |
|---|---|

Other Eye Disorders (i.e., Non-retinal Events)

| Grade 1-2 | Maintain dose level of encorafenib and binimetinib and increase frequency of ophthalmic monitoring to at least every 14 days until stabilization or resolution |
|---|---|
| Grade 3 | Interrupt dosing of encorafenib and binimetinib and refer patient to ophthalmologist within 7 days$^c$: If resolved to Grade ≤1 in ≤21 days, resume treatment at 1 reduced dose level$^b$ of encorafenib and binimetinib If not resolved to Grade ≤1 in ≤21 days, permanently discontinue encorafenib and binimetinib and close follow-up with ophthalmic monitoring until stabilization or resolution$^c$ |
| Grade 4 | Permanently discontinue encorafenib and binimetinib and immediate follow-up with ophthalmic monitoring until stabilization or resolution$^c$ |

Liver-related Adverse Events

| Grade 1 AST or ALT > ULN to 3 × ULN | Maintain dose level of encorafenib and binimetinib |
|---|---|
| Grade 2 AST or ALT > 3 to 5.0 × ULN or 3 × baseline value$^d$ AND blood bilirubing ≤ 2.0 × ULN | Maintain dose level of encorafenib and interrupt dosing of binimetinib until resolved to Grade ≤1 (or Grade ≤2 in case of liver metastasis), then: If resolved in ≤14 days, maintain dose level of encorafenib and binimetinib If not resolved in ≤14 days, interrupt dose of encorafenib (in addition to prior binimetinib) until resolved to Grade ≤1 (or Grade ≤2 in case of liver metastasis), then resume treatment at current dose level of encorafenib and 1 reduced dose level$^b$ of binimetinib If additional occurrence: Interrupt dosing of encorafenib and binimetinib until resolved to Grade ≤1 (or Grade ≤2 in case of liver metastasis), then resume treatment at 1 reduced dose level$^b$ of encorafenib and binimetinib Treatment with encorafenib and binimetinib may be resumed sequentially at the Investigator's discretion, with encorafenib being resumed alone for one week before resuming binimetinib treatment |
| AST or ALT > 3.0 to 5.0 × ULN AND blood bilirubin$^g$ > 2.0 × ULN | Interrupt dosing of encorafenib and binimetinib until resolved to Grade ≤1, then: If resolved in ≤7 days, resume treatment at 1 reduced dose level$^b$ of encorafenib and binimetinib If not resolved in ≤7 days, permanently discontinue encorafenib and binimetinib Treatment with encorafenib and binimetinib may be resumed sequentially at the investigator's discretion, with encorafenib being resumed alone for one week before resuming binimetinib treatment |
| Grade 3 AST or ALT > 5.0 to 8.0 × ULN) AND blood bilirubin$^g$ ≤ 2.0 × ULN | Interrupt dosing of encorafenib and binimetinib until resolved to Grade ≤1 (or Grade ≤2 in case of liver metastasis), then: If resolved in ≤14 days, resume treatment at current dose level of encorafenib and binimetinib If not resolved in ≤14 days, resume treatment at 1 reduced dose level$^b$ of encorafenib and binimetinib Treatment with encorafenib and binimetinib may be resumed sequentially at the investigator's discretion, with encorafenib being resumed alone for one week before resuming binimetinib treatment If additional occurrence: Interrupt dosing of encorafenib and binimetinib until resolved to Grade ≤1 (or Grade ≤2 in case of liver metastasis), then resume treatment at 1 reduced dose level$^b$ of encorafenib and binimetinib |

TABLE 12-continued

Recommended Dose Modifications for Encorafenib-related and/or Binimetinib-related Adverse Events

| Worst toxicity CTCAE, v.4.03 Grade (unless otherwise specified[a]) | Dose Modification for Encorafenib (Doublet Arm and Triplet Arm) and for Binimetinib (Triplet Arm) |
|---|---|
| AST or ALT > 8 × ULN AND blood bilirubin[g] ≤ 2.0 × ULN | Permanently discontinue encorafenib and binimetinib |
| AST or ALT > 5.0 × ULN AND blood bilirubin[g] > 2.0 × ULN | Permanently discontinue encorafenib and binimetinib |
| Grade 4 AST or ALT > 20.0 × ULN | Permanently discontinue encorafenib and binimetinib |

Cardiac Disorders - Left Ventricular Systolic Dysfunction[a] (Dose Adjustment for Binimetinib ONLY)

| Asymptomatic absolute decrease of >10% in LVEF compared to baseline and the LVEF is below the institution's LLN (e.g., a decrease of 60% to 48% is an absolute decrease of 12%) | Interrupt dosing of binimetinib and repeat evaluation of LVEF within 2 weeks If the LVEF recovers (defined as LVEF ≥50% or ≥LLN and absolute decrease ≤10% compared to baseline) ≤21 days, resume treatment at 1 reduced dose level[b] of binimetinib after approval of the Sponsor Medical Monitor. Monitor LVEF 2 weeks after resuming binimetinib, every 4 weeks for 12 weeks and subsequently as per protocol If the LVEF does not recover in ≤21 days, permanently discontinue binimetinib. Closely monitor LVEF until resolution or for up to 16 weeks |
| Grade 3-4 | Permanently discontinue binimetinib. Closely monitor LVEF until resolution or up to 16 weeks Note: Copies of ECHO and/or MUGA scans could be requested for patients to be available to the Sponsor for patients with absolute decrease of >10% in LVEF compared to baseline and LVEF < 50% or LLN |

CK Elevation

| Grade 1-2 | Maintain dose of encorafenib and binimetinib. Ensure patient is adequately hydrated. Closely monitor CK and serum creatinine If total CK ≥ 3 × ULN, measure CK isoenzymes and myoglobin in blood or urine |
| Grade 3 > 5.0-10.0 × ULN without renal impairment (i.e., serum creatinine < 1.5 × ULN or 1.5 × baseline) | If asymptomatic, maintain dosing of encorafenib and binimetinib. Ensure patient is adequately hydrated. Monitor and measure isoenzymes and myoglobin in blood or urine and serum creatinine If symptomatic (muscle pain/spasms/muscle weakness), maintain dosing of encorafenib and interrupt dosing of binimetinib until resolved to CTCAE Grade ≤ 1 and monitor closely, then: If resolved in ≤21 days, maintain dose of encorafenib and resume treatment at 1 reduced dose level[b] of binimetinib If not resolved in ≤21 days, maintain dose of encorafenib and permanently discontinue binimetinib |
| Grade 4 without renal impairment (i.e., serum creatinine < 1.5 × ULN or 1.5 × baseline) | If asymptomatic, maintain dose of encorafenib and interrupt dosing of binimetinib. Ensure patient is adequately hydrated. Monitor and measure isoenzymes and myoglobin in blood or urine and serum creatinine If resolved in ≤21 days, maintain dose of encorafenib and resume treatment at 1 reduced dose level[b] of binimetinib If not resolved in ≤21 days, maintain dose of encorafenib and permanently discontinue binimetinib If symptomatic (muscle pain/spasms/muscle weakness), maintain dose of encorafenib and permanently discontinue binimetinib |

TABLE 12-continued

Recommended Dose Modifications for Encorafenib-related and/or Binimetinib-related Adverse Events

| Worst toxicity CTCAE, v.4.03 Grade (unless otherwise specified[a]) | Dose Modification for Encorafenib (Doublet Arm and Triplet Arm) and for Binimetinib (Triplet Arm) |
|---|---|
| Grade 3 or 4 with renal impairment (i.e., serum creatinine ≥ 1.5 × ULN or 1.5 × baseline) | Interrupt dosing of encorafenib and binimetinib until resolved to CTCAE Grade < 1 or baseline level. Ensure patient is adequately hydrated. Monitor closely and measure isoenzymes and myoglobin in blood or urine and serum creatinine, then:<br>If resolved in ≤21 days, consider resuming treatment at 1 reduced dose level[b] of encorafenib and binimetinib<br>If not resolved in ≤21 days, permanently discontinue encorafenib and binimetinib<br>$2^{nd}$ occurrence:<br>Permanently discontinue encorafenib and binimetinib |
| Cardiac Investigation - Prolongation of the QT interval QTcF value | |
| QTcF > 500 ms during treatment and change from pre-treatment value remains ≤60 ms | $1^{st}$ occurrence:<br>Temporarily interrupt dosing of encorafenib and binimetinib until QTcF < 500 ms. Then resume treatment at 1 reduced dose level[b] of encorafenib and binimetinib<br>$2^{nd}$ occurrence:<br>Temporarily interrupt dosing of encorafenib and binimetinib treatment until QTcF < 500 ms. Then resume treatment at 1 reduced dose level[b] of encorafenib and binimetinib<br>$3^{rd}$ occurrence:<br>Permanently discontinue encorafenib and binimetinib |
| QTcF increase during treatment is both >500 ms and >60 ms change from pre-treatment values | Permanently discontinue encorafenib and binimetinib |
| Rash [see cetuximab dose modifications (Table 13)] | |
| Grade 1 | Maintain dose level of encorafenib and binimetinib<br>Initiate Initial Rash Treatment Regimen if it was not already started and rash should be closely monitored |
| Grade 2 | $1^{st}$ occurrence:<br>Maintain dose level of encorafenib and binimetinib<br>Initiate Initial Rash Treatment Regimen if it was not already started and rash should be closely monitored<br>Reassess within ≤14 days. If rash worsens or does not improve, interrupt dosing of encorafenib and binimetinib until resolved to Grade ≤1. Then resume treatment at current dose level of encorafenib and binimetinib. For dermatitis acneiform, treatment with encorafenib may be maintained if, in the judgment of the investigator, the rash is considered to be unrelated to encorafenib. If treatment with encorafenib was maintained and no improvement within 8 days, interrupt dosing of encorafenib<br>$2^{nd}$ occurrence:<br>Reassess within ≤14 days. If rash worsens or does not improve, interrupt dosing of encorafenib and binimetinib until resolved to Grade ≤1. Then resume treatment at current dose level of encorafenib and 1 reduced dose level[b] of binimetinib. For dermatitis acneiform rash, treatment with encorafenib may be maintained if, in the judgment of the investigator, the rash is considered to be unrelated to encorafenib. If treatment with encorafenib was maintained and no improvement within 8 days, interrupt dosing of encorafenib |
| Grade 3 | $1^{st}$ occurrence:<br>Interrupt dosing of encorafenib and binimetinib until resolved to Grade ≤1. Reassess weekly. Then resume treatment at current dose level of encorafenib and binimetinib.<br>Consider referral to dermatologist and manage rash per dermatologist's recommendation. |

TABLE 12-continued

Recommended Dose Modifications for Encorafenib-related and/or Binimetinib-related Adverse Events

| Worst toxicity CTCAE, v.4.03 Grade (unless otherwise specified$^a$) | Dose Modification for Encorafenib (Doublet Arm and Triplet Arm) and for Binimetinib (Triplet Arm) |
|---|---|
| | $2^{nd}$ occurrence:<br>Interrupt dosing of encorafenib and binimetinib until resolved to Grade ≤1. Then resume treatment at 1 reduced dose level$^b$ of encorafenib and binimetinib.<br>Resume treatment with encorafenib at the same dose level if, in the judgment of the Investigator, the rash is considered to be unrelated to encorafenib<br>Consider referral to dermatologist and manage rash per dermatologist's recommendation |
| Grade 4 | Permanently discontinue encorafenib and binimetinib$^f$ |

Hand-foot Skin Reaction (HFSR)/Palmar-plantar Erythrodysesthesia Syndrome$^e$ (Dose Adjustment for Encorafenib ONLY)

| | |
|---|---|
| Grade 1 | Maintain dose of encorafenib. Promptly institute supportive measures, such as topical therapy, for symptomatic relief. Give instruction on life-style modifications. |
| Grade 2 | $1^{st}$ occurrence:<br>Maintain dose of encorafenib and HFSR should be closely monitored. Promptly institute supportive measures, such as topical therapy, for symptomatic relief. Give instruction on life-style modifications.<br>If no improvement ≤14 days, interrupt dosing of encorafenib until resolved to Grade ≤1. Resume treatment with encorafenib at current dose level. Continue supportive measures, such as topical therapy, for symptomatic relief. Give instruction on life-style modifications.<br>Additional occurrence:<br>Treatment with encorafenib may be maintained or interrupted based upon the Investigator's discretion. Continue supportive measures, such as topical therapy, for symptomatic relief. Give instruction on life-style modifications.<br>If interrupted dosing of encorafenib per investigator's judgment, interrupt until resolved to Grade ≤1. Resume treatment with encorafenib at the same dose level or 1 reduced dose level$^b$ based upon the Investigator's discretion. |
| Grade 3 | $1^{st}$ or additional occurrence:<br>Interrupt dosing of encorafenib until resolved to Grade ≤1. Promptly initiate supportive measures, such as topical therapy, for symptomatic relief. Give instruction on life-style modifications. Reassess the patient weekly.<br>Then resume treatment at one reduced dose level$^b$ of encorafenib<br>Consider referral to dermatologist and manage HFSR per dermatologist's recommendation<br>>$3^{nd}$ occurrence:<br>Interrupt dosing of encorafenib until resolved to Grade ≤1, decision to resume treatment with encorafenib at one reduced dose level$^b$ or permanently discontinue encorafenib should be based upon the Investigator's discretion. |

SCC, KA and any Other Suspicious Skin Lesion (Dose Adjustment for Encorafenib ONLY)

| | |
|---|---|
| Grade ≤ 3 | Maintain dose of encorafenib (dose interruptions or modifications are not required). Treatment of SCC, KA, and any other suspicious skin lesion (eg. new primary melanoma) should occur based upon institutional practice. |

Diarrhea

| | |
|---|---|
| Uncomplicated Grade 1-2 | Maintain dose of encorafenib. Consider temporary interruption of binimetinib until resolved to Grade ≤1. Then resume treatment at current dose level of binimetinib |
| Complicated Grade 1-2 | Consider temporary interruption of encorafenib until resolved to Grade ≤1. Then resume treatment at current dose level of encorafenib<br>Interrupt dosing of binimetinib until resolved to Grade ≤1. Then resume treatment at 1 reduced dose level$^b$ of binimetinib |

TABLE 12-continued

Recommended Dose Modifications for Encorafenib-related
and/or Binimetinib-related Adverse Events

| Worst toxicity CTCAE, v.4.03 Grade (unless otherwise specified[a]) | Dose Modification for Encorafenib (Doublet Arm and Triplet Arm) and for Binimetinib (Triplet Arm) |
|---|---|
| Grade 3-4 | Interrupt dosing of encorafenib and binimetinib until resolved to Grade ≤1. Then resume treatment at current dose level of encorafenib if, in the judgment of the Investigator, the toxicity is considered to be unrelated to encorafenib, or at one reduced dose level[b]. Resume treatment at 1 reduced dose level[b] of binimetinib |
| | Nausea/Vomiting |
| Grade 1-2 | Maintain dose level of encorafenib and binimetinib. Promptly institute antiemetic measure. |
| Grade 3 | Interrupt dosing of encorafenib and binimetinib until resolved to Grade ≤1. Then resume treatment at 1 reduced dose level[b] of encorafenib. Resume treatment with binimetinib at the current dose if, in the judgment of the Investigator, the toxicity is considered to be unrelated to binimetinib, or at 1 reduced dose level[b]. Note: Interrupt dosing of encorafenib and binimetinib for ≥Grade 3 vomiting or Grade 3 nausea only if the vomiting or nausea cannot be controlled with optimal antiemetics (as per local practice) |
| Grade 4 | Permanently discontinue encorafenib and binimetinib[f] |
| | Interstitial lung disease/pneumonitis |
| Grade 1 | Maintain dose level of encorafenib and binimetinib. Monitor weekly. |
| Grade 2 | Maintain dose of encorafenib. Withhold binimetinib for up to 3 weeks. If improved to Grade 0 or 1, resume treatment at 1 reduced dose level of binimetinib. If not resolved within 3 weeks, permanently discontinue binimetinib. |
| Grade 3-4 | Permanently discontinue binimetinib. |
| | All Other Adverse Events (Suspected To Be Related To Encorafenib and/or Binimetinib) |
| Grade 1-2 | If the event is a persistent Grade 2 AE not responsive to a specific therapy, consider interruption or reduction of encorafenib and binimetinib, as applicable |
| Grade 3 | Interrupt dosing of encorafenib and binimetinib until resolved to Grade ≤1 or to pretreatment/baseline level. If the event resolves ≤21 days, then study drug may be resumed at 1 reduced dose level[b] based upon the Investigator's discretion. |
| Grade 4 | Permanently discontinue encorafenib and binimetinib[f] |

[a]Not according to NCI CTCAE

[b]Dose reduction below 75 mg QD for encorafenib, and below 15 mg BID for binimetinib is not allowed.

[c]Ophthalmic monitoring mandated for retinal events, posterior uveitis, RVO: further evaluation with specialized retinal imaging (e.g. ocular coherence tomography, fluorescein angiography). Any diagnosis of retinal events must be supported by presence or absence of symptoms, visual acuity assessment and findings in OCT.

[d]For patients enrolled with liver metastases and baseline LFT elevations.

[e]Disorder characterized by redness, marked discomfort, swelling, and tingling in the palms of the hands or the soles of the feet.

[f]A patient with a Grade 4 AE may resume treatment at the lower dose level if the AE recovers to Grade ≤ 1 within 28 days of discontinuing drug and, if in the opinion of the Investigator and Sponsor Medical Monitor, the event is not life-threatening and the patient can be managed and monitored for recurrence of AE. Any patients requiring a treatment interruption of duration >28 days must discontinue study drug permanently.

[g]Refers to total bilirubin.

Modifications for Cetuximab

Recommended dose modifications for cetuximab based on the occurrence of cetuximab treatment-related AEs are summarized in Table 1.

TABLE 13

Recommended Dose Modifications for Cetuximab-related Adverse Events

| Worst toxicity CTCAE, v.4.03 Grade | Dose Modification for Cetuximab During a Cycle of Therapy |
|---|---|
| Infusion Reaction | If an infusion reaction occurs while cetuximab is being infused, the infusion should be stopped immediately and the patient should be evaluated. |
| Grade 1 or 2 | Restart and complete the disrupted infusion at the discretion of the Investigator. The infusion must be restarted at a reduced rate. Additional pre-medications such as antihistamines or low-dose systemic corticosteroids may be administered when the infusion is restarted per instutional standards. All subsequent infusions must also be administered at the reduced rate. |
| Grade 3 or 4 | Permanently discontinue cetuximab |
| Rash [see encorafenib and/or binimetinib dose modifications (Table 12)] | |
| Grade 1 or 2 | Maintain dose level; consider initiating appropriate therapy (such as antihistamines, topical corticosteroids, and low-dose systemic corticosteroids) |
| Grade 3, despite therapy | Omit dose until resolved to ≤Grade 2, then: If resolved in ≤7 days (or ≤14 days for acneiform rash), then maintain dose level If not resolved in ≤7 days despite appropriate skin toxicity therapy (or ≤14 days for acneiform rash), then permanently discontinue cetuximab |
| Grade 3 recurrent | Omit dose until resolved to ≤Grade 2, then: If resolved in ≤7 days (or ≤14 days for acneiform rash), then decrease 1 dose level If not resolved in ≤7 days despite appropriate skin toxicity therapy (or ≤14 days for acneiform rash), then permanently discontinue cetuximab Permanently discontinue cetuximab after 3rd recurrence (upon 4th occurrence) |
| Grade 4, despite skin toxicity therapy | Permanently discontinue cetuximab |

Example 3

Preparation of Crystallized 6-(4-bromo-2-fluorophenylamino)-7-fluoro-3-methyl-3H-benzoimidazole-5-carboxylic acid (2-hydroxyethyoxy)-amide The preparation of crystallized 6-(4-bromo-2-fluorophenylamino)-7-fluoro-3-methyl-3H-benzoimidazole-5-carboxylic acid (2-hydroxyethyoxy)-amide is described in PCT publication No. WO 2014/063024 as follows.

Figure 8:
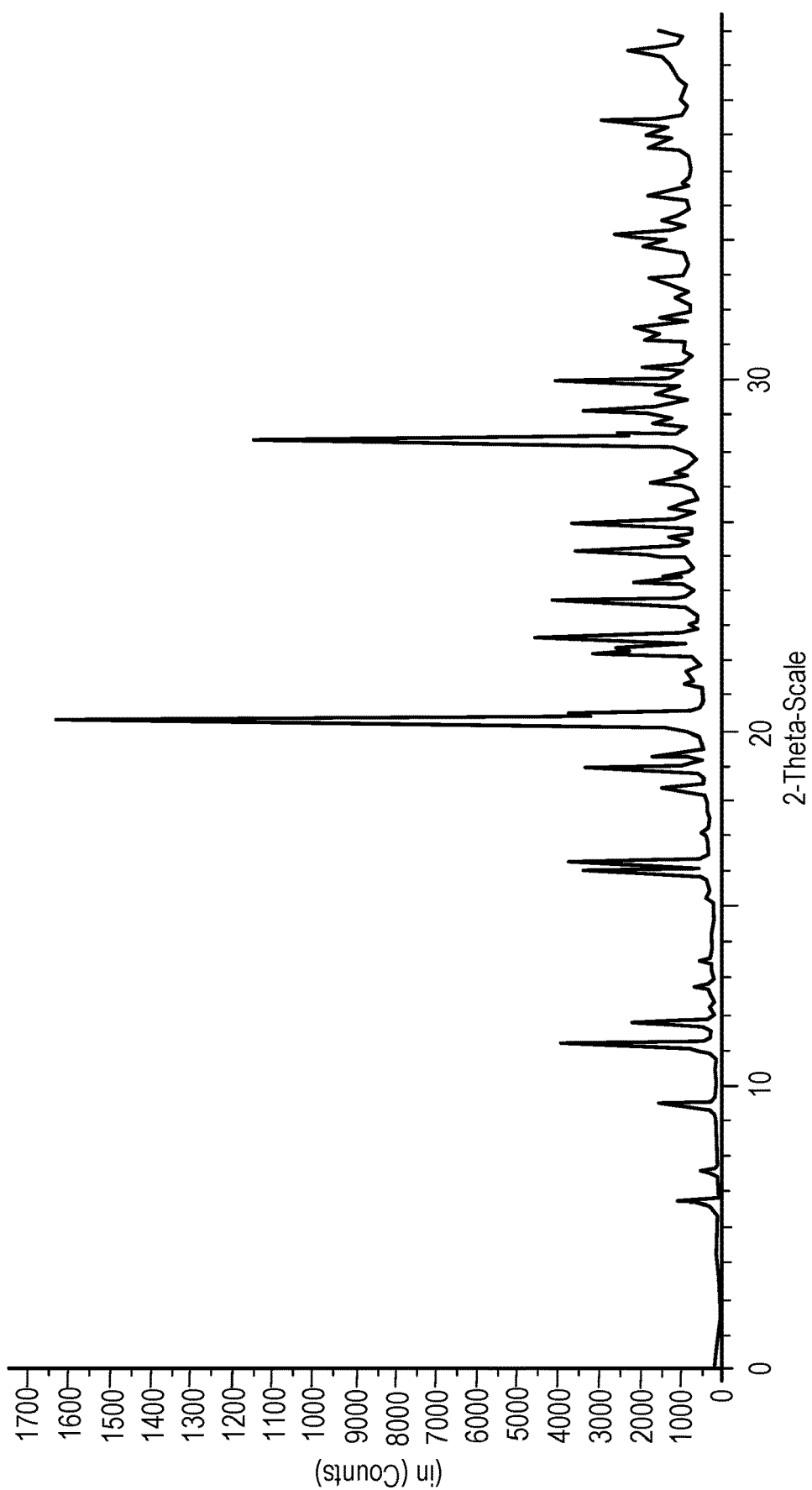
FIG. 8 shows an X-ray powder diffraction pattern for crystallized 6-(4-bromo-2-fluorophenylamino)-7-fluoro-3-methyl-3H-benzoimidazole-5-carboxylic acid (2-hydroxyethoxy)-amide prepared according to Example 3.

In a dry vessel at room temperature, 6-(4-bromo-2-fluorophenylamino)-7-fluoro-3-methyl-3H-benzoimidazole-5-carboxylic acid (2-hydroxyethoxy)-amide was added to a premixed solvent solution of methanol/THF/water (35/35/30 w/w/w). The suspension was heated to internal temperature 53-55° C., and the resulting solution was hot filtered by deep and membrane filtration (via a paper filter and PTFE membrane) at internal temperature 53-56° C. The clear solution was stirred and cooled to 47-48° C., and the seed crystals suspension (i.e., seed crystals of crystallized 6-(4-bromo-2-fluorophenylamino)-7-fluoro-3-methyl-3H-benzoimidazole-5-carboxylic acid (2-hydroxyethoxy)-amide in water, 10% m/m) was added (0.2 to 0.5% of crystallized 6-(4-bromo-2-fluorophenylamino)-7-fluoro-3-methyl-3H-benzoimidazole-5-carboxylic acid (2-hydroxyethoxy)-amide expected yield mass). After about 20 minutes, water was slowly added within 25 hours (33.3% within 15 hours and 66.6% within 10 hours with at least 10 minute stirring after addition of water) to obtain a final ratio of methanol/THF/water (20/20/60 w/w/w). After the water was added, the suspension was cooled down to internal temperature 3-5° C. within 10 hours and stirred for 0.5 hours. The white suspension was filtered over a sinter glass nutsche (75 mL, diameter=6 cm, pore 3) suction filter and washed once with ice cold methanol/THF/water (15/15/70 w/w at 2-4° C.), and two times with ice cold water (2-4° C.). Drying takes place in a vacuum oven dryer at 20° C. for 10 hours, and then at 40° C. for 10 hours, and then at 60° C. for at least 12 hours with pressure <10 mbar, providing crystallized 6-(4-bromo-2-fluorophenylamino)-7-fluoro-3-methyl-3H-benzoimidazole-5-carboxylic acid (2-hydroxyethoxy)-amide, which can be distinguished by the XRPD pattern in FIG. 8.

Example 4

Pharmaceutical Composition of Crystallized 6-(4-bromo-2-fluorophenylamino)-7-fluoro-3-methyl-3H-benzoimidazole-5-carboxylic acid (2-hydroxyethyoxy)-amide Crystallized 6-(4-bromo-2-fluorophenylamino)-7-fluoro-3-methyl-3H-benzoimidazole-5-carboxylic acid (2-hydroxyethoxy)-amide was formulated as indicated in Table 14:

TABLE 14

| Formulation | | Form 1 (% by weight) | Form 1 (in mg/ unit) | Form 2 (% by weight) | Form 2 (in mg/ unit) |
|---|---|---|---|---|---|
| Tablet core | | | | | |
| Crystallized 6-(4-bromo-2-fluorophenylamino)-7-fluoro-3-methyl-3H-benzoimidazole-5-carboxylic acid (2-hydroxyethyoxy)-amide (Compound B) | | 6.25% | 15 | 10.00% | 15.00 |
| Lactose monohydrate | Filler | 55.63% | 133.5 | 55.62% | 83.43 |
| Microcrystalline cellulose | Filler | 35.13% | 84.3 | 31.37% | 47.06 |
| Croscarmellose Sodium | Disintegrant | 2.00% | 4.8 | 2.00% | 3 |
| Magnesium Stearate | Lubricant | 0.75% | 1.8 | 0.75% | 1.13 |
| Colloidal Silicon Dioxide/Silica, colloidal anhydrous(e.g., Aerosil 200 ©) | Glidant | 0.25% | 0.6 | 0.25% | 0.38 |
| TOTAL: | | | 240 | | 150 |
| Tablet coating | | | | | |
| Tablet core (from above) | | 100% | | 100% | |
| Opadry II (Yellow) ®** | Film coat | 3.50% | 8.4 | 3.50% | 8.4 |
| Sterile water for irrigation*** | Solvent | — | | — | |

\* The weight of the drug substance is taken with reference to the dried substance (100%) on the basis of assayed value. The difference in weight is adjusted by the amount of lactose monohydrate.
\*\*The Opadry II is combined with the sterile water to make a 12% w/w Opadry II (85 F) film coat suspension, which is then sprayed onto the core tablet.
\*\*\*Removed during processing Upon mixing of the tablet core components, the pharmaceutical composition is converted into a tablet form by direct compression. The formed tablet may be further coated with the tablet coating provided above.

What is claimed is:

1. A method for increasing the overall survival, objective response rate, time to progression, progression-free survival, time-to-treatment failure, or Duration of Response (DOR) of a patient having a B-Raf mutant colorectal cancer, the method comprising administering to a patient in need thereof a combination therapy comprising therapeutically effective amounts, independently, of:
   (a) a BRAF inhibitor which is methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate (COMPOUND A) or a pharmaceutically acceptable salt thereof,
   (b) MEK inhibitor (COMPOUND B) which is 6-(4-bromo-2-fluorophenylamino)-7-fluoro-3-methyl-3H-benzoimidazole-5-carboxylic acid(2-hydroxyethoxy)-amide, or a pharmaceutically acceptable salt thereof, and
   (c) an anti-EGFR antibody (COMPOUND C) which is cetuximab.

2. The method of claim 1, wherein the BRAF inhibitor is amorphous methyl N-[(2 S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate or a pharmaceutically acceptable salt thereof.

3. The method according to claim 1, wherein said MEK inhibitor is crystallized 6-(4-bromo-2-fluorophenylamino)-7-fluoro-3-methyl-3H-benzoimidazole-5-carboxylic acid (2-hydroxyethoxy)-amide characterized by having XRPD diffraction peaks (2θ degrees) at 20.38 and 28.39.

4. The method according to claim 3, wherein said crystallized 6-(4-bromo-2-fluorophenylamino)-7-fluoro-3-methyl-3H-benzoimidazole-5-carboxylic acid (2-hydroxyethoxy)-amide is characterized by having XRPD diffraction peaks (2θ degrees) at 20.38, 28.39, and 11.18.

5. The method according to claim 3, wherein said crystallized 6-(4-bromo-2-fluorophenylamino)-7-fluoro-3-methyl-3H-benzoimidazole-5-carboxylic acid (2-hydroxyethoxy)-amide is characterized by having XRPD diffraction peaks (2θ degrees) at 20.38, 28.39, 11.18, and 29.18.

6. The method according to claim 3, wherein said crystallized 6-(4-bromo-2-fluorophenylamino)-7-fluoro-3-methyl-3H-benzoimidazole-5-carboxylic acid (2-hydroxyethoxy)-amide is characterized by having XRPD diffraction peaks (2θ degrees) at 20.38, 28.39, 11.18, 29.18, 22.43, and 22.75.

7. The method according to claim 3, wherein said crystallized 6-(4-bromo-2-fluorophenylamino)-7-fluoro-3-methyl-3H-benzoimidazole-5-carboxylic acid (2-hydroxyethoxy)-amide is characterized by having XRPD diffraction peaks (2θ degrees) at 20.38, 28.39, 11.18, 29.18, 22.43, 22.75, 25.23, 16.05, and 11.82.

8. The method according to claim 3, wherein said crystallized 6-(4-bromo-2-fluorophenylamino)-7-fluoro-3-methyl-3H-benzoimidazole-5-carboxylic acid (2-hydroxyethoxy)-amide is characterized by having XRPD diffraction peaks (2θ degrees) at 20.38, 28.39, 11.18, 29.18, 22.43, 22.75, 25.23, 16.05, 11.82, 23.74, 16.33, and 19.00.

9. The method according to claim 1, wherein the colorectal cancer is metastatic colorectal cancer.

10. The method according to claim 1, wherein the colorectal cancer is a colorectal cancer having a BRAF V600 mutation.

11. The method according to claim 10, wherein the colorectal cancer is a cancer having a BRAF V600E mutation.

12. The method according to claim 1, wherein the therapeutically effective amount of COMPOUND A is orally administered once daily.

13. The method according to claim 12 wherein the therapeutically effective amount of COMPOUND A is 300 mg, which is orally administered once daily.

14. The method according to claim 1, wherein the therapeutically effective amount of COMPOUND B is orally administered twice daily as first and second therapeutically effective doses.

15. The method according to claim 14, wherein said first and second therapeutically effective dose of COMPOUND B each comprises 45 mg of COMPOUND B.

16. The method according to claim 1, wherein said subject was treated with at least one systemic anticancer therapy agent for a period of time prior to treatment with said combination therapy.

* * * * *